United States Patent
Ye et al.

(10) Patent No.: US 8,039,125 B2
(45) Date of Patent: *Oct. 18, 2011

(54) COMPOUND COMPRISING PHENYL PYRIDINE UNITS

(75) Inventors: Qing Ye, Schenectady, NY (US);
Yangang Liang, Shanghai (CN);
Shengxia Liu, Shanghai (CN); Kelly Scott Chichak, Clifton Park, NY (US);
Jie Liu, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 304 days.

This patent is subject to a terminal disclaimer.

(21) Appl. No.: 12/258,880

(22) Filed: Oct. 27, 2008

(65) Prior Publication Data

US 2009/0289547 A1 Nov. 26, 2009

Related U.S. Application Data

(63) Continuation-in-part of application No. 12/125,296, filed on May 22, 2008.

(51) Int. Cl.
*C07F 5/02* (2006.01)
*C07D 401/10* (2006.01)
*C07D 401/14* (2006.01)
*C07D 405/14* (2006.01)
*H01J 63/04* (2006.01)
*H01L 51/54* (2006.01)

(52) U.S. Cl. ........ 428/690; 428/917; 313/504; 313/506; 546/255; 546/261; 546/256; 546/13; 257/40

(58) Field of Classification Search ............... None
See application file for complete search history.

(56) References Cited

U.S. PATENT DOCUMENTS

| | | | |
|---|---|---|---|
| 6,023,371 A | 2/2000 | Onitsuka et al. | |
| 6,169,163 B1 | 1/2001 | Woo et al. | |
| 6,255,449 B1 | 7/2001 | Woo et al. | |
| 6,309,763 B1 | 10/2001 | Woo et al. | |
| 6,362,310 B1 | 3/2002 | Woo et al. | |
| 6,512,083 B1 | 1/2003 | Woo et al. | |
| 6,514,632 B1 | 2/2003 | Woo et al. | |
| 6,605,373 B2 | 8/2003 | Woo et al. | |
| 7,056,600 B2 | 6/2006 | Andriessen | |
| 7,116,308 B1 | 10/2006 | Heeks et al. | |
| 2007/0241675 A1 | 10/2007 | Kim et al. | |
| 2009/0289547 A1* | 11/2009 | Ye et al. | 313/504 |
| 2010/0174086 A1* | 7/2010 | Chichak et al. | 546/256 |
| 2010/0276639 A1* | 11/2010 | Ye et al. | 252/301.35 |

FOREIGN PATENT DOCUMENTS

| | | | |
|---|---|---|---|
| EP | 1672961 A1 | 6/2006 | |
| JP | 2003-282270 A | * | 10/2003 |
| JP | 2007015993 A | 1/2007 | |
| JP | 2008063232 A | 3/2008 | |

OTHER PUBLICATIONS

Machine translation for JP 2003-282270 A, which was published Oct. 2003.*
PCT International Search Report dated Jul. 14, 2009.
Promarak et al., "Synthesis and Properties of Stable Amorphous Hole-Transporting Molecules for Electroluminescent Devices", Science Direct, Tetrahedron Letters, vol. 47, pp. 8949-8952, 2006.
Su et al., "Novel Four-Pyridylbenzene-Armed Biphenyls as Electron-Transport Materials for Phosphorescent OLEDs", Organic Letters, vol. 10, No. 5, pp. 941-944, 2008.

* cited by examiner

*Primary Examiner* — Dawn L. Garrett
(74) *Attorney, Agent, or Firm* — Mary Louise Gioeni

(57) ABSTRACT

Organic compounds of formula I may be used in optoelectronic devices

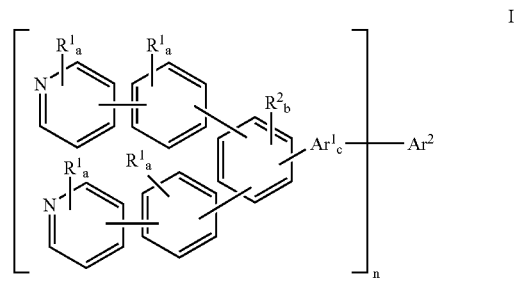

wherein $R^1$ is, independently at each occurrence, a $C_1$-$C_{20}$ aliphatic radical, a $C_3$-$C_{20}$ aromatic radical, or a $C_3$-$C_{20}$ cycloaliphatic radical;

$R^2$ is, independently at each occurrence, a $C_1$-$C_{20}$ aliphatic radical, a $C_3$-$C_{20}$ aromatic radical, or a $C_3$-$C_{20}$ cycloaliphatic radical;

a is, independently at each occurrence, an integer ranging from 0-4;

b is, independently at each occurrence, an integer ranging from 0-3;

$Ar^1$ is a direct bond or heteroaryl, aryl, or alkyl or cycloalkyl;

$Ar^2$ is heteroaryl, aryl, or alkyl or cycloalkyl;

c is 0, 1 or 2; and n is an integer ranging from 2-4.

11 Claims, No Drawings

COMPOUND COMPRISING PHENYL PYRIDINE UNITS

CROSS REFERENCE TO RELATED APPLICATIONS

This application is a Continuation-in-Part of U.S. patent application Ser. No. 12/125,296 filed on May 22, 2008 and entitled COMPOUND COMPRISING PHENYL PYRIDINE UNITS.

BACKGROUND

The invention relates generally to organic compounds, and particularly to organic compounds comprising phenyl pyridine units and optoelectronic devices using the same.

Optoelectronic devices, e.g. Organic Light Emitting Devices (OLEDs), which make use of thin film materials that emit light when subjected to a voltage bias, are expected to become an increasingly popular form of flat panel display technology. This is because OLEDs have a wide variety of potential applications, including cell phones, personal digital assistants (PDAs), computer displays, informational displays in vehicles, television monitors, as well as light sources for general illumination. Due to their bright colors, wide viewing angle, compatibility with full motion video, broad temperature ranges, thin and conformable form factor, low power requirements and the potential for low cost manufacturing processes, OLEDs are seen as a future replacement technology for cathode ray tubes (CRTs) and liquid crystal displays (LCDs). Due to their high luminous efficiencies, OLEDs are seen as having the potential to replace incandescent, and perhaps even fluorescent, lamps for certain types of applications.

OLEDs possess a sandwiched structure, which consists of one or more organic layers between two opposite electrodes. For instance, multi-layered devices usually comprise at least three layers: a hole injection/transport layer, an emissive layer and an electron transport layer (ETL). Furthermore, it is also preferred that the hole injection/transport layer serves as an electron blocking layer and the ETL as a hole blocking layer. Single-layered OLEDs comprise only one layer of materials between two opposite electrodes.

BRIEF DESCRIPTION

In one aspect, the invention relates to organic compounds of formula I:

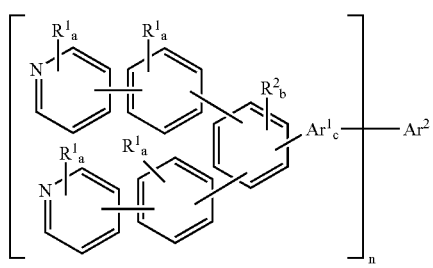

wherein
$R^1$ is, independently at each occurrence, a $C_1$-$C_{20}$ aliphatic radical, a $C_3$-$C_{20}$ aromatic radical, or a $C_3$-$C_{20}$ cycloaliphatic radical;

$R^2$ is, independently at each occurrence, a $C_1$-$C_{20}$ aliphatic radical, a $C_3$-$C_{20}$ aromatic radical, or a $C_3$-$C_{20}$ cycloaliphatic radical;

a is, independently at each occurrence, an integer ranging from 0-4;

b is, independently at each occurrence, an integer ranging from 0-3;

$Ar^1$ is a direct bond or heteroaryl, aryl, or alkyl or cycloalkyl;

$Ar^2$ is heteroaryl, aryl, or alkyl or cycloalkyl;

c is 0, 1 or 2; and n is an integer ranging from 2-4.

In another aspect, the invention relates to optoelectronic devices comprising at least one organic compound of formula I, particularly where the compound is present in an electron-transporting layer.

DETAILED DESCRIPTION

Organic compounds of formula I have properties useful in optoelectronic devices, e.g., organic light emitting devices (OLEDs), and are particularly well suited for use in electron-transporting layers thereof.

In one aspect, the present invention relates to compounds of formula II

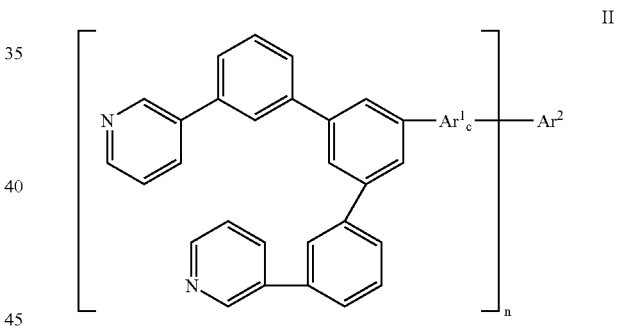

In another aspect, the present invention relates to compounds of formula VIII

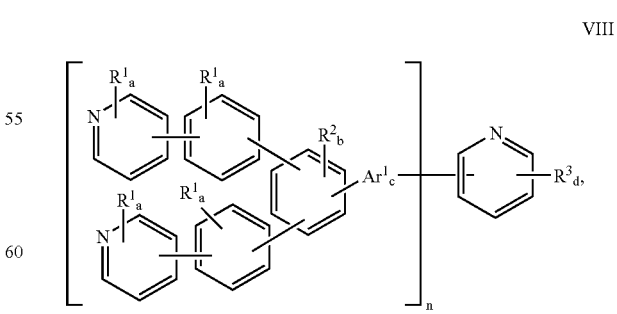

wherein $R^3$ is independently at each occurrence, a $C_1$-$C_{20}$ aliphatic radical, a $C_3$-$C_{20}$ aromatic radical, or a $C_3$-$C_{20}$ cycloaliphatic radical and d is an integer ranging from 0-4.

In another aspect, the present invention relates to compounds of formula IX
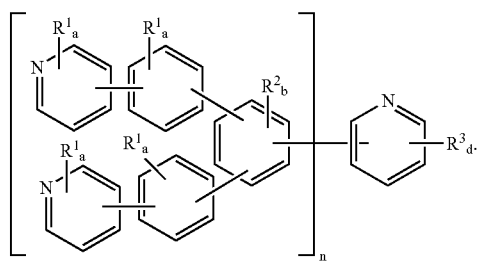
IX
In another aspect, the present invention relates to compounds of formula X
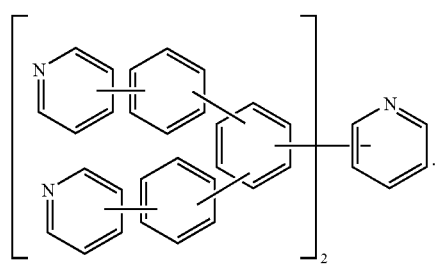
X
For the compounds of formula I, II and VIII, $Ar^1$ is independently chosen from
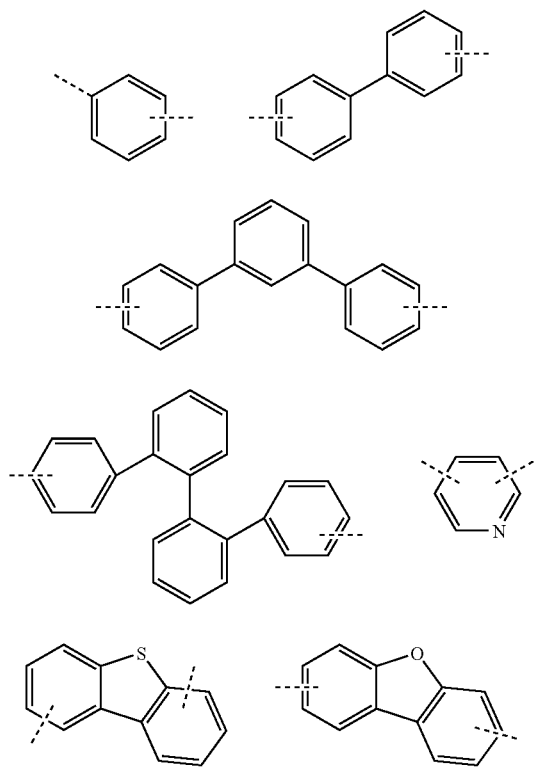
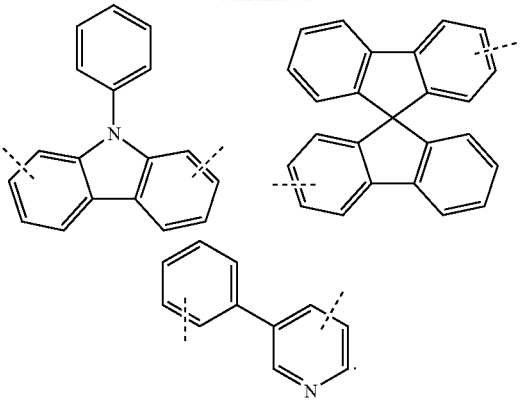
Examples of groups that may be used as $Ar^2$ include
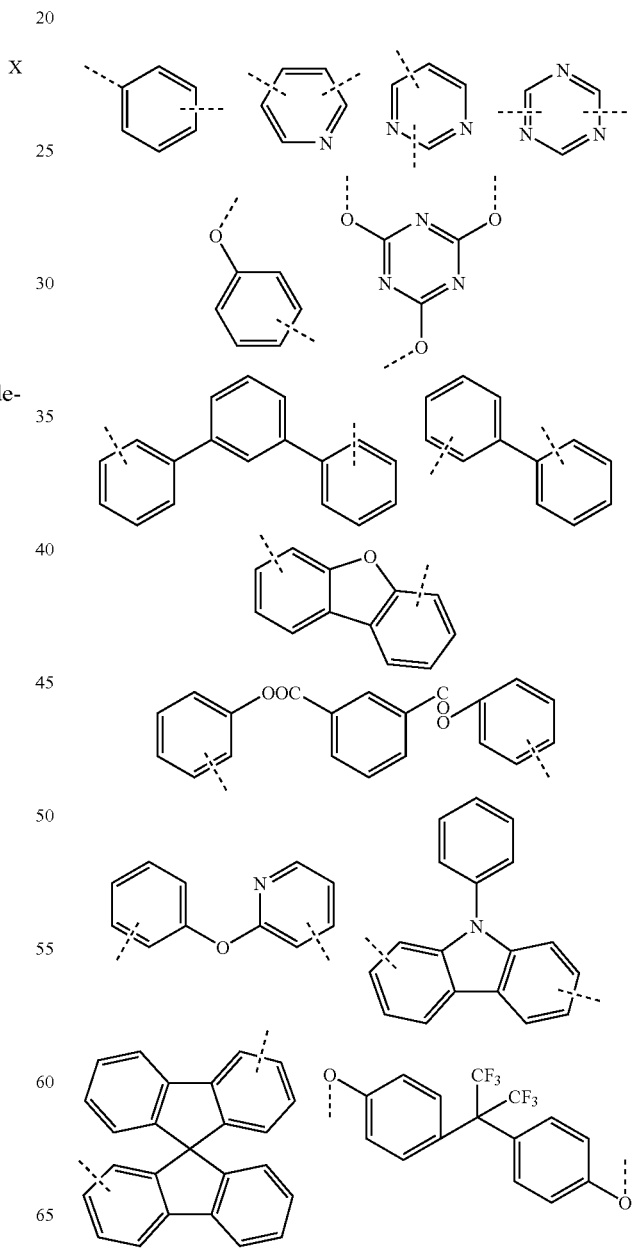

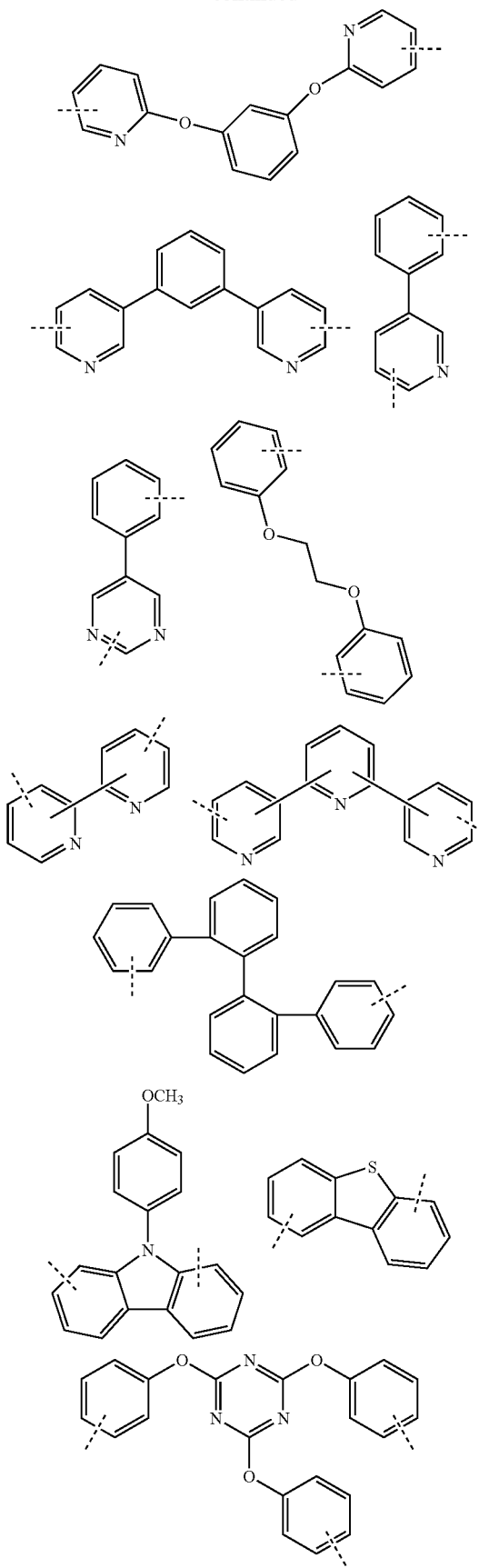
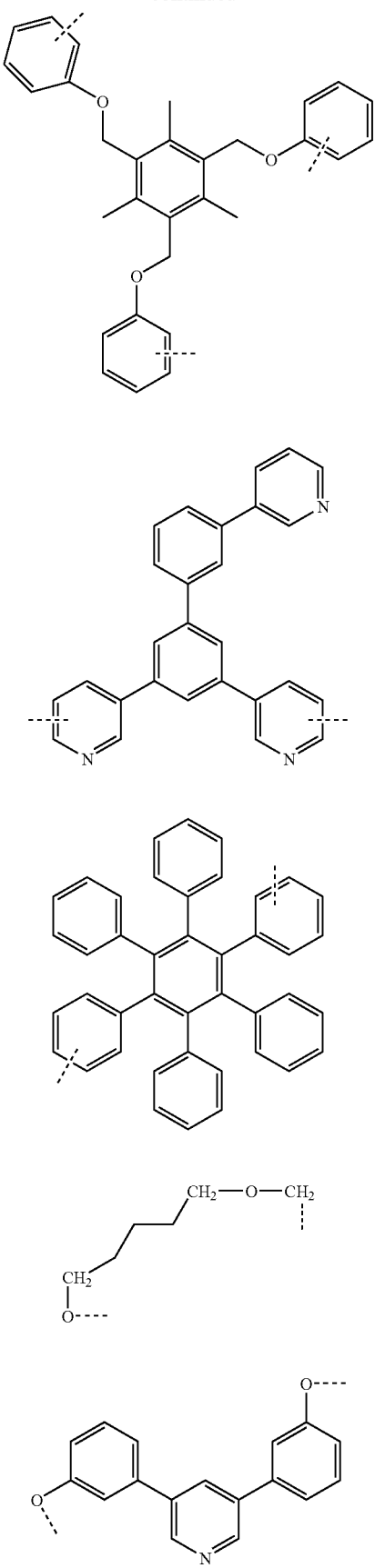

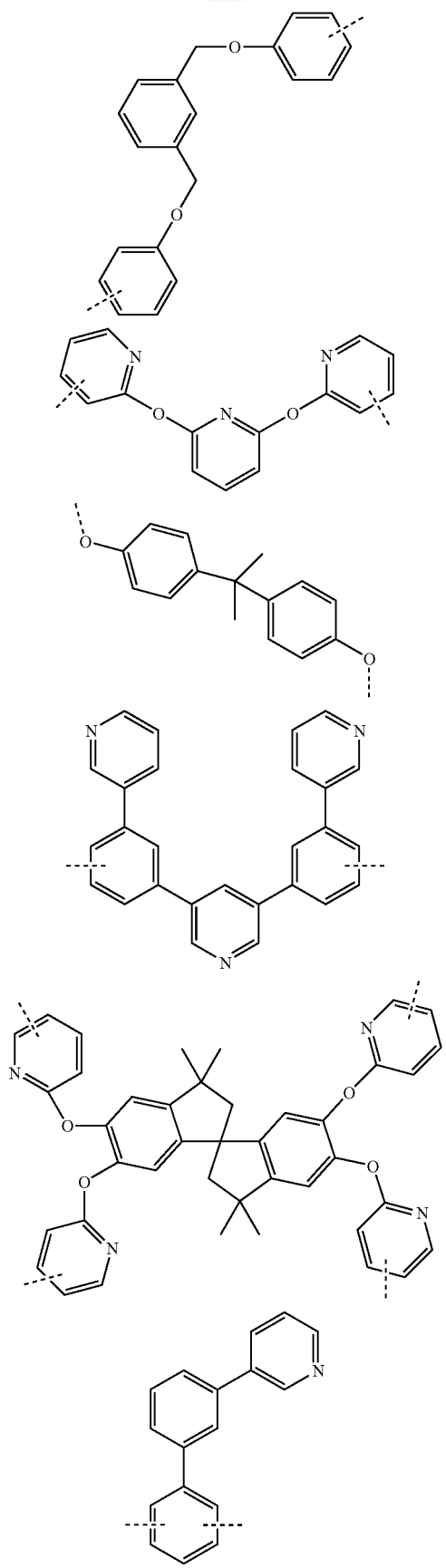
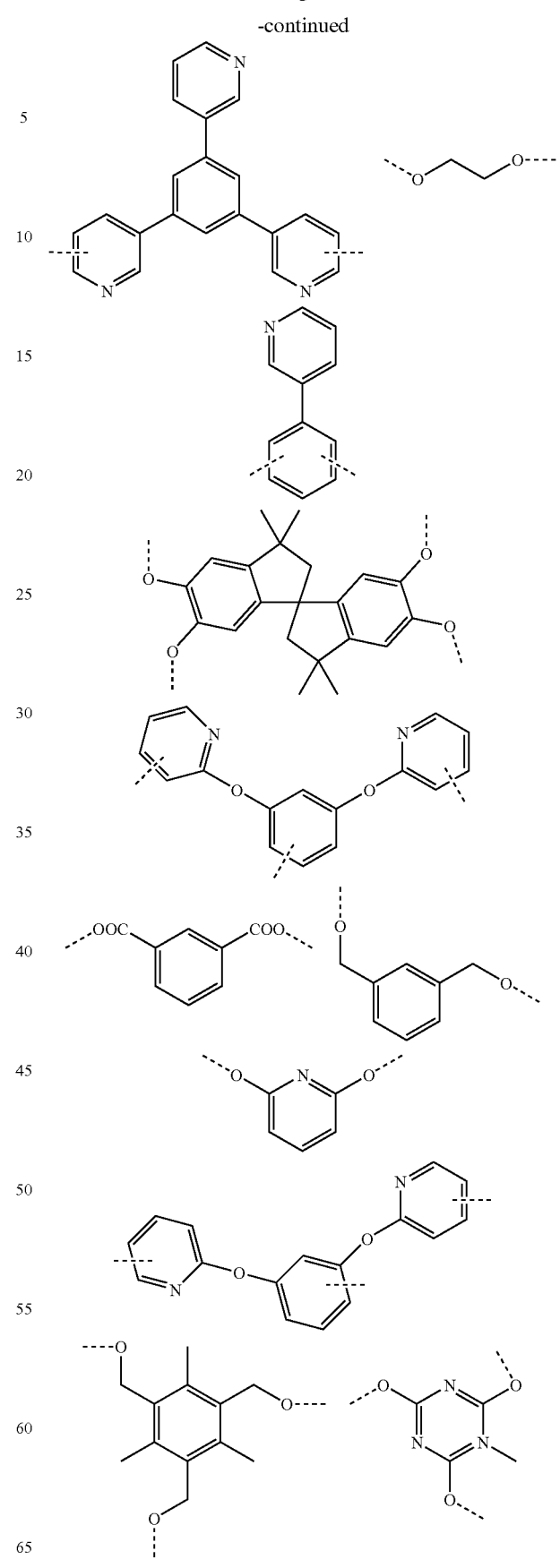

In particular embodiments, Ar² is independently chosen from
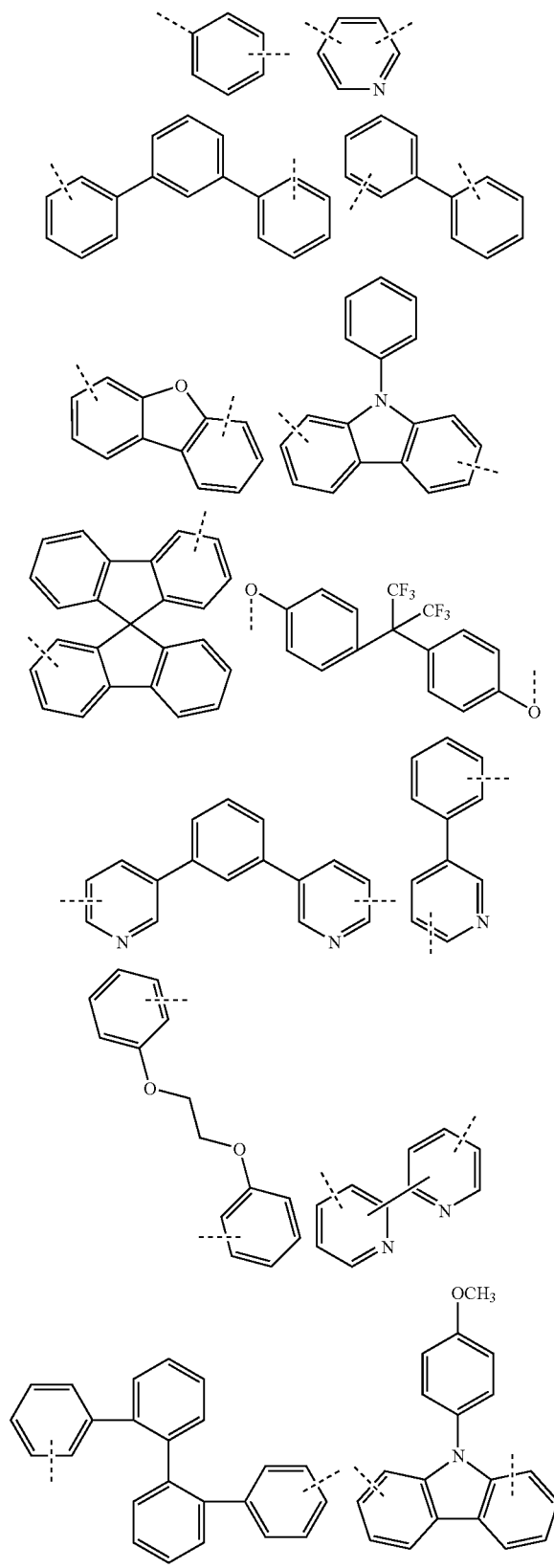
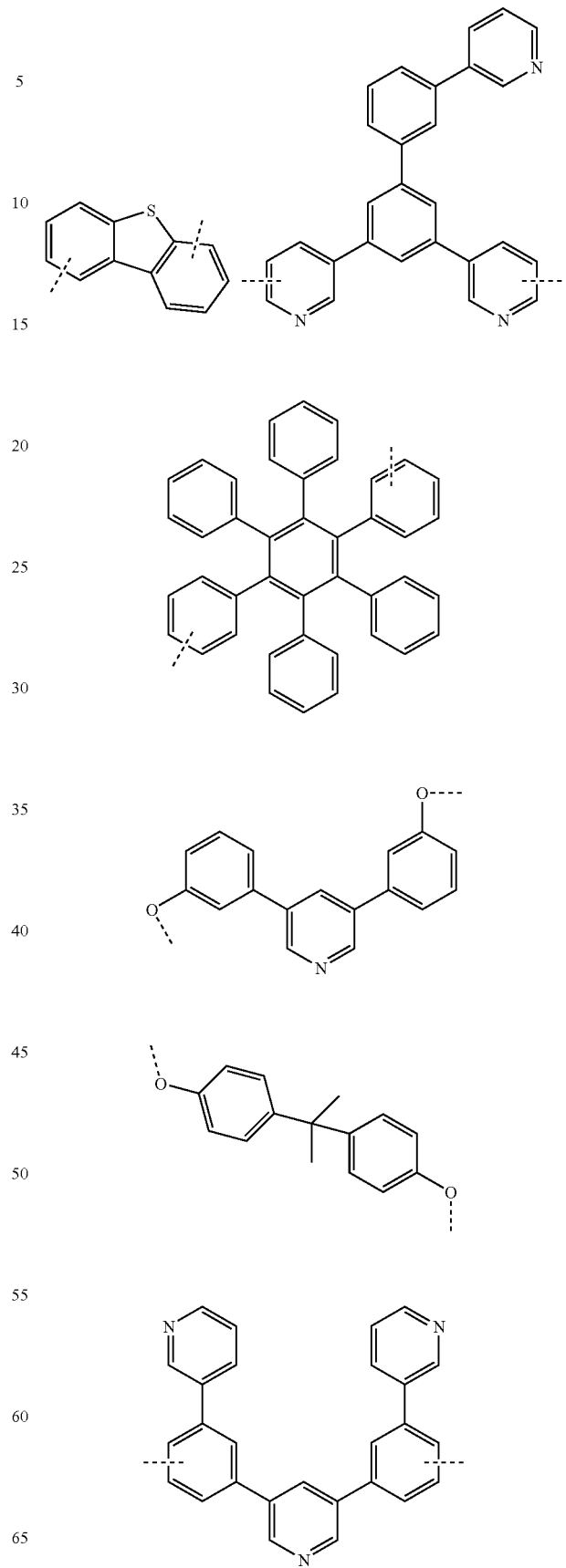

-continued
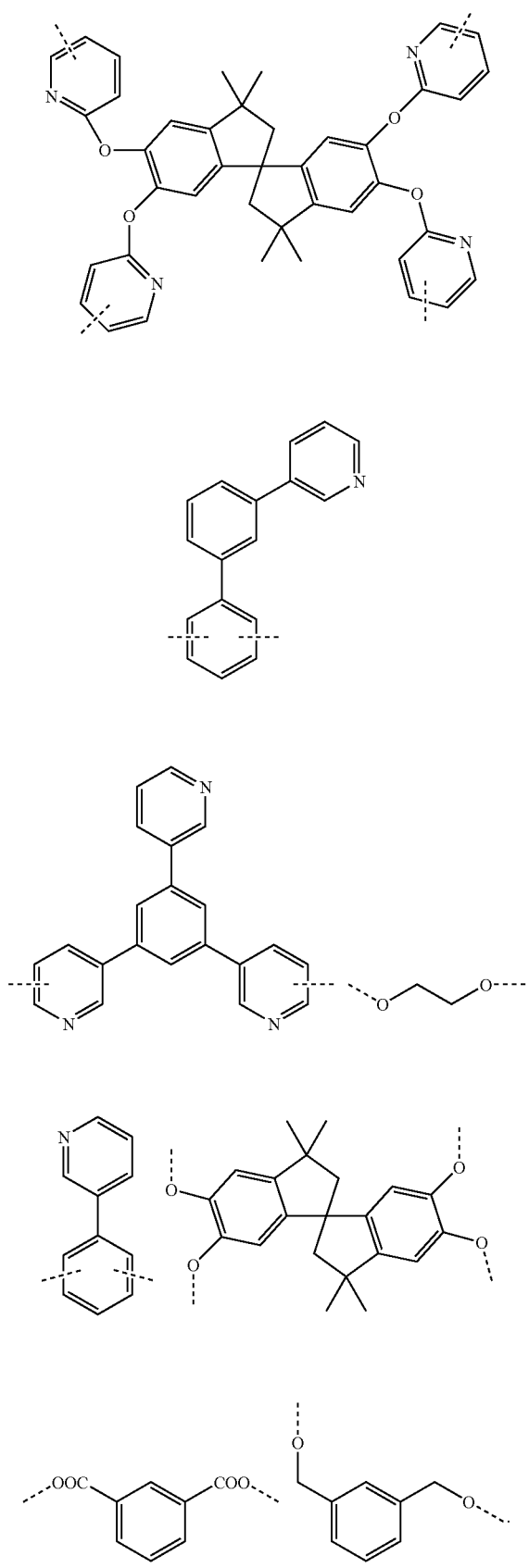
In more particular embodiments, Ar² is independently chosen from
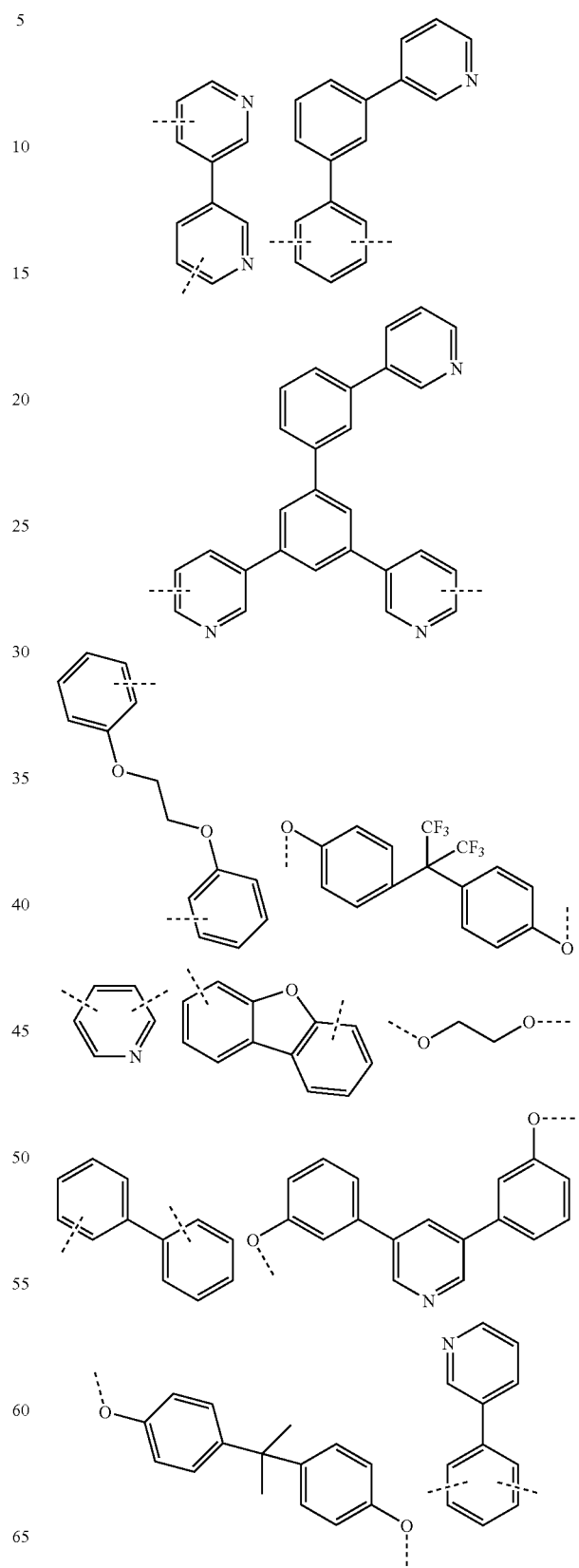

13
-continued
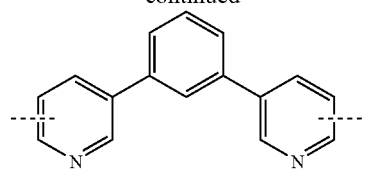
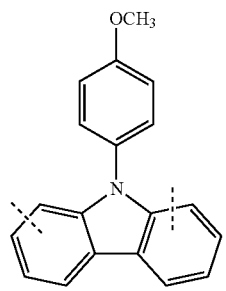
14
-continued
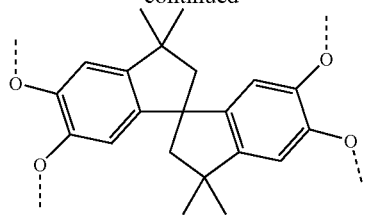
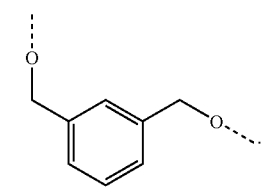
Examples of the organic compounds of formula I, II, VIII, IX and X include:
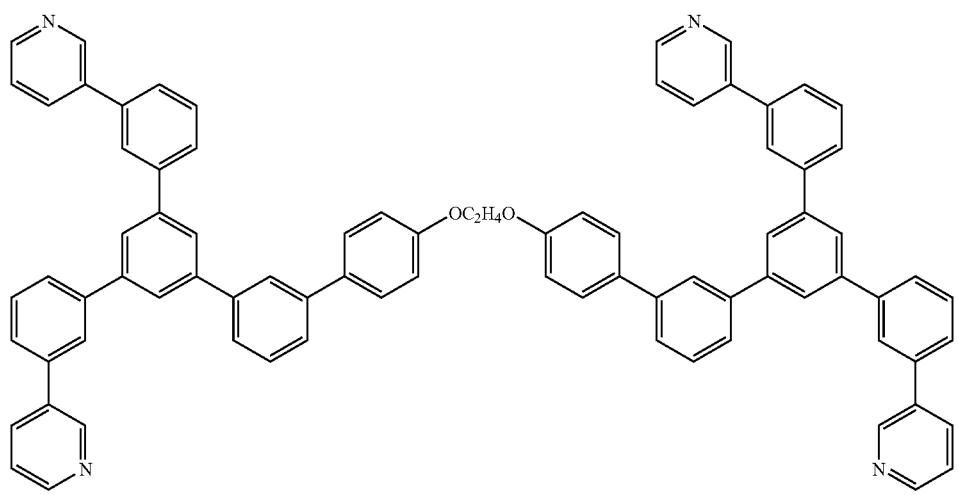
1
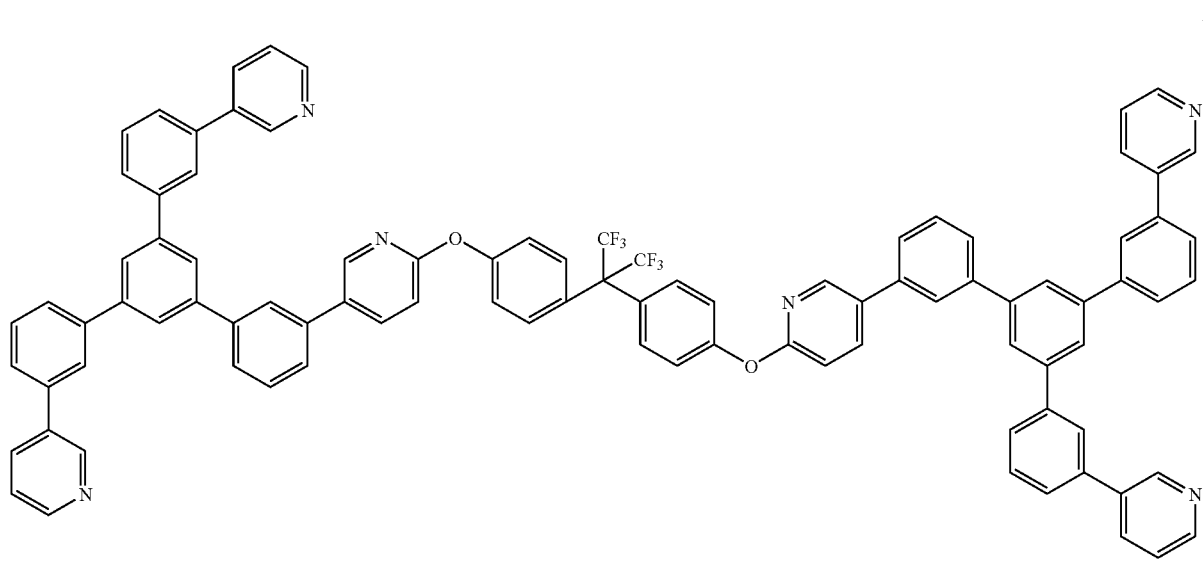
2

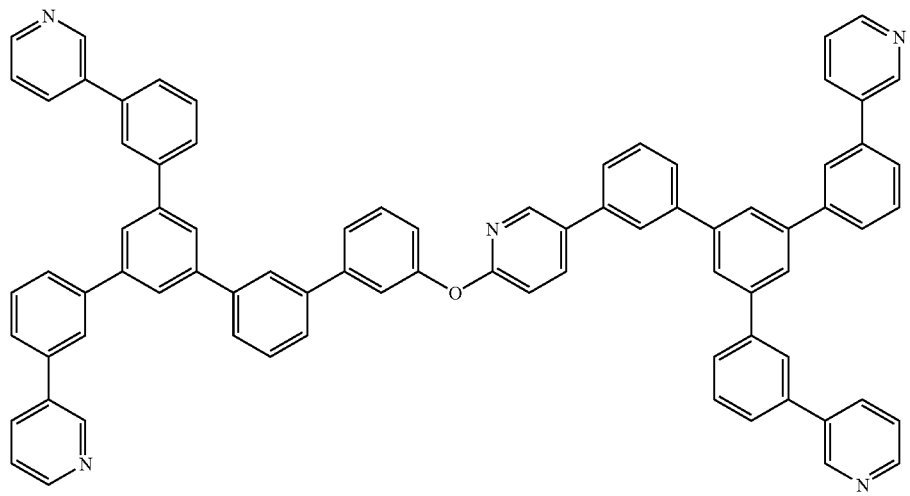
3
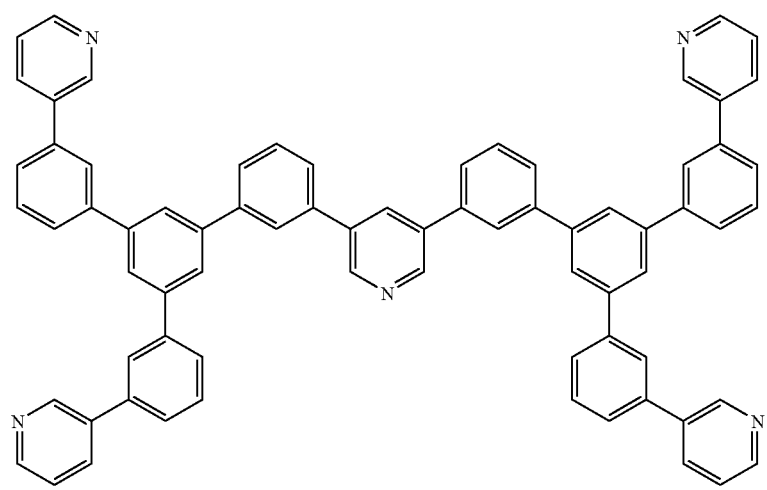
4
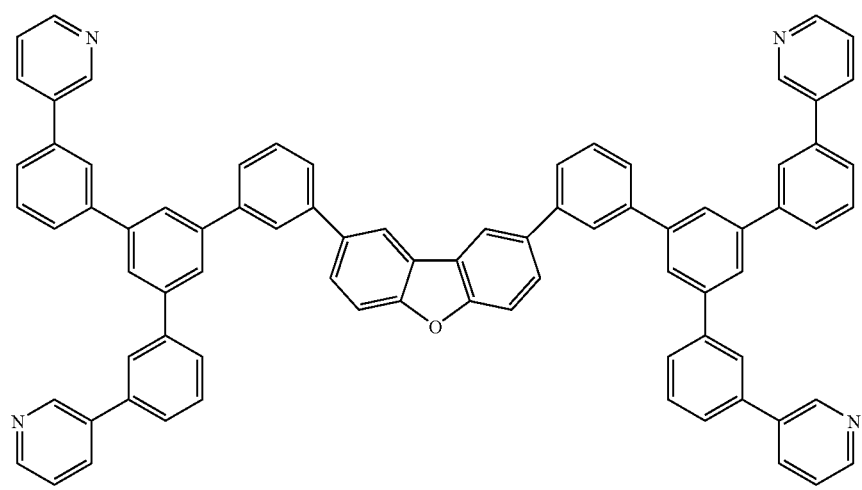
5

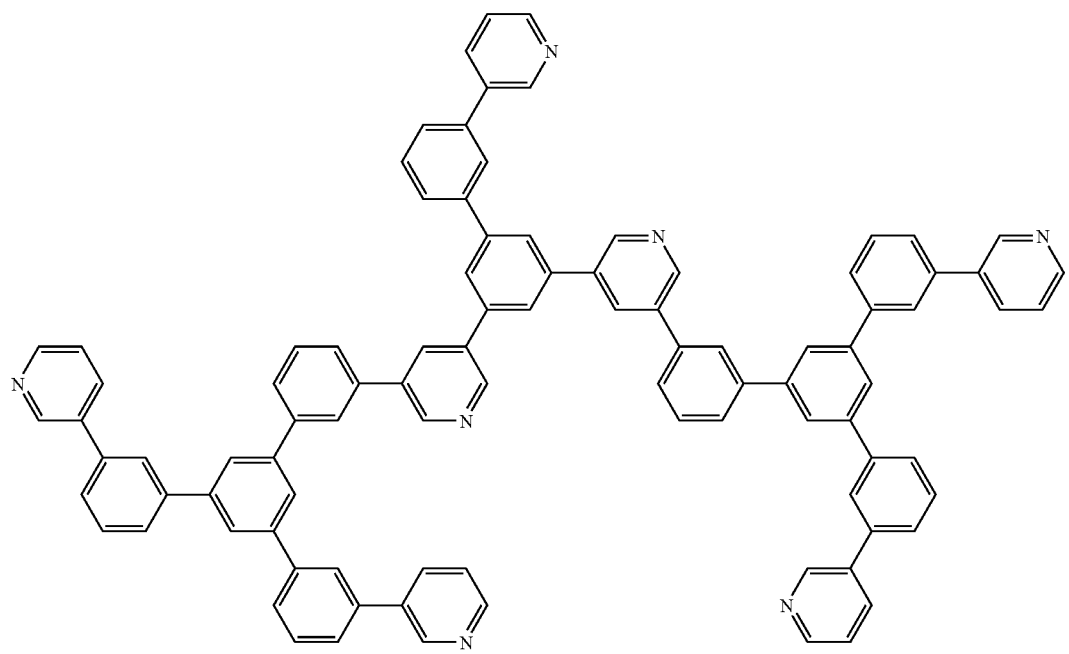
6
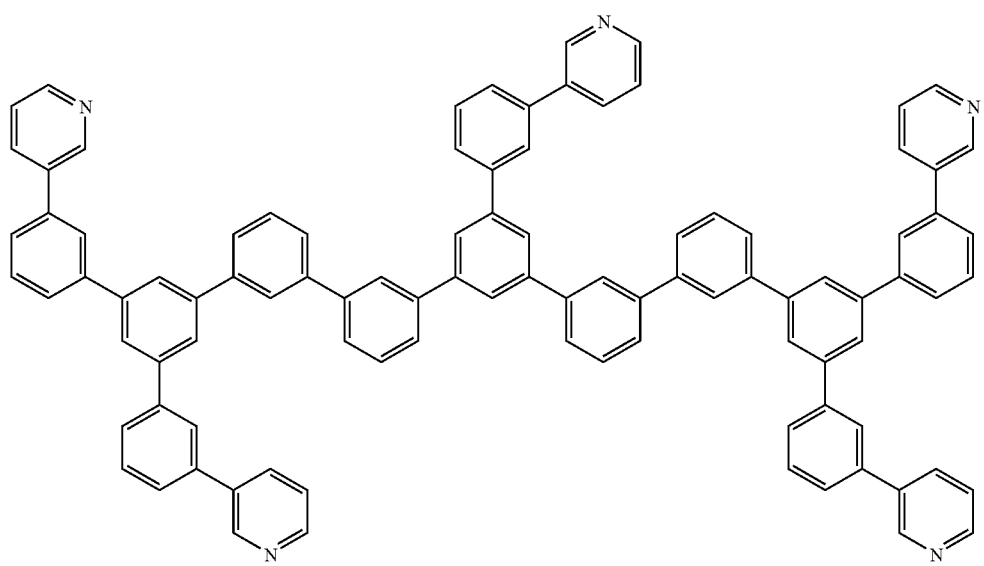
7
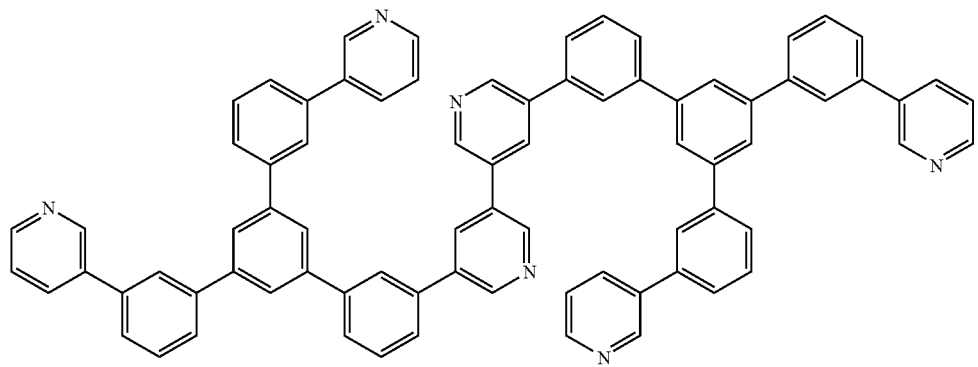
8

-continued
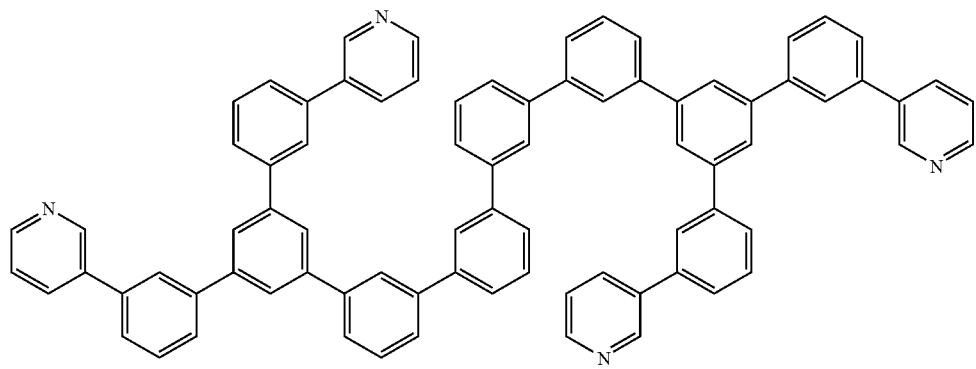
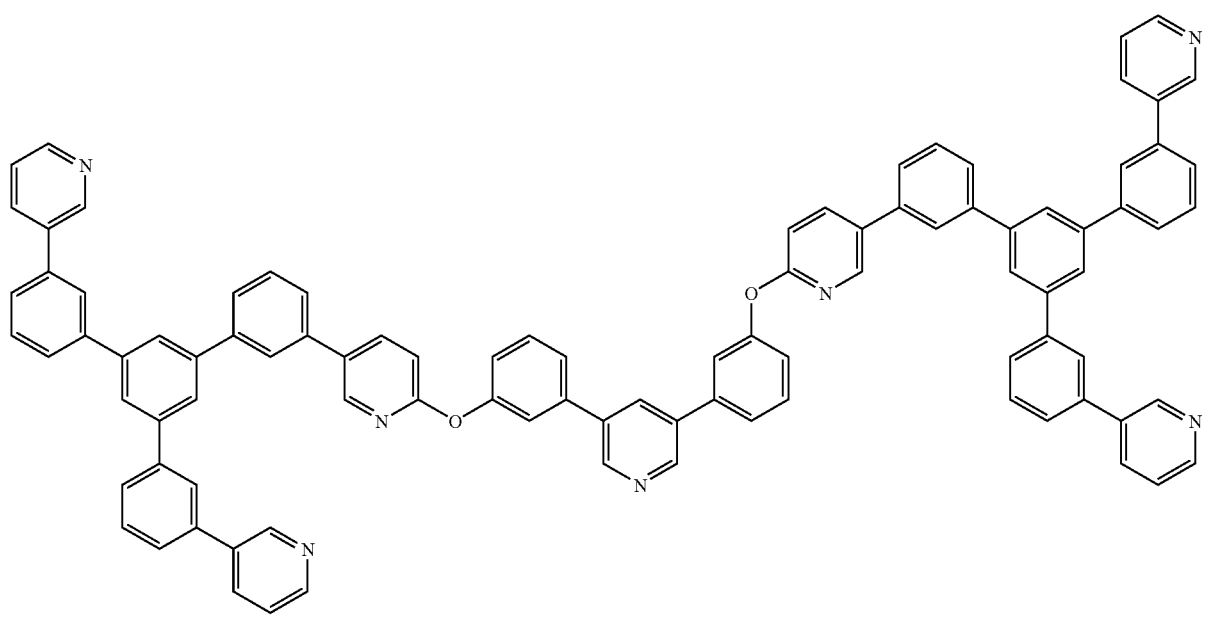
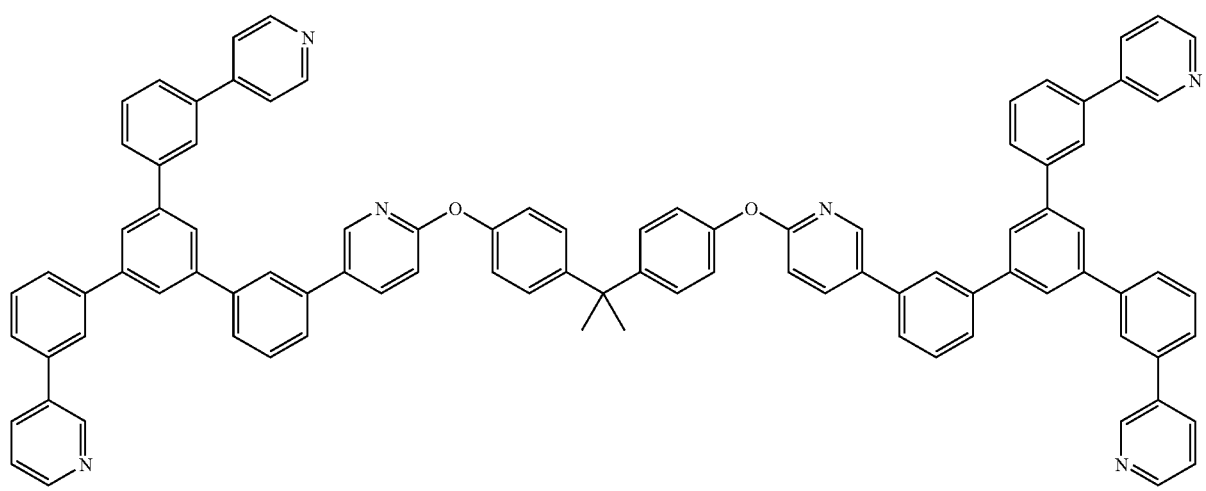

-continued
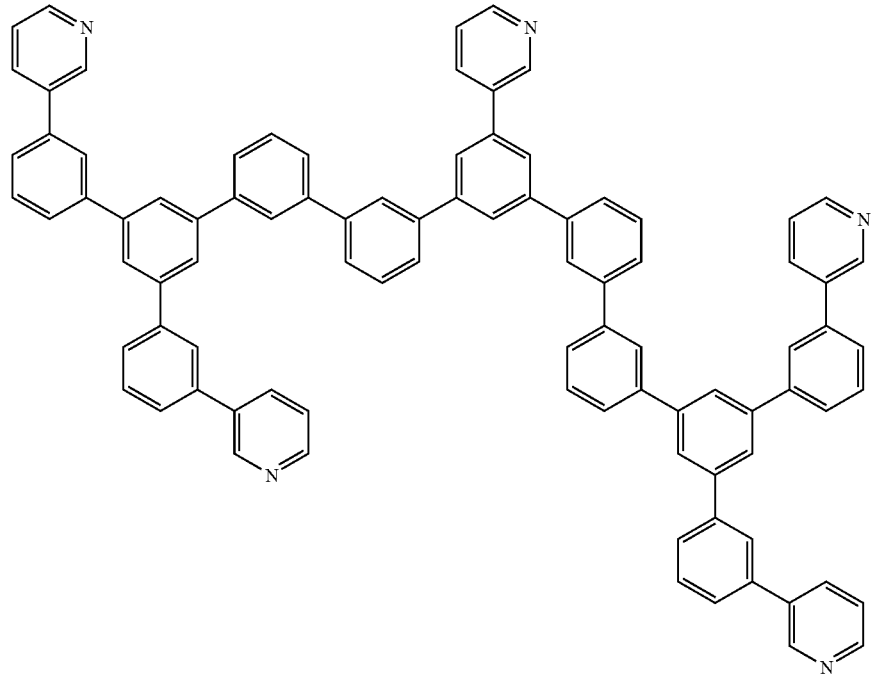
12
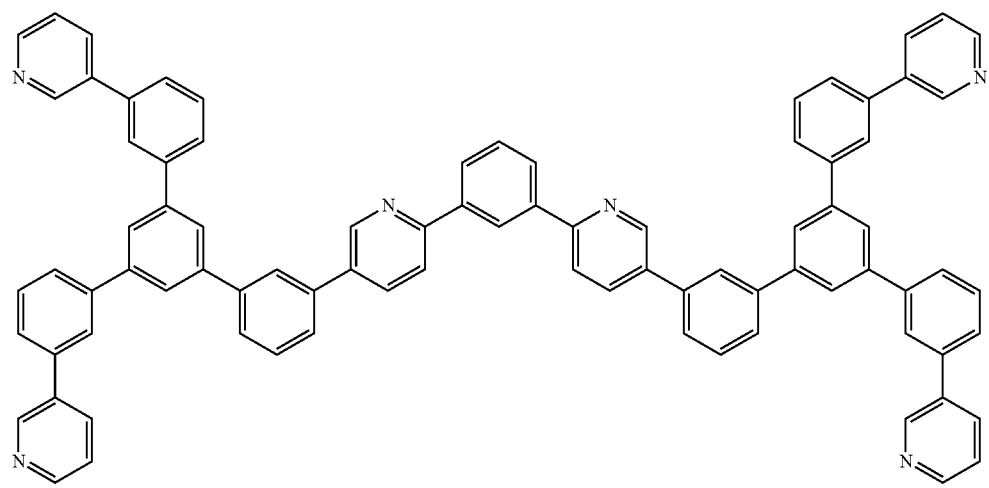
13

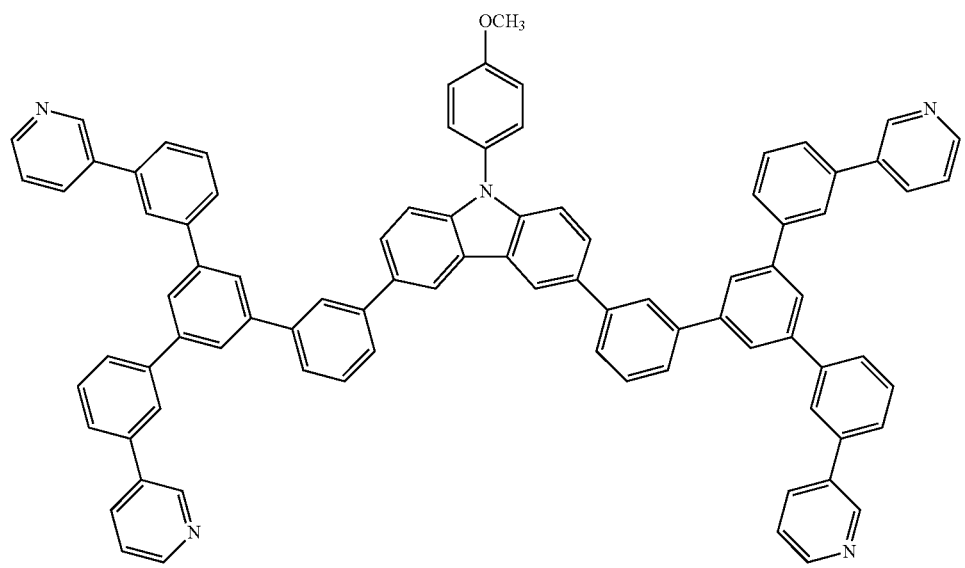
14
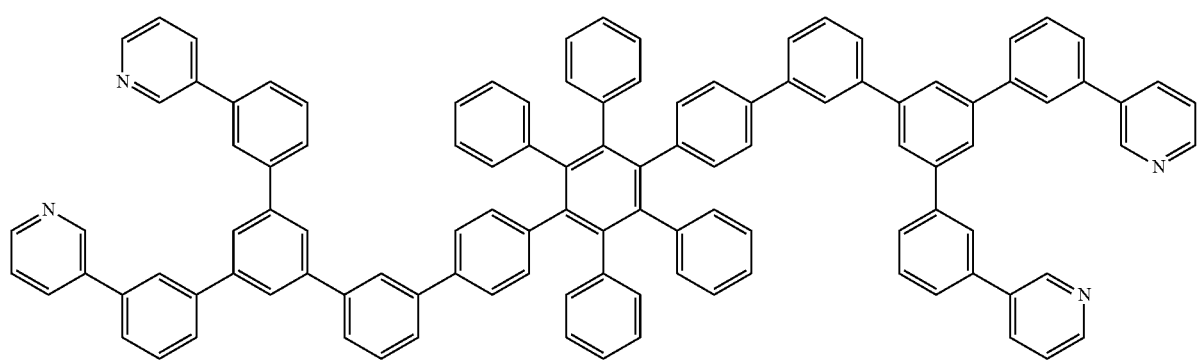
15
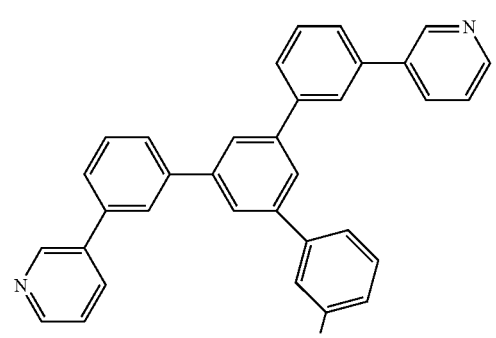
16

-continued
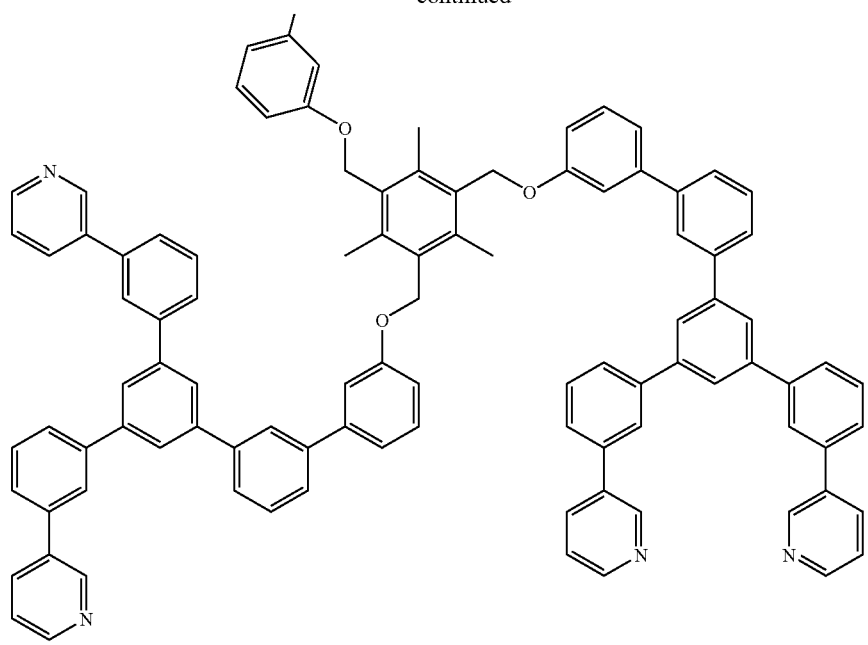
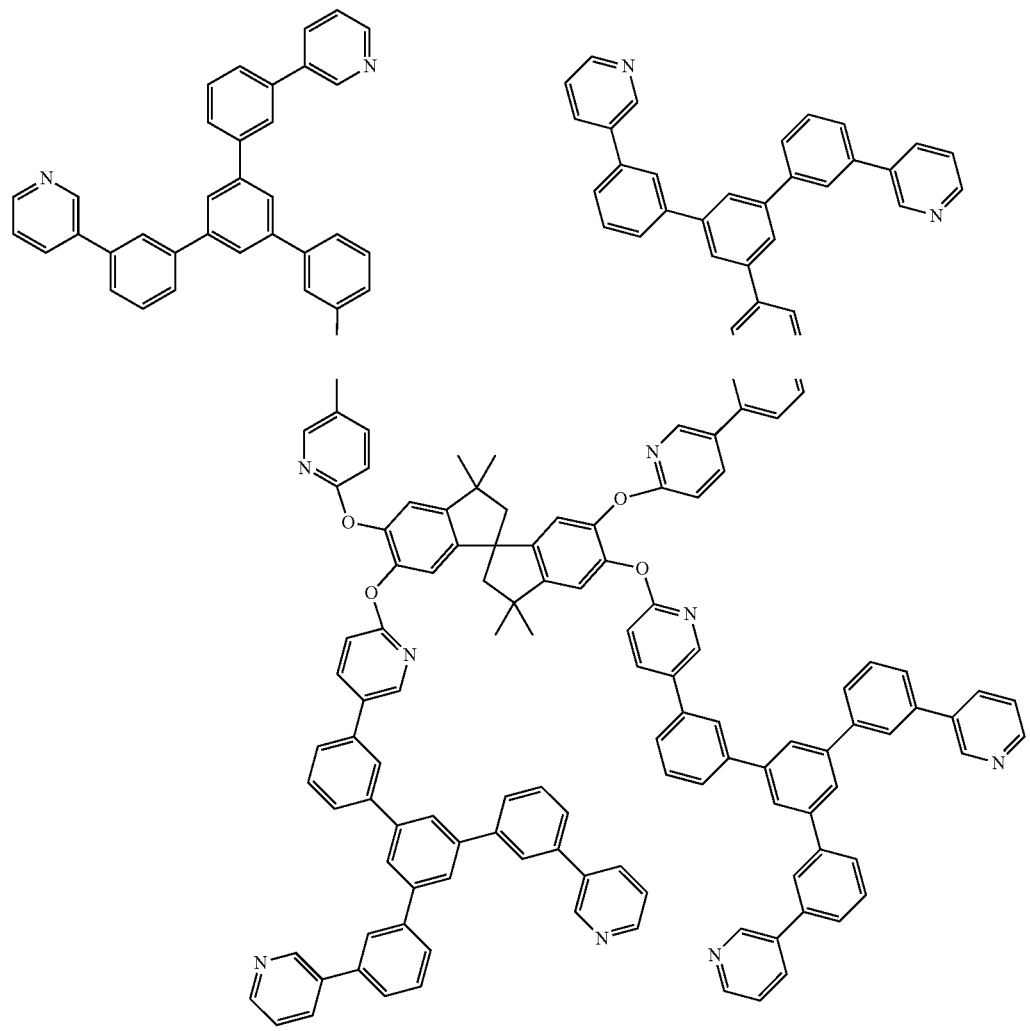

-continued
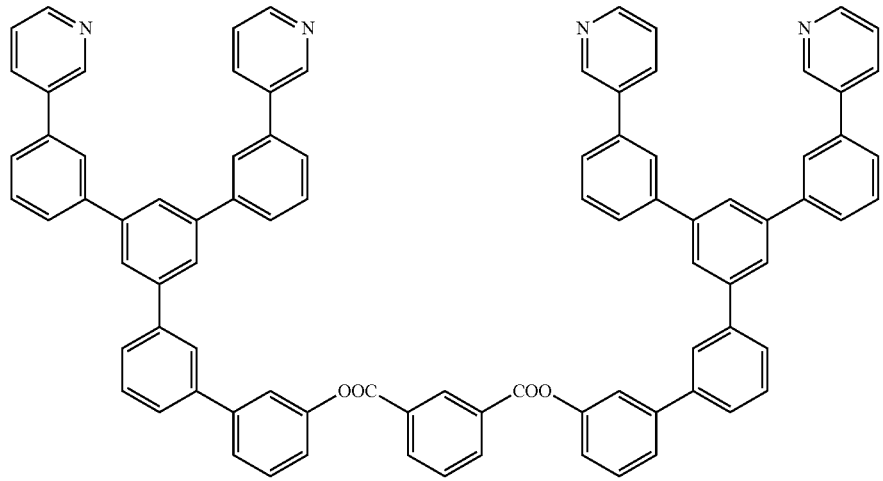
18
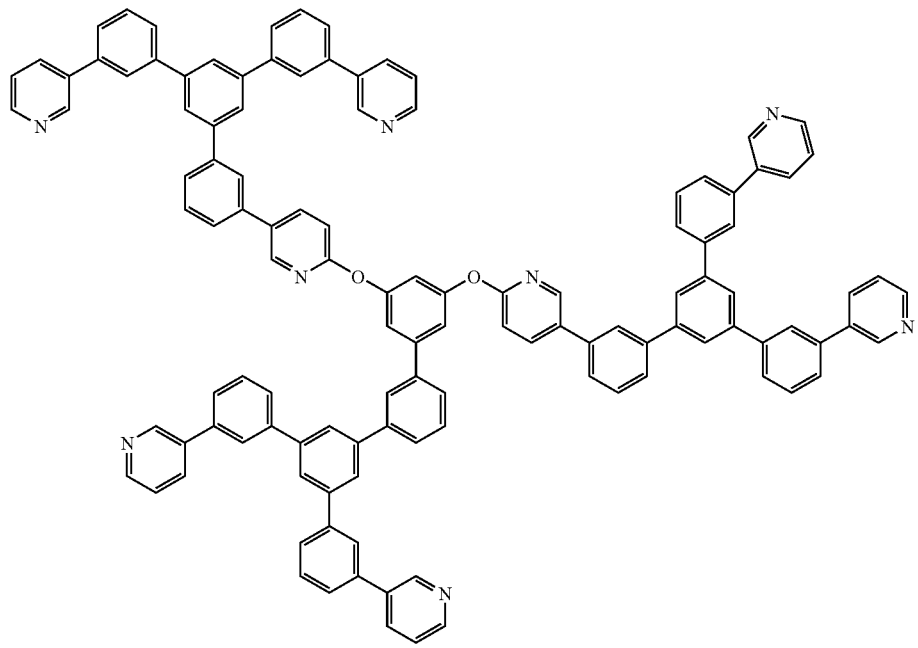
19
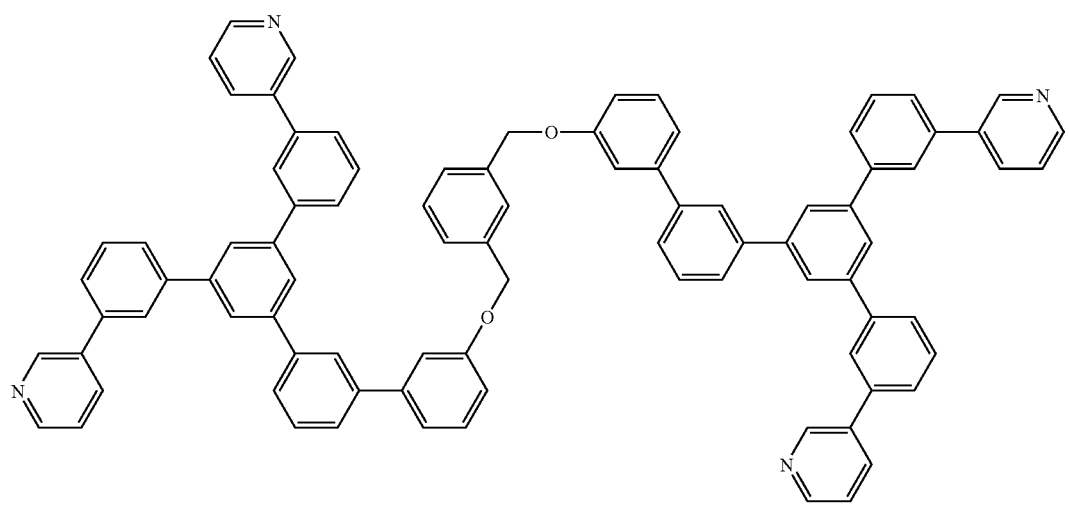
20

-continued
21
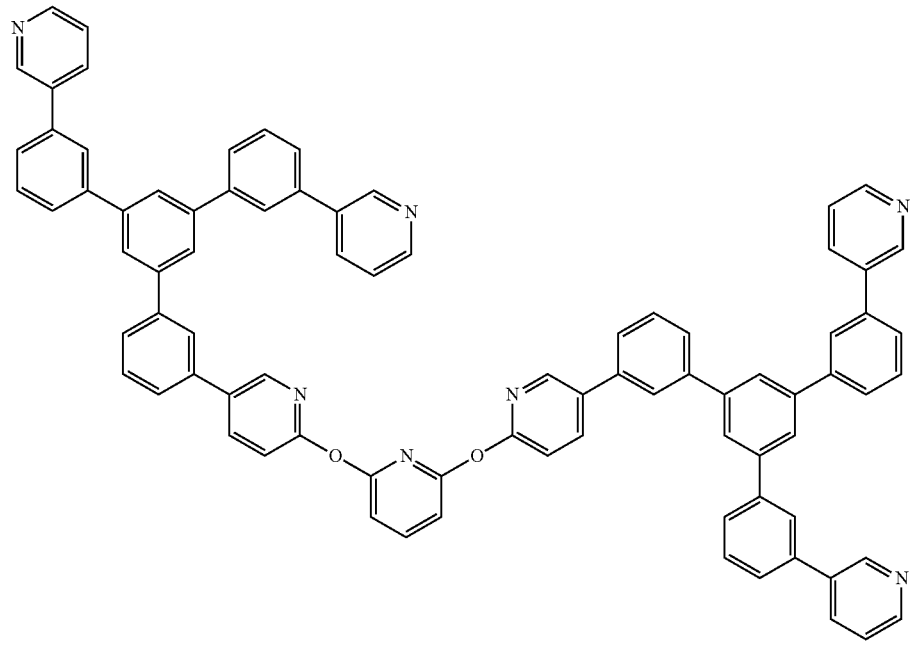
22
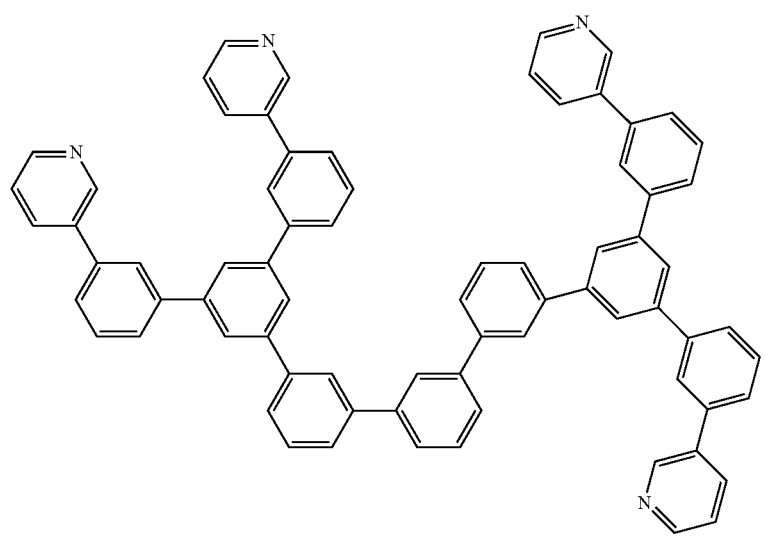
23
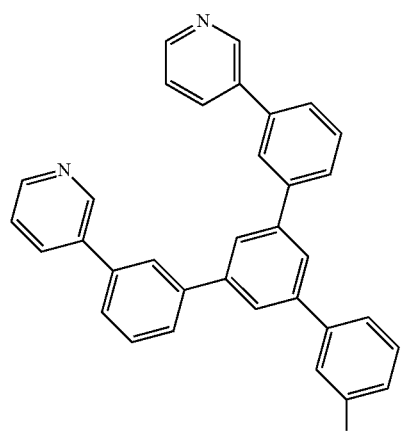

-continued
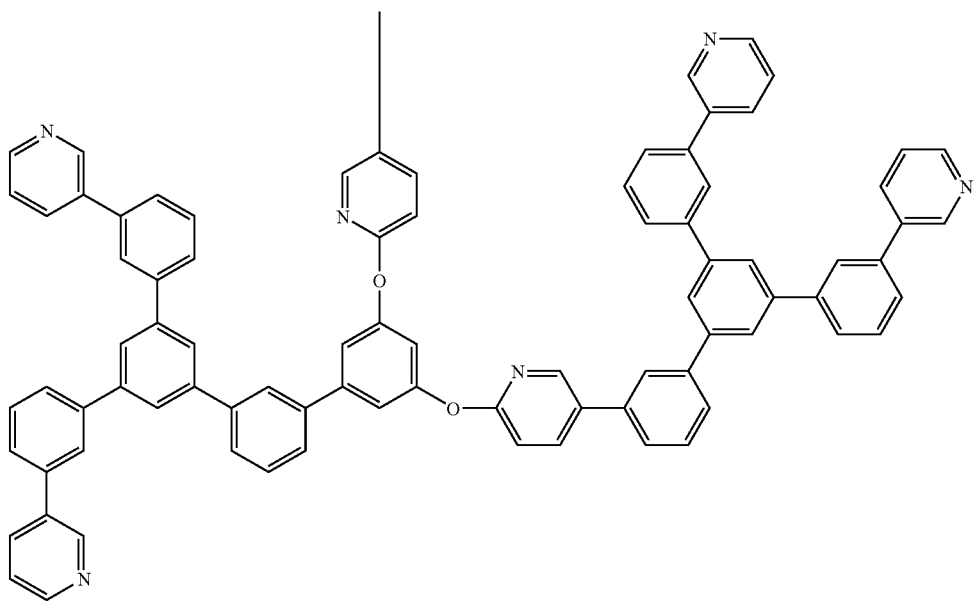
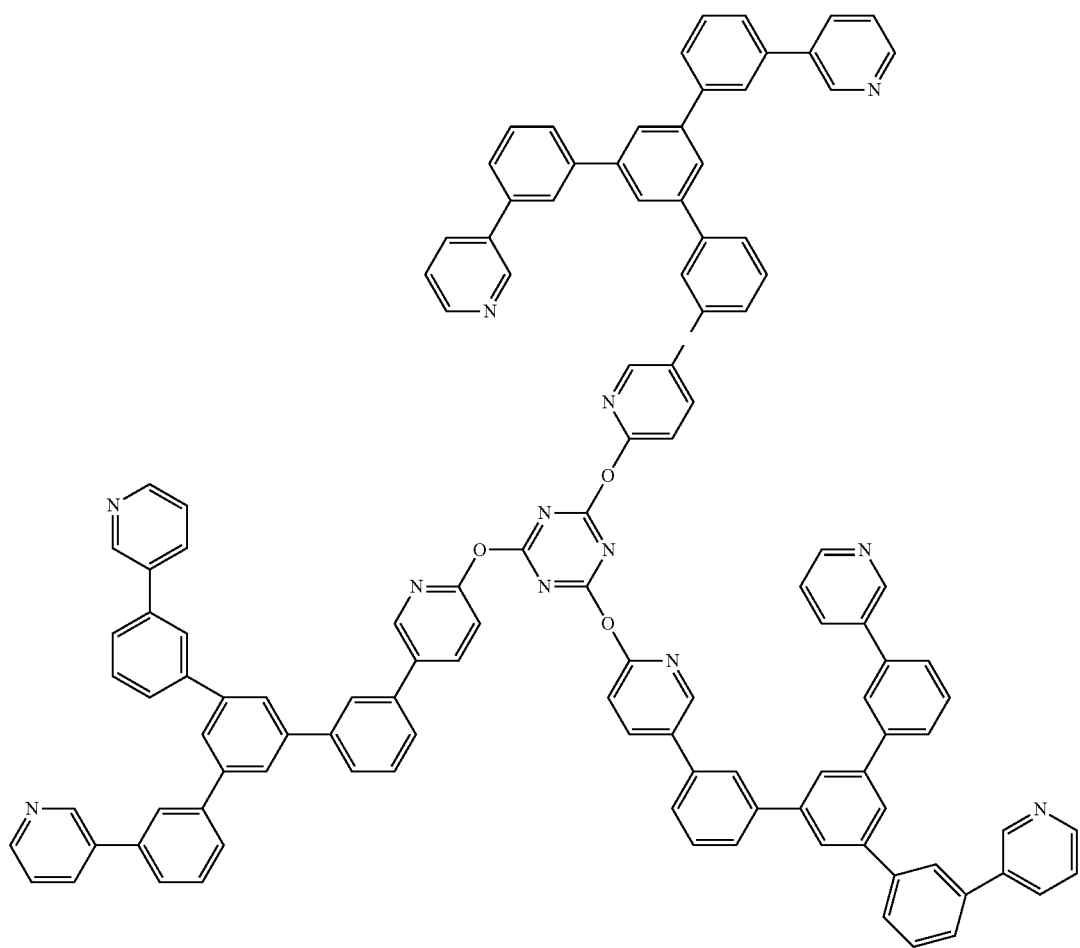

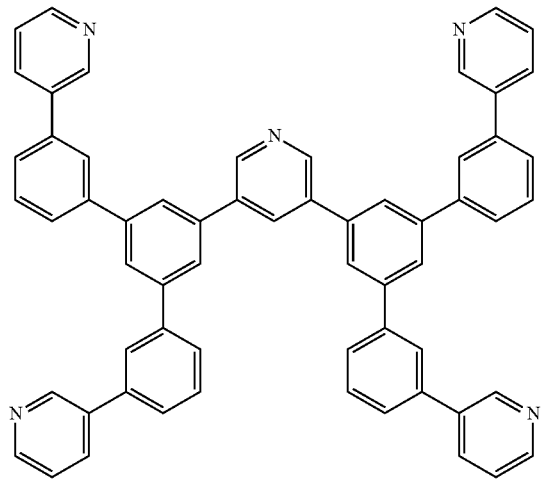
In particular embodiments, the organic compounds of formulas I, II, VIII, IX and X are chosen from
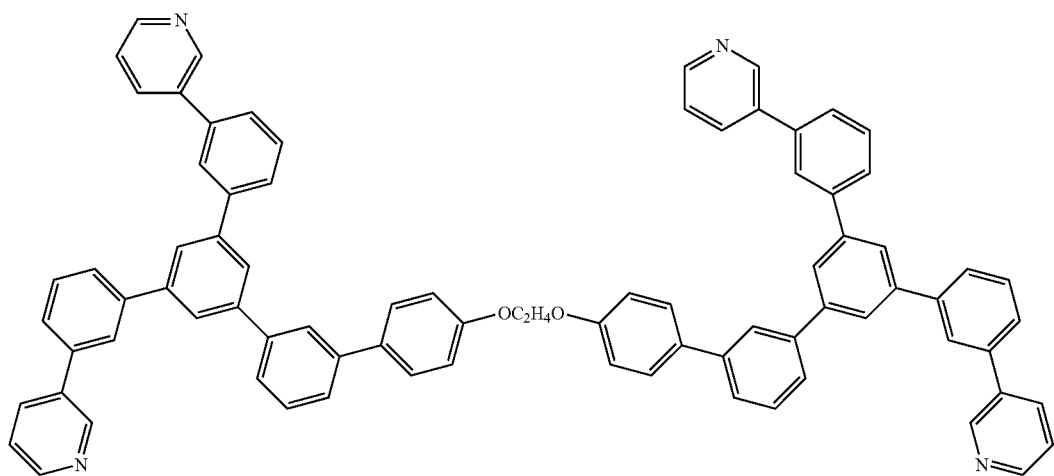
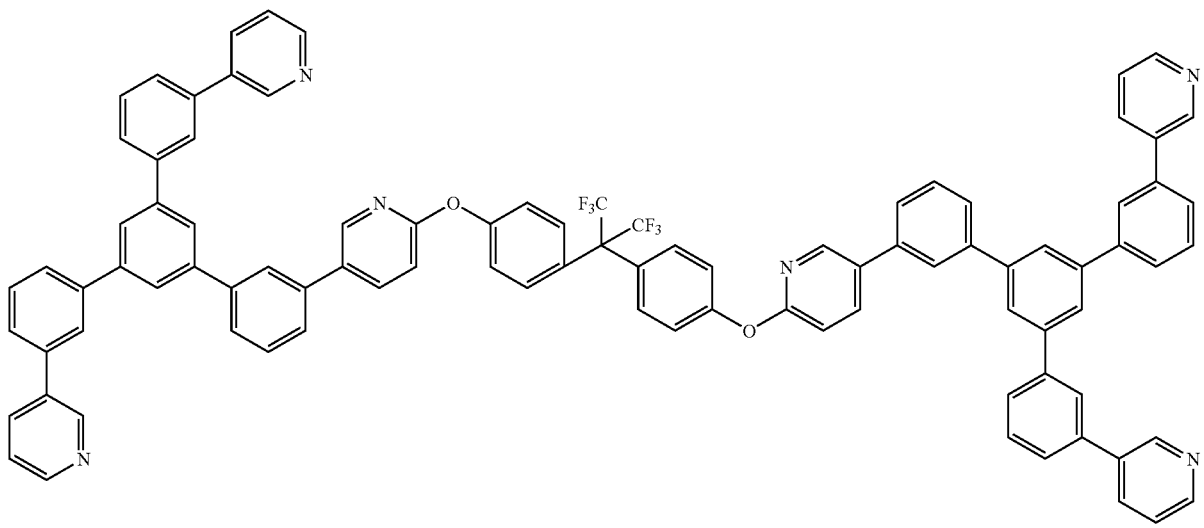

-continued
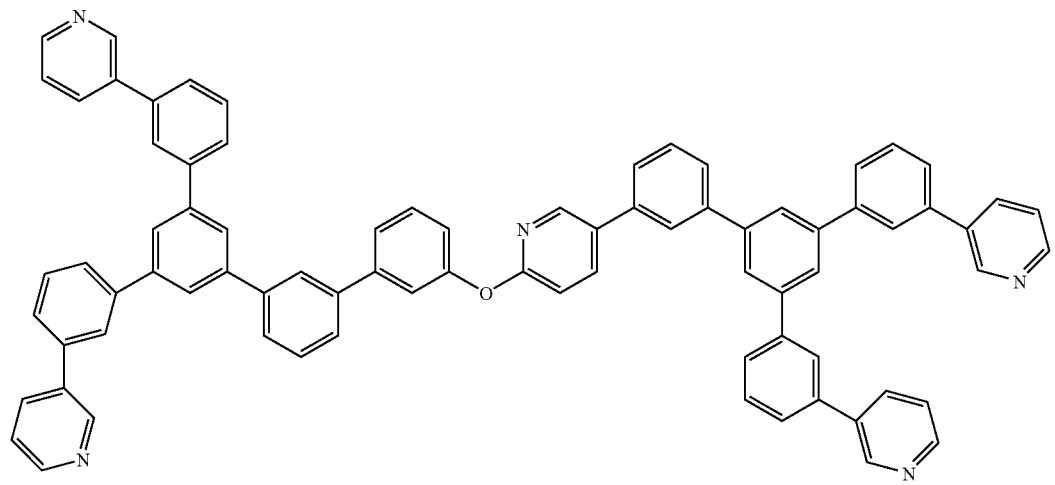
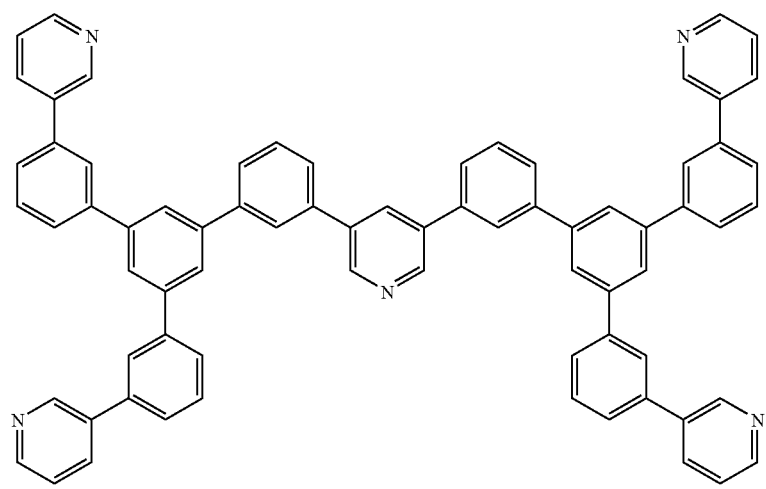
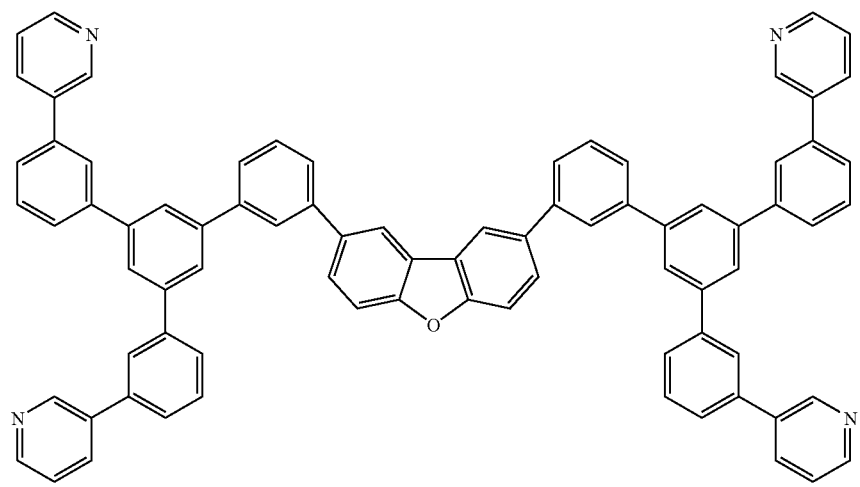

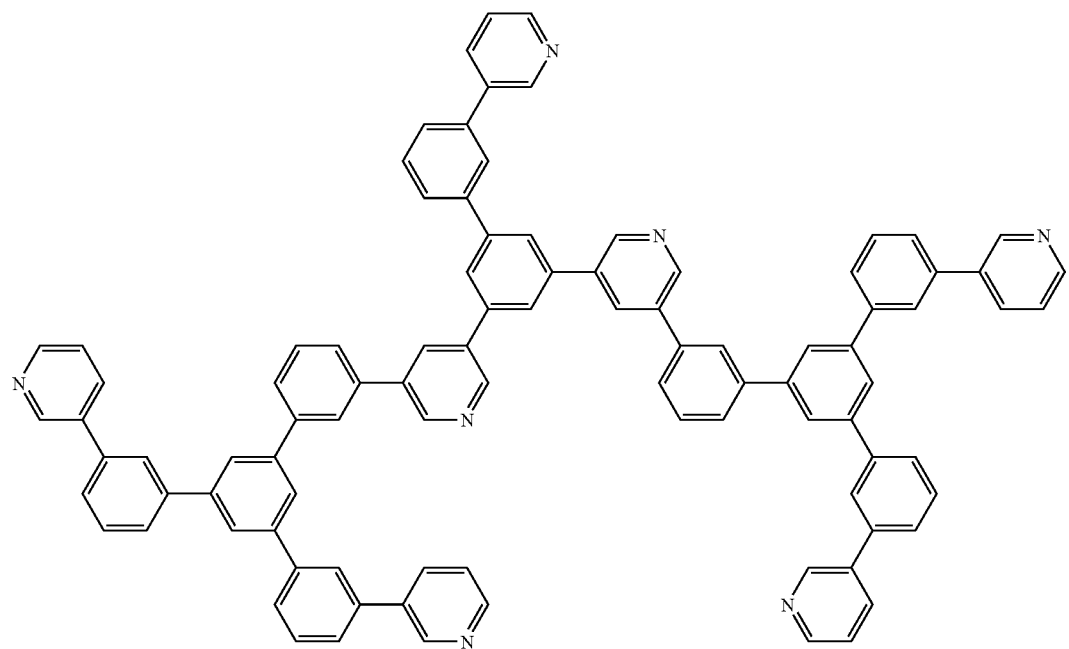
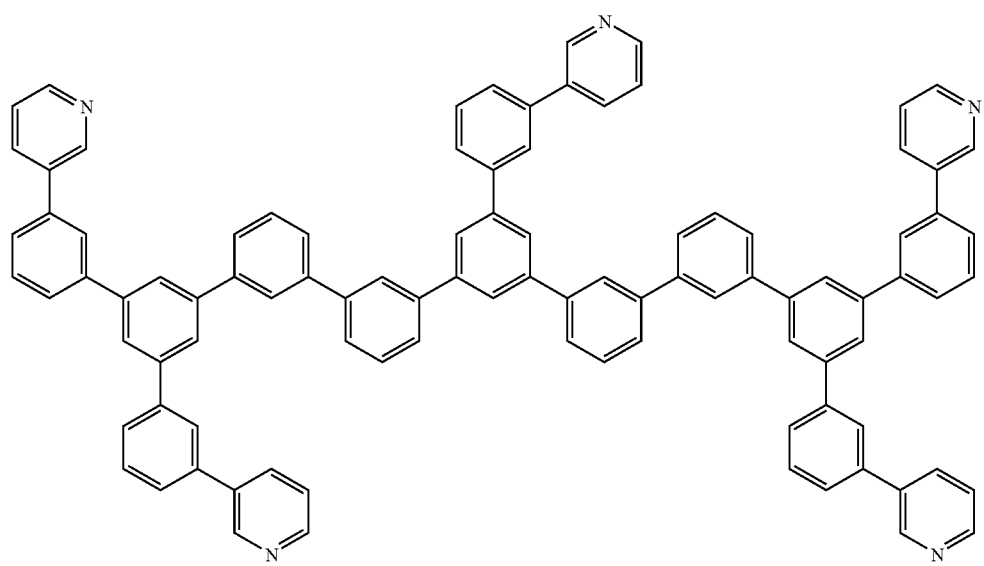

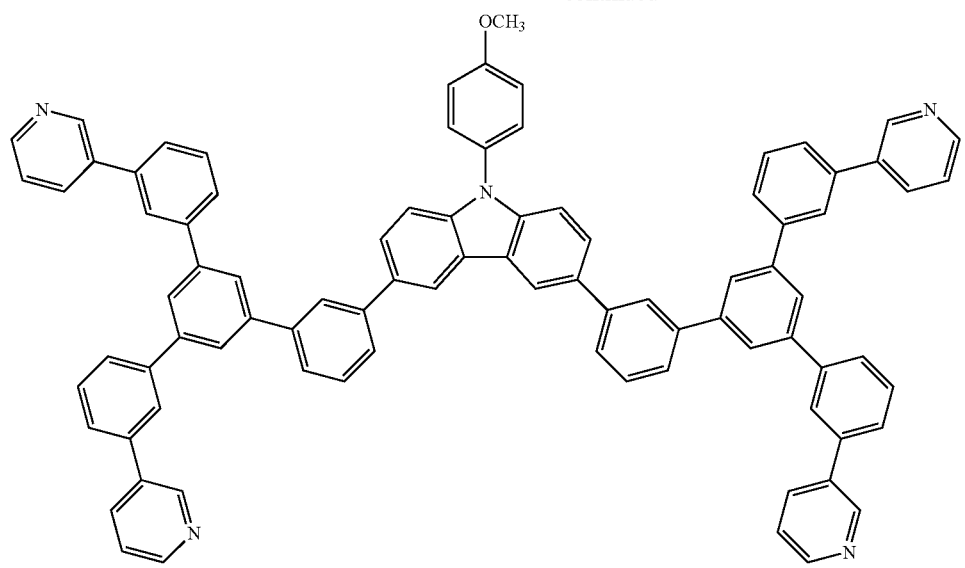
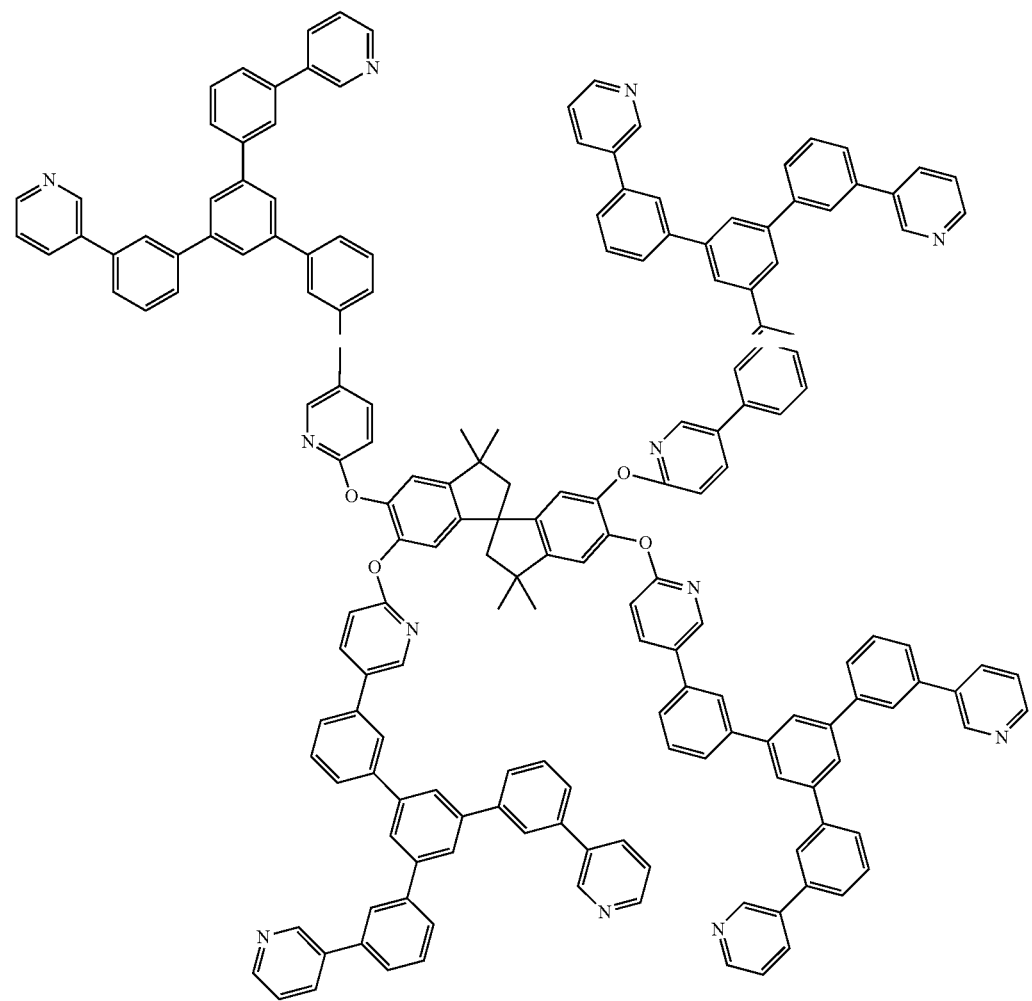

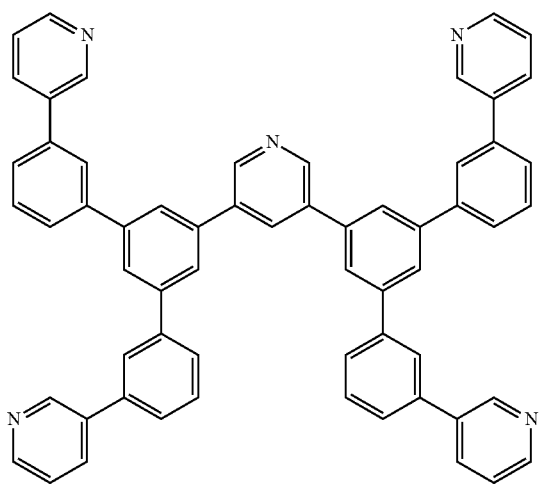

The compounds of formula I, II, VIII, IX and X may be prepared by employing Suzuki cross-coupling reactions. General procedure for Suzuki cross-coupling reactions includes mixing an aryl halide and aryl borate (or boronic acid) in a suitable solvent, in the presence of a base and Pd catalyst. The reaction mixture is heated under an inert atmosphere for a period of time. Suitable solvents include but are not limited to Dioxane, THF, EtOH, toluene and mixtures thereof. Exemplary bases include $Na_2CO_3$, $K_2CO_3$, $Cs_2CO_3$, Potassium phosphate and hydrates thereof. The bases can be added to the reaction as a solid powder or as an aqueous solution. The most commonly used catalysts include $Pd(PPh_3)_4$, or $Pd(OAc)_2$, $Pd(dba)_2$ with the addition of a secondary ligand. Exemplary ligands include dialkylphosphinobiphenyl ligands, such as structures III-VII shown below, in which Cy is cyclohexyl.

III

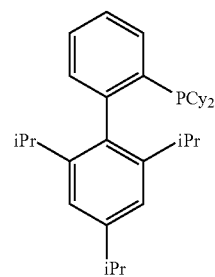

IV

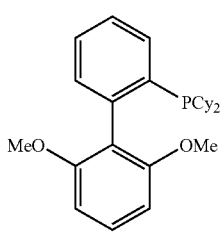

-continued

V

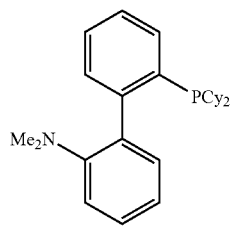

VI

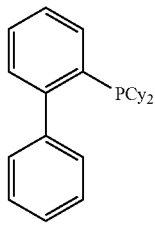

VII

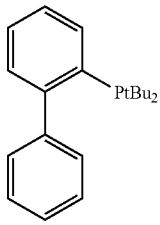

In general there are at least two methods that may be used to convert an aryl halide into its corresponding aryl borate. One method involves the generation of a carbanion using either BuLi to effect a lithio-halogen exchange or by using Mg to generate a Grignard reagent, followed by quenching of the carbanion with a borate such as trimethylborate, triethylborate or tri(isopropyl)borate and the like. A typical procedure involves combining the starting materials in dry solvents such as THF or diethylether under anhydrous and inert conditions. The reaction is cooled to −100° C. or −80° C. and BuLi is added dropwise and stirred at this temperature for a certain amount of time (1-5 hours). After which time the intermediate carbanion is quenched with a suitable borate ester. The reaction mixture is allowed to warm to room temperature (RT), and, after stirring for 30 minutes at RT, the mixture is treated with a solution of saturated NH$_4$Cl (0.5 mL) and concentrated to dryness to afford a crude product.

The second method employs Pd-catalyzed borylation. A typical procedure includes combining an aryl halide and pinacolate diborane, anhydrous base and a dialkylphosphinobiphenyl ligand under dry and inert atmospheric conditions. The flask is protected from the atmosphere and charged with anhydrous solvent. After the solution is degassed for 15-30 minutes, the reaction mixture is charged with Pd catalyst and heated at reflux for an extended period by monitoring the disappearance of the starting aryl halide. Afterwards, the reaction mixture is cooled to RT and filtered. Upon concentration, the crude reaction product is afforded. Exemplary anhydrous bases include NaHCO$_3$, KHCO$_3$, and KOAc, particularly KOAc. Exemplary ligands include dialkylphosphinobiphenyl ligands, such as structures III-VII and trans-dichlorobis(triphenylphosphine)palladium(II).

An optoelectronic device, e.g., an OLED, typically includes in the simplest case, an anode layer and a corresponding cathode layer with an organic electroluminescent layer disposed between said anode and said cathode. When a voltage bias is applied across the electrodes, electrons are injected by the cathode into the electroluminescent layer while electrons are removed from (or "holes" are "injected" into) the electroluminescent layer from the anode. Light emission occurs as holes combine with electrons within the electroluminescent layer to form singlet or triplet excitons, light emission occurring as singlet and/or triplet excitons decay to their ground states via radiative decay.

Other components which may be present in an OLED in addition to the anode, cathode and light emitting material include a hole injection layer, an electron injection layer, and an electron transport layer. The electron transport layer need not be in direct contact with the cathode, and frequently the electron transport layer also serves as a hole locking layer to prevent holes migrating toward the cathode. Additional components which may be present in an organic light-emitting device include hole transporting layers, hole transporting emission (emitting) layers and electron transporting emission (emitting) layers.

In one embodiment, the OLEDs comprising the organic compounds of the invention may be a fluorescent OLED comprising a singlet emitter. In another embodiment, the OLEDs comprising the organic compounds of the invention may be a phosphorescent OLED comprising at least one triplet emitter. In another embodiment, the OLEDs comprising the organic compounds of the invention comprise at least one singlet emitter and at least one triplet emitter. The OLEDs comprising the organic compounds of the invention may contain one or more, any or a combination of blue, yellow, orange, red phosphorescent dyes, including complexes of transition metals such as Ir, Os and Pt. In particular, electrophosphorescent and electrofluorescent metal complexes, such as those supplied by American Dye Source, Inc., Quebec, Canada may be used. Organic compounds of the formula I and II may be part of an emissive layer, or hole transporting layer or electron transporting layer, or electron injection layer of an OLED or any combination thereof.

The organic electroluminescent layer, i.e., the emissive layer, is a layer within an organic light emitting device which when in operation contains a significant concentration of both electrons and holes and provides sites for exciton formation and light emission. A hole injection layer is a layer in contact with the anode which promotes the injection of holes from the anode into the interior layers of the OLED; and an electron injection layer is a layer in contact with the cathode that promotes the injection of electrons from the cathode into the OLED; an electron transport layer is a layer which facilitates conduction of electrons from the cathode and/or the electron injection layer to a charge recombination site. During operation of an organic light emitting device comprising an electron transport layer, the majority of charge carriers (i.e. holes and electrons) present in the electron transport layer are electrons and light emission can occur through recombination of holes and electrons present in the emissive layer. A hole transporting layer is a layer which when the OLED is in operation facilitates conduction of holes from the anode and/or the hole injection layer to charge recombination sites and which need not be in direct contact with the anode. A hole transporting emission layer is a layer in which when the OLED is in operation facilitates the conduction of holes to charge recombination sites, and in which the majority of charge carriers are holes, and in which emission occurs not only through recombination with residual electrons, but also through the transfer of energy from a charge recombination zone elsewhere in the device. An electron transporting emission layer is a layer in which when the OLED is in operation facilitates the conduction of electrons to charge recombination sites, and in which the majority of charge carriers are electrons, and in which emission occurs not only through recombination with residual holes, but also through the transfer of energy from a charge recombination zone elsewhere in the device.

Materials suitable for use as the anode includes materials having a bulk conductivity of preferred about 1000 ohms per square, as measured by a four-point probe technique. Indium tin oxide (ITO) is frequently used as the anode because it is substantially transparent to light transmission and thus facilitates the escape of light emitted from electro-active organic layer. Other materials, which may be utilized as the anode layer, include tin oxide, indium oxide, zinc oxide, indium zinc oxide, zinc indium tin oxide, antimony oxide, and mixtures thereof.

Materials suitable for use as the cathode include general electrical conductors including, but not limited to metals and metal oxides such as ITO etc. which can inject negative charge carriers (electrons) into the inner layer(s) of the OLED. Various metals suitable for use as the cathode include K, Li, Na, Cs, Mg, Ca, Sr, Ba, Al, Ag, Au, In, Sn, Zn, Zr, Sc, Y, elements of the lanthanide series, alloys thereof, and mixtures thereof. Suitable alloy materials for use as the cathode layer include Ag—Mg, Al—Li, In—Mg, Al—Ca, and Al—Au alloys. Layered non-alloy structures may also be employed in the cathode, such as a thin layer of a metal such as calcium, or a metal fluoride, such as LiF, covered by a thicker layer of a metal, such as aluminum or silver. In particular, the cathode may be composed of a single metal, and especially of aluminum metal.

Organic compounds of formula I, II, VIII, IX and X may be used in electron transport layers in place of, or in addition to traditional materials such as poly(9,9-dioctyl fluorene), tris (8-hydroxyquinolato) aluminum (Alq$_3$), 2,9-dimethyl-4,7-diphenyl-1,1-phenanthroline, 4,7-diphenyl-1,10-phenanthroline, 2-(4-biphenylyl)-5-(4-t-butylphenyl)-1,3,4-oxadiazole, 3-(4-biphenylyl)-4-phenyl-5-(4-t-butylphenyl)-1,2,4-triazole, 1,3,4-oxadiazole-containing polymers, 1,3,4-triazole-containing polymers, quinoxaline-containing polymers, and cyano-PPV.

Materials suitable for use in hole transporting layers include 1,1-bis((di-4-tolylamino)phenyl)cyclohexane, N,N'-bis(4-methylphenyl)-N,N'-bis(4-ethylphenyl)-(1,1'-(3,3'-dimethyl)biphenyl)-4,4'-diamine, tetrakis-(3-methylphenyl)-N,N,N',N'-2,5-phenylenediamine, phenyl-4-N,N-diphenylaminostyrene, p-(diethylamino) benzaldehyde diphenylhydrazone, triphenylamine, 1-phenyl-3-(p-(diethylamino)styryl)-5-(p-(diethylamino)phenyl)pyrazoline, 1,2-trans-bis(9H-carbazol-9-yl)cyclobutane, N,N,N',N'-tetrakis (4-methylphenyl)-(1,1'-biphenyl)-4,4'-diamine, copper phthalocyanine, polyvinylcarbazole, (phenylmethyl)polysilane; poly(3,4-ethylendioxythiophene) (PEDOT), polyaniline, polyvinylcarbazole, triaryldiamine, tetraphenyldiamine, aromatic tertiary amines, hydrazone derivatives, carbazole derivatives, triazole derivatives, imidazole derivatives, oxadiazole derivatives having an amino group, and polythiophenes as disclosed in U.S. Pat. No. 6,023,371.

Materials suitable for use in the light emitting layer include electroluminescent polymers such as polyfluorenes, preferably poly(9,9-dioctyl fluorene) and copolymers thereof, such as poly(9,9'-dioctylfluorene-co-bis-N,N'-(4-butylphenyl) diphenylamine) (F8-TFB); poly(vinylcarbazole) and polyphenylenevinylene and their derivatives. In addition, the light emitting layer may include a blue, yellow, orange, green or red phosphorescent dye or metal complex, or a combination thereof. Materials suitable for use as the phosphorescent dye include, but are not limited to, tris(1-phenylisoquinoline) iridium (III) (red dye), tris(2-phenylpyridine) iridium (green dye) and Iridium (III) bis(2-(4,6-difluorephenyl)pyridinato-N,C2) (blue dye). Commercially available electrofluorescent and electrophosphorescent metal complexes from ADS (American Dyes Source, Inc.) may also be used. ADS green dyes include ADS060GE, ADS061GE, ADS063GE, and ADS066GE, ADS078GE, and ADS090GE. ADS blue dyes include ADS064BE, ADS065BE, and ADS070BE. ADS red dyes include ADS067RE, ADS068RE, ADS069RE, ADS075RE, ADS076RE, ADS067RE, and ADS077RE.

Organic compounds of formula I, II, VIII, IX and X may form part of the electron transport layer or electron injection layer or light emissive layer. Thus, in one aspect, the present invention relates to more efficient optoelectronic devices, e.g., OLEDs comprising organic compounds of formula I, II, VIII, IX and X. The OLEDs may be phosphorescent containing one or more, any or a combination of, blue, yellow, orange, red phosphorescent dyes.

DEFINITIONS

As used herein, the term "aromatic radical" refers to an array of atoms having a valence of at least one comprising at least one aromatic group. The array of atoms having a valence of at least one comprising at least one aromatic group may include heteroatoms such as nitrogen, sulfur, selenium, silicon and oxygen, or may be composed exclusively of carbon and hydrogen. As used herein, the term "aromatic radical" includes but is not limited to phenyl, pyridyl, furanyl, thienyl, naphthyl, phenylene, and biphenyl radicals. As noted, the aromatic radical contains at least one aromatic group. The aromatic group is invariably a cyclic structure having 4n+2 "delocalized" electrons where "n" is an integer equal to 1 or greater, as illustrated by phenyl groups (n=1), thienyl groups (n=1), furanyl groups (n=1), naphthyl groups (n=2), azulenyl groups (n=2), and anthraceneyl groups (n=3). The aromatic radical may also include nonaromatic components. For example, a benzyl group is an aromatic radical which comprises a phenyl ring (the aromatic group) and a methylene group (the nonaromatic component). Similarly a tetrahydronaphthyl radical is an aromatic radical comprising an aromatic group ($C_6H_3$) fused to a nonaromatic component —$(CH_2)_4$—. For convenience, the term "aromatic radical" is defined herein to encompass a wide range of functional groups such as alkyl groups, alkenyl groups, alkynyl groups, haloalkyl groups, haloaromatic groups, conjugated dienyl groups, alcohol groups, ether groups, aldehydes groups, ketone groups, carboxylic acid groups, acyl groups (for example carboxylic acid derivatives such as esters and amides), amine groups, nitro groups, and the like. For example, the 4-methylphenyl radical is a $C_7$ aromatic radical comprising a methyl group, the methyl group being a functional group which is an alkyl group. Similarly, the 2-nitrophenyl group is a $C_6$ aromatic radical comprising a nitro group, the nitro group being a functional group. Aromatic radicals include halogenated aromatic radicals such as 4-trifluoromethylphenyl, hexafluoroisopropylidenebis(4-phen-1-yloxy) (i.e., —$OPhC(CF_3)_2PhO$—), 4-chloromethylphen-1-yl, 3-trifluorovinyl-2-thienyl, 3-trichloromethylphen-1-yl (i.e., 3-$CCl_3$Ph-), 4-(3-bromoprop-1-yl)phen-1-yl (i.e., 4-Br$CH_2CH_2CH_2$Ph-), and the like. Further examples of aromatic radicals include 4-allyloxyphen-1-oxy, 4-aminophen-1-yl (i.e., 4-$H_2$NPh-), 3-aminocarbonylphen-1-yl (i.e., $NH_2$COPh-), 4-benzoylphen-1-yl, dicyanomethylidenebis(4-phen-1-yloxy) (i.e., —$OPhC(CN)_2PhO$—), 3-methylphen-1-yl, methylenebis(4-phen-1-yloxy) (i.e., —$OPhCH_2PhO$—), 2-ethylphen-1-yl, phenylethenyl, 3-formyl-2-thienyl, 2-hexyl-5-furanyl, hexamethylene-1,6-bis(4-phen-1-yloxy) (i.e., —$OPh(CH_2)_6PhO$—), 4-hydroxymethylphen-1-yl (i.e., 4-HO$CH_2$Ph-), 4-mercaptomethylphen-1-yl (i.e., 4-HS$CH_2$Ph-), 4-methylthiophen-1-yl (i.e., 4-$CH_3$SPh-), 3-methoxyphen-1-yl, 2-methoxycarbonylphen-1-yloxy (e.g. methyl salicyl), 2-nitromethylphen-1-yl (i.e., 2-$NO_2CH_2$Ph), 3-trimethylsilylphen-1-yl, 4-t-butyldimethylsilylphenl-1-yl, 4-vinylphen-1-yl, vinylidenebis (phenyl), and the like. The term "a $C_3$-$C_{10}$ aromatic radical" includes aromatic radicals containing at least three but no more than 10 carbon atoms. The aromatic radical 1-imidazolyl ($C_3H_2N_2$—) represents a $C_3$ aromatic radical. The benzyl radical ($C_7H_7$—) represents a $C_7$ aromatic radical.

As used herein the term "cycloaliphatic radical" refers to a radical having a valence of at least one, and comprising an array of atoms which is cyclic but which is not aromatic. As defined herein a "cycloaliphatic radical" does not contain an aromatic group. A "cycloaliphatic radical" may comprise one or more noncyclic components. For example, a cyclohexylmethyl group ($C_6H_{11}CH_2$—) is an cycloaliphatic radical which comprises a cyclohexyl ring (the array of atoms which is cyclic but which is not aromatic) and a methylene group (the noncyclic component). The cycloaliphatic radical may include heteroatoms such as nitrogen, sulfur, selenium, silicon and oxygen, or may be composed exclusively of carbon and hydrogen. For convenience, the term "cycloaliphatic radical" is defined herein to encompass a wide range of functional groups such as alkyl groups, alkenyl groups, alkynyl groups, haloalkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylcyclopent-1-yl radical is a $C_6$ cycloaliphatic radical comprising a methyl group, the methyl group being a functional group which is an alkyl group. Similarly, the 2-nitrocyclobut-1-yl radical is a $C_4$ cycloaliphatic radical comprising a nitro group, the nitro group being a functional group. A cycloaliphatic radical may comprise one or more halogen atoms which may be the same or different. Halogen atoms include, for example; fluorine, chlorine, bromine, and iodine. Cycloaliphatic radicals comprising one or more halogen atoms include 2-trifluoromethylcyclohex-1-yl, 4-bromodifluoromethylcyclooct-1-yl, 2-chlorodifluoromethylcyclohex-1-yl, hexafluoroisopropylidene-2,2-bis (cyclohex-4-yl) (i.e., $-C_6H_{10}C(CF_3)_2C_6H_{10}-$), 2-chloromethylcyclohex-1-yl, 3-difluoromethylenecyclohex-1-yl, 4-trichloromethylcyclohex-1-yloxy, 4-bromodichloromethylcyclohex-1-ylthio, 2-bromoethylcyclopent-1-yl, 2-bromopropylcyclohex-1-yloxy (e.g. $CH_3CHBrCH_2C_6H_{10}O-$), and the like. Further examples of cycloaliphatic radicals include 4-allyloxycyclohex-1-yl, 4-aminocyclohex-1-yl (i.e., $H_2NC_6H_{10}-$), 4-aminocarbonylcyclopent-1-yl (i.e., $NH_2COC_5H_8-$), 4-acetyloxycyclohex-1-yl, 2,2-dicyanoisopropylidenebis(cyclohex-4-yloxy) (i.e., $-OC_6H_{10}C(CN)_2C_6H_{10}O-$), 3-methylcyclohex-1-yl, methylenebis(cyclohex-4-yloxy) (i.e., $-OC_6H_{10}CH_2C_6H_{10}O-$), 1-ethylcyclobut-1-yl, cyclopropylethenyl, 3-formyl-2-terahydrofuranyl, 2-hexyl-5-tetrahydrofuranyl, hexamethylene-1,6-bis(cyclohex-4-yloxy) (i.e., $-OC_6H_{10}(CH_2)_6C_6H_{10}O-$), 4-hydroxymethylcyclohex-1-yl (i.e., $4-HOCH_2C_6H_{10}-$), 4-mercaptomethylcyclohex-1-yl (i.e., $4-HSCH_2C_6H_{10}-$), 4-methylthiocyclohex-1-yl (i.e., $4-CH_3SC_6H_{10}-$), 4-methoxycyclohex-1-yl, 2-methoxycarbonylcyclohex-1-yloxy ($2-CH_3OCOC_6H_{10}-$), 4-nitromethylcyclohex-1-yl (i.e., $NO_2CH_2C_6H_{10}-$), 3-trimethylsilylcyclohex-1-yl, 2-t-butyldimethylsilylcyclopent-1-yl, 4-trimethoxysilylethylcyclohex-1-yl (e.g. $(CH_3O)_3SiCH_2CH_2C_6H_{10}-$), 4-vinylcyclohexen-1-yl, vinylidenebis(cyclohexyl), and the like. The term "a $C_3$-$C_{10}$ cycloaliphatic radical" includes cycloaliphatic radicals containing at least three but no more than 10 carbon atoms. The cycloaliphatic radical 2-tetrahydrofuranyl ($C_4H_7-$) represents a $C_4$ cycloaliphatic radical. The cyclohexylmethyl radical ($C_6H_{11}CH_2-$) represents a $C_7$ cycloaliphatic radical.

As used herein the term "aliphatic radical" refers to an organic radical having a valence of at least one consisting of a linear or branched array of atoms which is not cyclic. Aliphatic radicals are defined to comprise at least one carbon atom. The array of atoms comprising the aliphatic radical may include heteroatoms such as nitrogen, sulfur, silicon, selenium and oxygen or may be composed exclusively of carbon and hydrogen. For convenience, the term "aliphatic radical" is defined herein to encompass, as part of the "linear or branched array of atoms which is not cyclic" organic radicals substituted with a wide range of functional groups such as alkyl groups, alkenyl groups, alkynyl groups, haloalkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylpent-1-yl radical is a $C_6$ aliphatic radical comprising a methyl group, the methyl group being a functional group which is an alkyl group. Similarly, the 4-nitrobut-1-yl group is a $C_4$ aliphatic radical comprising a nitro group, the nitro group being a functional group. An aliphatic radical may be a haloalkyl group which comprises one or more halogen atoms which may be the same or different. Halogen atoms include, for example; fluorine, chlorine, bromine, and iodine. Aliphatic radicals comprising one or more halogen atoms include the alkyl halides trifluoromethyl, bromodifluoromethyl, chlorodifluoromethyl, hexafluoroisopropylidene, chloromethyl, difluorovinylidene, trichloromethyl, bromodichloromethyl, bromoethyl, 2-bromotrimethylene (e.g. $-CH_2CHBrCH_2-$), and the like. Further examples of aliphatic radicals include allyl, aminocarbonyl (i.e., $-CONH_2$), carbonyl, 2,2-dicyanoisopropylidene (i.e., $-CH_2C(CN)_2CH_2-$), methyl (i.e., $-CH_3$), methylene (i.e., $-CH_2-$), ethyl, ethylene, formyl (i.e. $-CHO$), hexyl, hexamethylene, hydroxymethyl (i.e. $-CH_2OH$), mercaptomethyl (i.e., $-CH_2SH$), methylthio (i.e., $-SCH_3$), methylthiomethyl (i.e., $-CH_2SCH_3$), methoxy, methoxycarbonyl (i.e., $CH_3OCO-$), nitromethyl (i.e., $-CH_2NO_2$), thiocarbonyl, trimethylsilyl (i.e., $(CH_3)_3Si-$), t-butyldimethylsilyl, 3-trimethyoxysilypropyl (i.e., $(CH_3O)_3SiCH_2CH_2CH_2-$), vinyl, vinylidene, and the like. By way of further example, a $C_1$-$C_{10}$ aliphatic radical contains at least one but no more than 10 carbon atoms. A methyl group (i.e., $CH_3-$) is an example of a $C_1$ aliphatic radical. A decyl group (i.e., $CH_3(CH2)_9-$) is an example of a $C_{10}$ aliphatic radical.

The term "heteroaryl" as used herein refers to aromatic or unsaturated rings in which one or more carbon atoms of the aromatic ring(s) are replaced by a heteroatom(s) such as nitrogen, oxygen, boron, selenium, phosphorus, silicon or sulfur. Heteroaryl refers to structures that may be a single aromatic ring, multiple aromatic ring(s), or one or more aromatic rings coupled to one or more non-aromatic ring(s). In structures having multiple rings, the rings can be fused together, linked covalently, or linked to a common group such as an ether, methylene or ethylene moiety. The common linking group may also be a carbonyl as in phenyl pyridyl ketone. As used herein, rings such as thiophene, pyridine, isoxazole, pyrazole, pyrrole, furan, etc. or benzo-fused analogues of these rings are defined by the term "heteroaryl."

The term "aryl" is used herein to refer to an aromatic substituent which may be a single aromatic ring or multiple aromatic rings which are fused together, linked covalently, or linked to a common group such as an ether, methylene or ethylene moiety. The aromatic ring(s) may include phenyl, naphthyl, anthracenyl, and biphenyl, among others. In particular embodiments, aryls have between 1 and 200 carbon atoms, between 1 and 50 carbon atoms or between 1 and 20 carbon atoms.

The term "alkyl" is used herein to refer to a branched or unbranched, saturated or unsaturated acyclic hydrocarbon radical. Suitable alkyl radicals include, for example, methyl, ethyl, n-propyl, i-propyl, 2-propenyl (or allyl), vinyl, n-butyl, t-butyl, i-butyl (or 2-methylpropyl), etc. In particular embodiments, alkyls have between 1 and 200 carbon atoms, between 1 and 50 carbon atoms or between 1 and 20 carbon atoms.

The term "cycloalkyl" is used herein to refer to a saturated or unsaturated cyclic non-aromatic hydrocarbon radical having a single ring or multiple condensed rings. Suitable cycloalkyl radicals include, for example, cyclopentyl, cyclohexyl, cyclooctenyl, bicyclooctyl, etc. In particular embodiments, cycloalkyls have between 3 and 200 carbon atoms, between 3 and 50 carbon atoms or between 3 and 20 carbon atoms.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

EXAMPLES

Examples 1-31 describe the syntheses of compounds of the invention and intermediates used in making them. All reagents were purchased from Aldrich Chemical Co., Milwaukee, Wis., USA and Acros Organics unless other wise specified and were used without further purification. All compounds were characterized by $^1$H-NMR and found to correspond to the structures shown.

Example 1

Synthesis of Compound 25

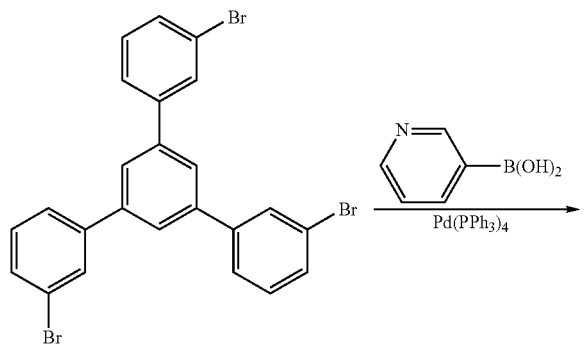

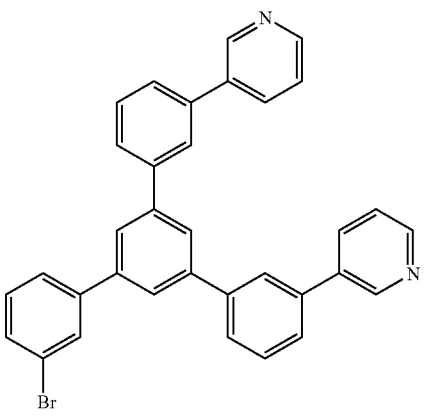

25

A 100 mL, round-bottomed Schlenk flask equipped with a magnetic stir bar was charged with 1,3,5-tri(3-bromobenzene) benzene (6.52 g, 12.0 mmol), 3-pyridyl boronic acid (3.69 g, 30 mmol), 25 mL of a 2 M aqueous solution of $Na_2CO_3$, and 25 mL of 1,4-dioxane. Tetrakis (triphenylphosphine) palladium (0.54 g, 0.5 mmol) was added, the mixture was degassed using five vacuum/nitrogen back-fill cycles, and then was heated to 95° C. for 24 hours with vigorous stirring. The reaction mixture was allowed to cool to room temperature and diluted with $CH_2Cl_2$. The organic layer was washed with 1N HCl, $H_2O$, and brine, dried over $Na_2SO_4$, and concentrated to dryness by rotary evaporation. The resulting yellow solid was purified by column chromatography on silica gel. Eluent ethyl acetate gave compound 25 as a white solid 2.5 g (39%). $^1$H NMR (400 MHz, $CDCl_3$) δ 8.95 (br s, 2H), 8.65 (br s, 2H), 7.98-7.41 (m, 19H).

Example 2

Synthesis of Compound 1

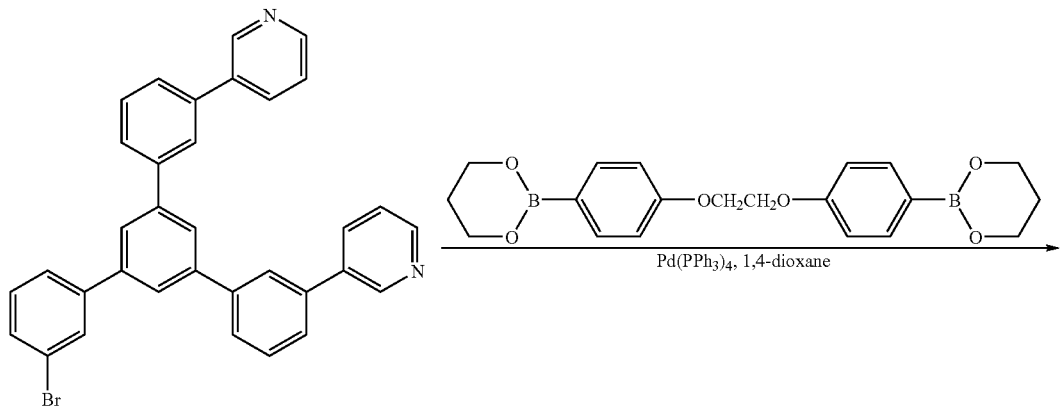

25

-continued

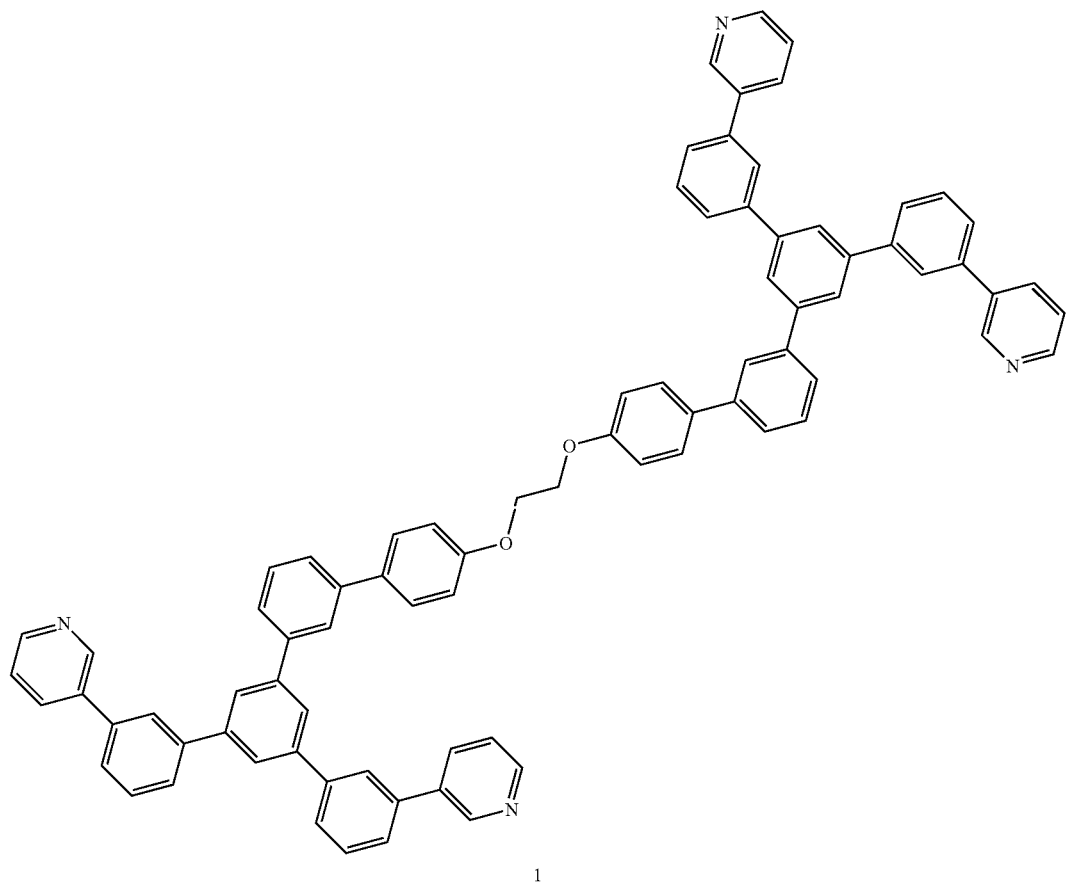

1

A 100 mL, two-necked, round-bottomed flask was covered in tin foil and was equipped with a stirring bar, a reflux condenser fitted with a nitrogen inlet, and a stopper. The flask was charged compound 25 (0.864 g, 1.6 mmol), 1,4-dioxane (20 mL), and tetrakis (triphenylphosphine) palladium (43.4 mg, 0.037 mmol). The apparatus was maintained under an atmosphere of nitrogen during the course of the reaction. The mixture was stirred at room temperature for 20 minutes then potassium carbonate (0.42 g, 3 mmol) dissolved in distilled water (4 mL) was added via funnel, followed by 1,2-bis(4-(1,3,2-dioxaborinan-2-yl)phenoxy) (0.3 g, 0.79 mmol). The reaction mixture was stirred and heated at reflux in an oil bath for 20 h, then cooled to ambient temperature. Distilled water (20 mL) was added via a funnel, and the resulting mixture was filtered on a Büchner funnel. The filtrate was transferred to a separatory funnel and extracted with $CH_2Cl_2$ (3×30 mL). The combined organic phases were dried over $Na_2SO_4$, filtered on filter paper and concentrated to dryness by rotary evaporation (30° C., 25 mmHg). The resulting yellow solid was purified by column chromatography ($SiO_2$:Ethyl acetate/THF (V/V: 4/1) as eluant) to give compound 1 as a white solid, which was dissolved in 2 mL $CH_2Cl_2$, precipitated into ether (50 mL) to afford final product compound 1 (0.60, 66%). $^1$H NMR (400 MHz, $CDCl_3$) δ 8.96 (s, 4H), 8.65 (s, 4H), 7.98-7.91 (m, 16H), 7.76-7.55 (m, 22H), 7.43-7.40 (m, 4H), 7.09 (d, 4H), 4.43 (s, 4H).

Example 3

Synthesis of Compound 27

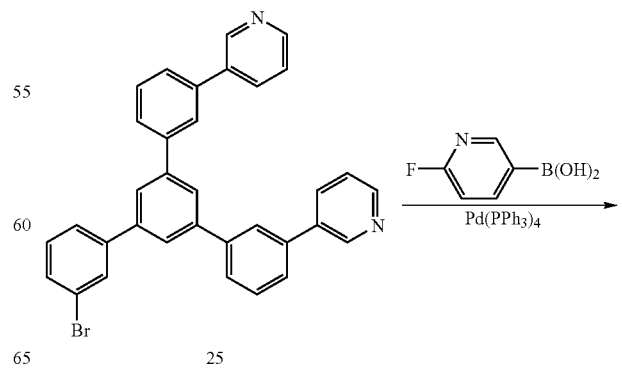

-continued

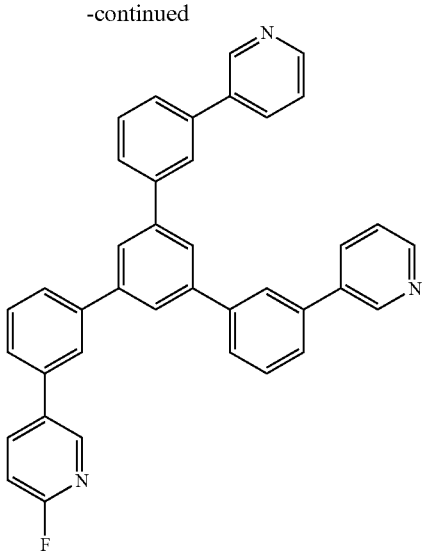

27

A 100 mL, two-necked, round-bottomed flask covered in tin foil and was equipped with a stirring bar, a reflux con- denser fitted with a nitrogen inlet, and a stopper. The flask was charged compound 25 (1.75 g, 3.24 mmol), 1,4-dioxane (30 mL), and tetrakis (triphenylphosphine) palladium (86.9 mg, 0.073 mmol). The apparatus was maintained under an atmosphere of nitrogen during the course of the reaction. The mixture was stirred at room temperature for 20 minutes then potassium carbonate (0.83 g, 5.9 mmol) dissolved in distilled water (8 mL) was added via funnel, followed by 2-fluoropyridine-5-boronic acid pinacolester (1.1 g, 4.8 mmol). The reaction mixture was stirred and heated at reflux in an oil bath for 20 h, then cooled to ambient temperature. Distilled water (30 mL) was added via a funnel, and the resulting mixture was filtered on a Büchner funnel. The filtrate was transferred to a separatory funnel and extracted with $CH_2Cl_2$ (3×30 mL). The combined organic phases were dried over $Na_2SO_4$, filtered on filter paper and concentrated to dryness by rotary evaporation (30° C., 25 mmHg). The resulting yellow solid was purified by column chromatography affording as a white solid 1.67 g (93%). $^1$H NMR (400 MHz, $CDCl_3$) δ 8.95 (d, 2H), 8.65 (m, 2H), 8.52 (d, 1H), 8.07 (m, 1H), 7.98-7.79 (m, 11H), 7.65-7.59 (m, 6H), 7.42 (t, 2H), 7.06 (t, 1H).

Example 4

Synthesis of Compound 2

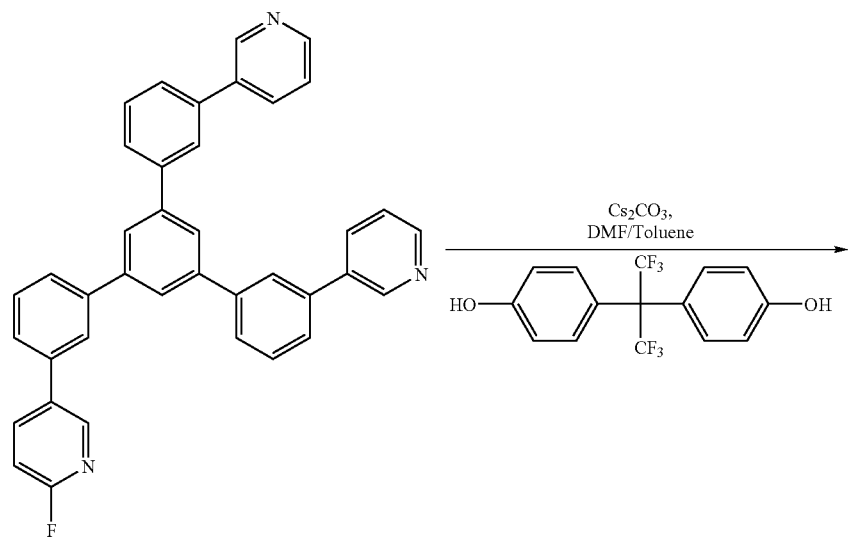

27

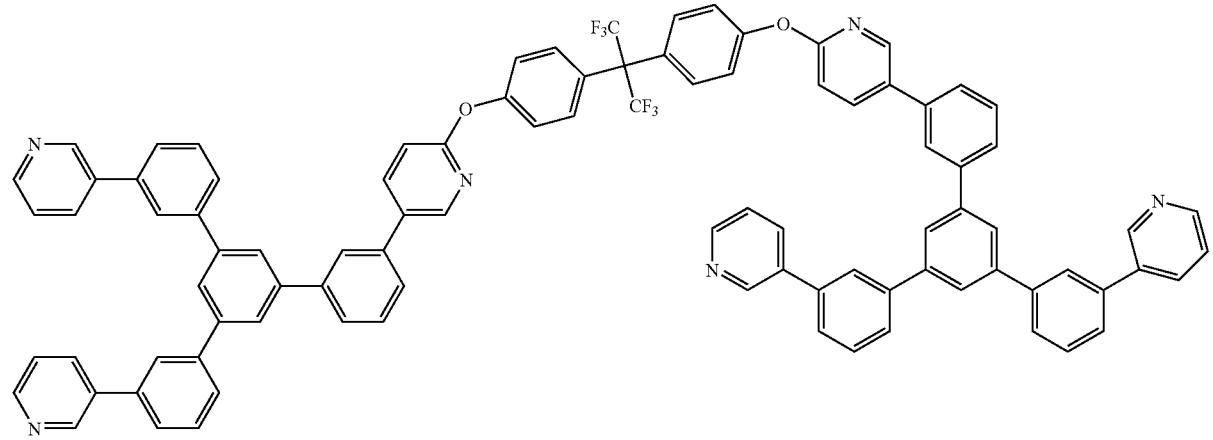

2

A 25 mL Schlenk flask equipped with a magnetic stir bar and a Stark and Dean water trap and reflux condenser was charged with toluene (5 mL) and DMF (5 mL) and put under a nitrogen atmosphere. A mixture of Compound 27 (0.91 g, 1.64 mmol), hexafluoroisopropylidene bis(4-hydroxybenzene) (0.242 g, 0.72 mmol) and Cesium carbonate (0.61 g, 1.9 mmol) was dissolved in the solvent. The mixture was heated to 140° C. for 24 hours with vigorous stirring. The reaction mixture was allowed to cool to room temperature and diluted with $CH_2Cl_2$. The organic layer was washed with 1N HCl, $H_2O$, and brine, dried over $Na_2SO_4$, and concentrated to dryness by rotary evaporation. The resulting yellow solid was purified by column chromatography on silica gel. Eluent ethyl acetate/THF (V/V:4/1) gave compound 2 as a white solid 0.99 g (97%). Then the white solid was re-dissolved in ethanol, a little $CH_2Cl_2$ was added to help the solubility. Some powders came out after overnight, collected the white powder (620 mg). $^1$H NMR (400 MHz, $CDCl_3$) δ 8.95 (d, 4H), 8.64 (m, 4H), 8.55 (d, 2H), 8.05-7.88 (m, 18H), 7.78-7.75 (m, 6H), 7.64-7.61 (m, 12H), 7.50 (m, 4H), 7.42 (m, 4H), 7.23 (d, 4H), 7.09 (d, 4H).

Example 5

Synthesis of Compound 28

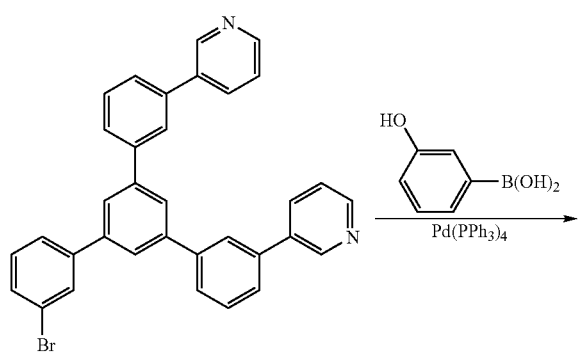

25

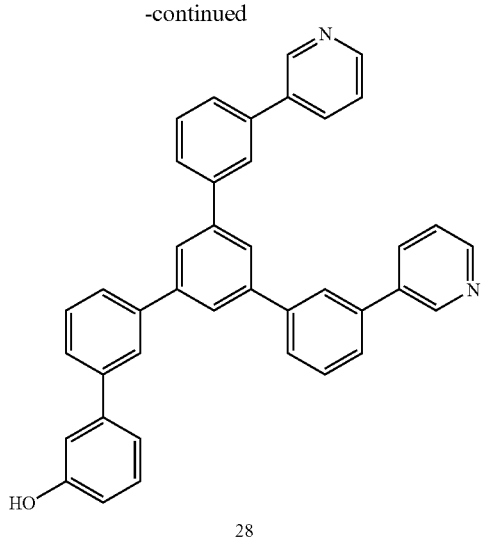

28

3-Hydroxyphenylboronic acid (0.62 g, 4.53 mmol), $Na_2CO_3$ (0.62 g) MeOH(16 mL), and $H_2O$ (8 mL) were added in turn to a mixture of compound 25 (1.6 g, 3 mmol), $Pd(PPh_3)_4$ (0.18 g, 0.16 mmol) and tri-tert-butylphosphine(6 mL, 10 wt % in hexane) in dioxane (50 mL). This mixture was degassed using five vacuum/nitrogen back-fill cycles, and then heated under reflux for 24 h. After cooling to room temperature, the mixture was partitioned between $H_2O$ (100 mL) and $CH_2Cl_2$ (100 mL). The organic layer was collected, dried over $MgSO_4$ and concentrated to afford a crude product, which was purified by column chromatography ($SiO_2$; Ethyl acetate as eluant) to give compound 28 as a white solid (1.60, 96%). $^1$H NMR (400 MHz, $CDCl_3$): δ=8.97 (s, 2H), 8.65 (s, 2H), 7.99 (d, 2H), 7.90 (m, 6H), 7.77 (m, 2H), 7.70 (d, 2H), 7.63 (m, 5H), 7.55 (t, 1H), 7.43 (t, 2H), 7.34 (t, 1H), 7.21 (m, 2H), 6.91 (d, 1H).

Example 6

Synthesis of Compound 3

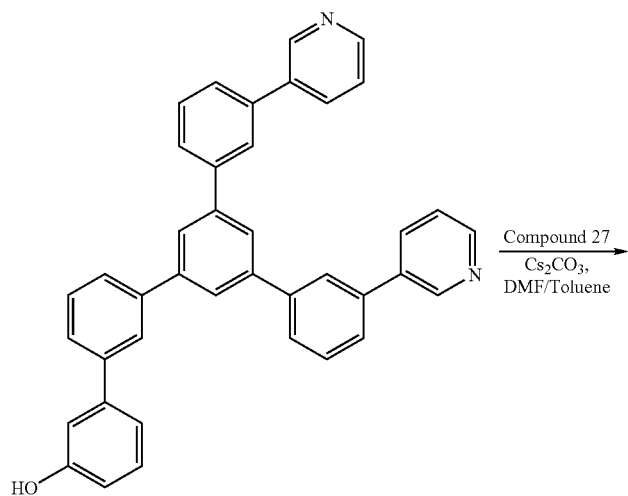

28

-continued

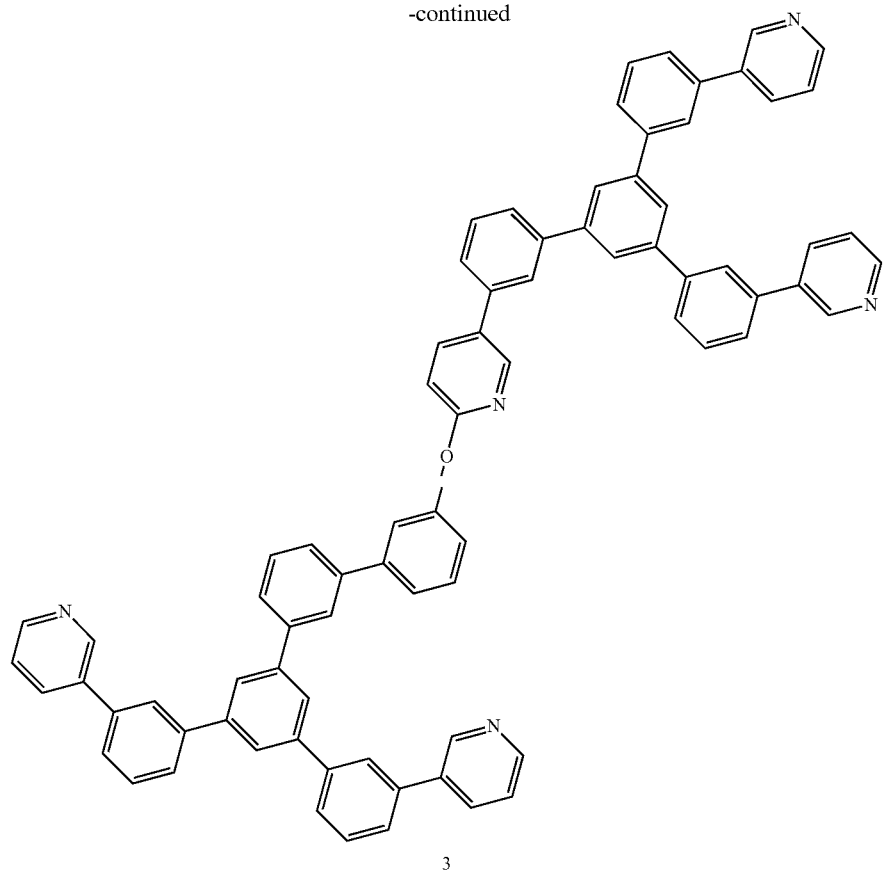

3

A 25 mL Schlenk flask equipped with a magnetic stir bar and a Stark and Dean water trap and reflux condenser was charged with toluene (5 mL) and DMF (5 mL) and put under a nitrogen atmosphere. A mixture of Compound 27 (0.37 g, 0.67 mmol), Compound 28 (0.37 g, 0.66 mmol) and Cesium carbonate (0.284 g, 0.87 mmol) was dissolved in the solvent. The mixture was heated to 140° C. for 24 hours with vigorous stirring. The reaction mixture was allowed to cool to room temperature and diluted with $CH_2Cl_2$. The organic layer was washed with 1 N HCl, $H_2O$, and brine, dried over $Na_2SO_4$, and concentrated to dryness by rotary evaporation. The resulting yellow solid was purified by column chromatography on silica gel. Eluent ethyl acetate/THF (V/V:4/1) gave compound 3 as a white solid 0.623 g (87%). Then the white solid was re-dissolved in ethanol, a little $CH_2Cl_2$ was added to help the solubility. Some powders came out after overnight, collected the white powder (320 mg). $^1$H NMR (400 MHz, $CDCl_3$) δ 8.94 (d, 4H), 8.64 (m, 4H), 8.52 (d, 1H), 8.01-7.40 (m, 38H), 7.22 (m, 1H), 7.08 (d, 1H).

Example 8

Synthesis of Compound 4

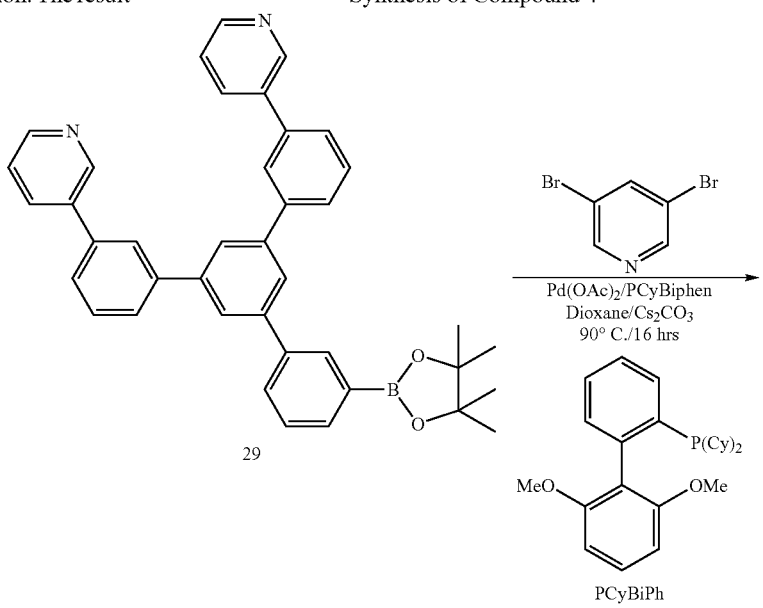

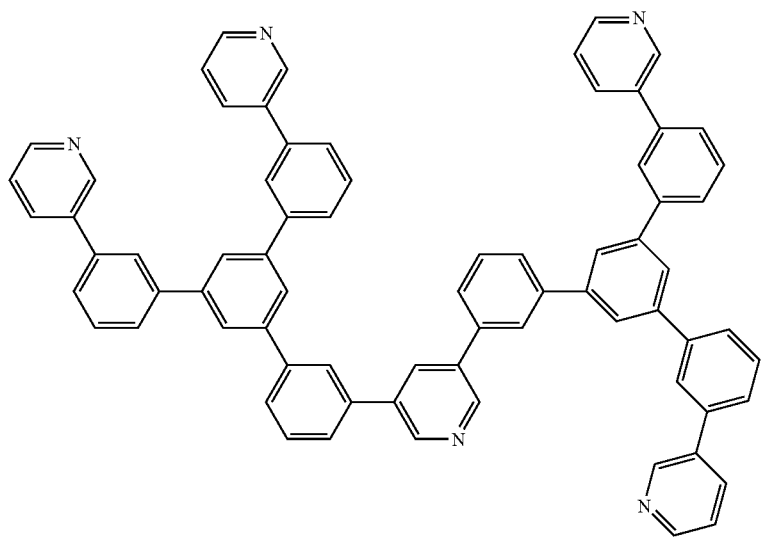

4

3,5-Bibromopyridine (0.39 g, 1.67 mmol), Cs$_2$CO$_3$ (6.5 g, 20 mmol), Pd(OAc)$_2$ (35 mg) and PCyBiPhen (150 mg) were added in turn to a mixture of compound 29 (3 g, 5 mmol in dioxane (50 mL). This mixture was degassed using five vacuum/nitrogen back-fill cycles, and then heated to 90 degree for 16 h. After cooling to room temperature, the mixture was filtered and washed with CH$_2$Cl$_2$ (20 mL). The filter liquid was collected and concentrated to afford a crude product, which is purified by column chromatography to give compound 4 (1.55 g, 93%). $^1$H NMR (400 MHz, CDCl$_3$) δ 8.95 (m, 6H), 8.64 (m, 4H), 8.20 (m, 1H), 7.98-7.90 (m, 16H), 7.79-7.62 (m, 19H), 7.41 (m, 4H). The product was dissolved in 3 mL CH$_2$Cl$_2$, then ethyl ether (50 mL) was added slowly. White powder was precipitated and collected by centrifugation, then washed the powder 3 times with ethyl ether.

Example 9

Synthesis of Compound 4

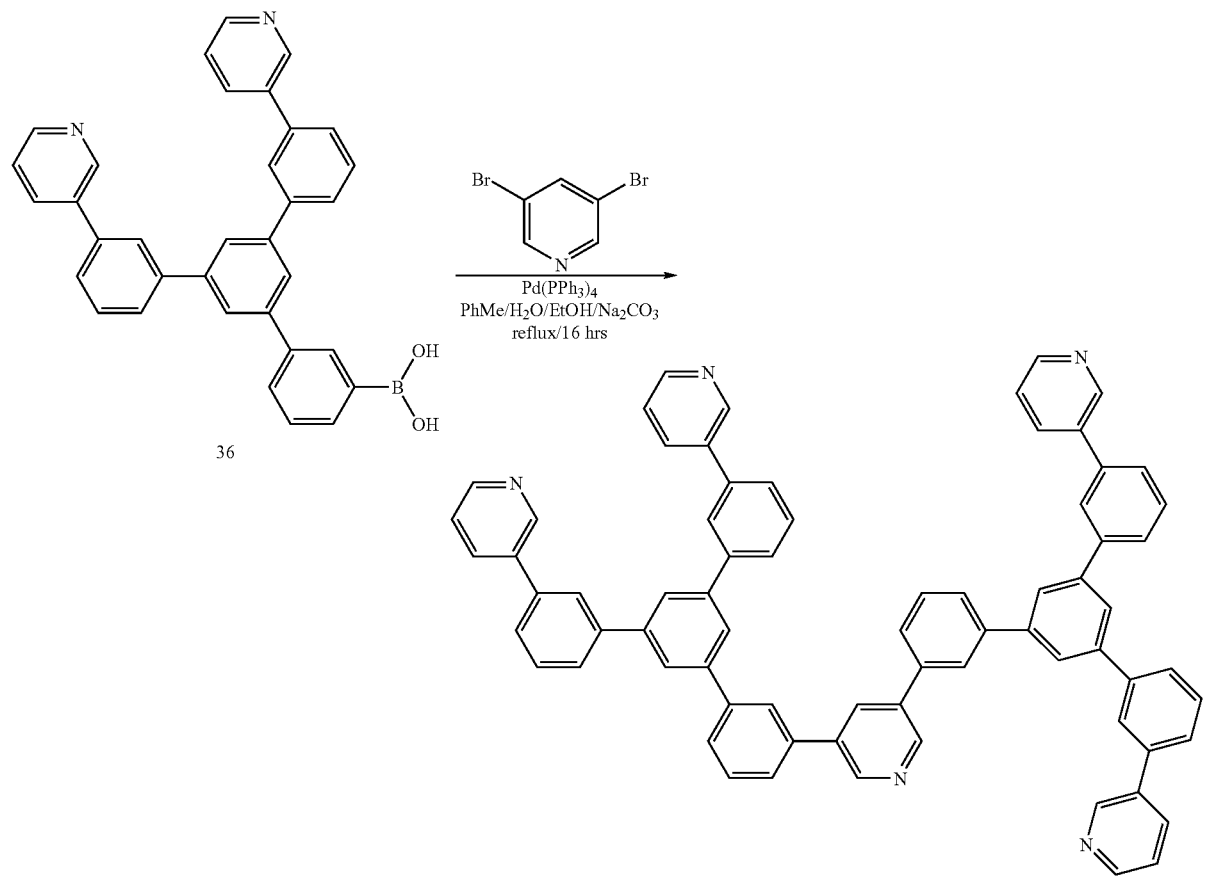

4

A biphasic mixture of toluene (10 mL)/H$_2$O (5.0 mL)/EtOH (5.0 mL) containing Na$_2$CO$_3$ (1.10 g) was purged with nitrogen. To this solution was added the boronic acid compound 36 (0.500 g, 1.00 mmol), 3,5-dibromopyridine (107 mg, 0.450 mmol) followed by Pd(PPh$_3$)$_4$ (40.0 mg, 0.0400 mmol). The reaction was placed under an inert atmosphere of nitrogen and heat at a gentle reflux for 16 h. The mixture was cooled to room temperature and transferred to a separatory with EtOAc (50 mL) and washed with brine (2×100 mL). The organic layer was dried over Na$_2$SO$_4$, stirred with 3-mercaptopropyl-functionalized silica gel. (1.0 g, Aldrich) and filtered. The filter cake was washed with 5% MeOH/CH$_2$Cl$_2$ and the filtrate was concentrated to dryness to give a foam. The crude material was chromatographed through SiO$_2$ and eluted with 5% MeOH/CH$_2$Cl$_2$ to afford the product as a white foam. Yield 290 mg, 65%. $^1$H NMR (400 MHz, CD$_2$Cl$_2$, 25° C.) δ7.39 (m, 4H), 7.64 (m, 10H), 7.76 (m, 8H), 7.98 (m, 14H), 8.04 (t, 2H), 8.25 (t, 1H), 8.58 (m, 4H), 8.93 (m, 6H).

Example 10

Synthesis of Compound 5

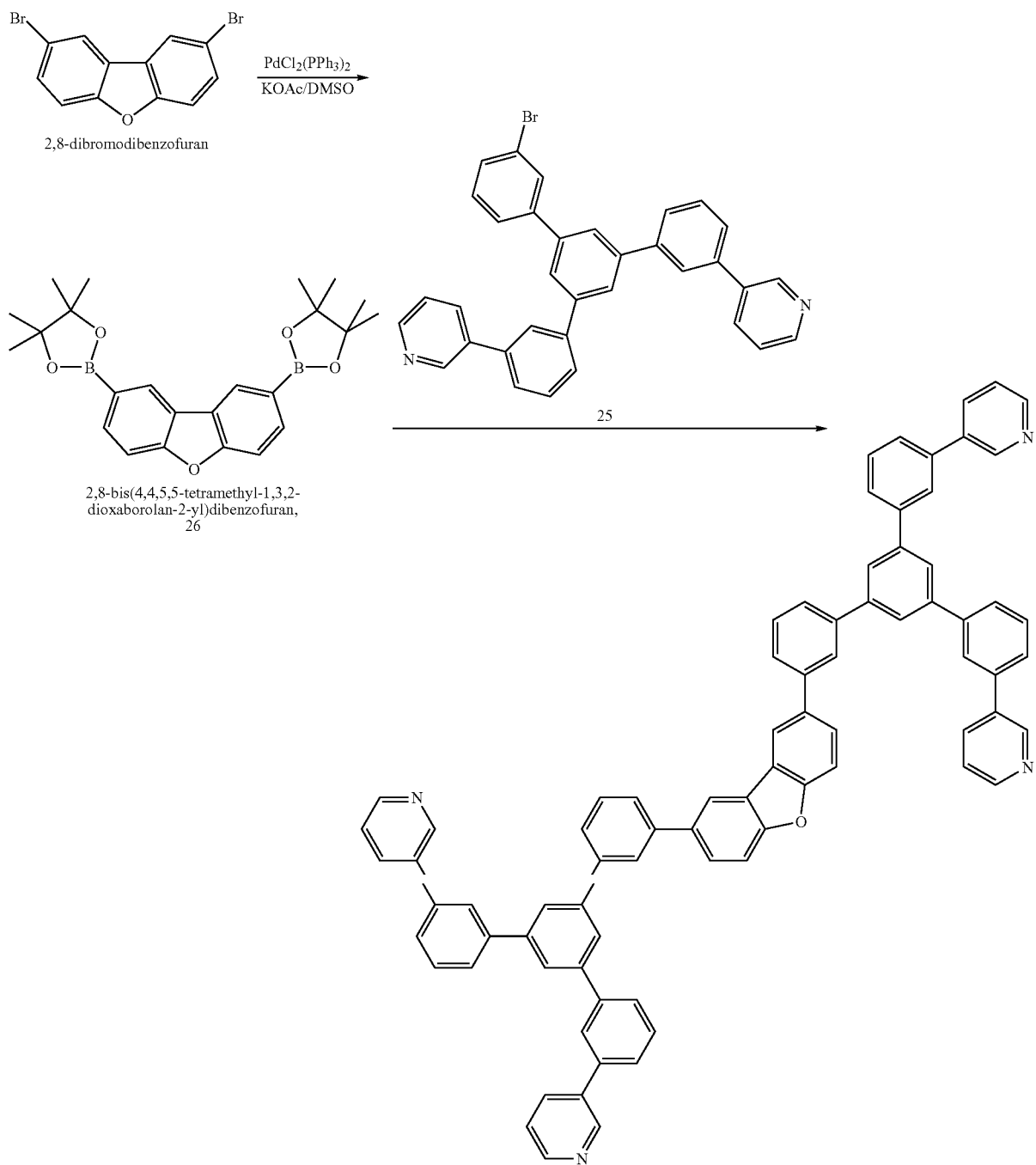

To a 20 mL DMSO solution of 2,8-dibromodibenzofuran (1 g, 3.07 mmol) was added bispinacolatiodiboron (1.74 g, 6.75 mmol), KOAc (2 g, 21 mmol) and PdCl$_2$(PPh$_3$)$_2$ (149 mg, 0.21 mmol), and the solution was stirred at 80° C. for 24 h. The catalyst was removed by filtration and washed with CH$_2$Cl$_2$ after the reaction mixture was cooled to room temperature. The filtrate was then washed with de-ionized H$_2$O (50 mL) for five times, and the organic layer was dried over Mg$_2$SO$_4$, filtrated, concentrated and purified by column chromatography on silica gel (hexane/EtOAc=10:1) to give 2,8-bis(4,4,5,5-tetramethyl-1,3,2-dioxaborolan-2-yl)dibenzofuran (0.4 g, 31%). $^1$H NMR (400 MHz, CDCl$_3$) δ 8.51 (s, 2H), 7.92 (d, 2H), 7.57 (d, 2H), 1.40 (s, 24H).

A 50 mL, two-necked, round-bottomed flask covered in tin foil and was equipped with a stirring bar, a reflux condenser fitted with a nitrogen inlet, and a stopper. The flask was charged 2,8-bis(4,4,5,5-tetramethyl-1,3,2-dioxaborolan-2-yl)dibenzofuran (0.38 g, 0.92 mmol), compound 27 (1.1 g, 2.02 mmol), 1,4-dioxane (20 mL), and tetrakis (triphenylphosphine) palladium (86.9 mg, 0.073 mmol). The apparatus was maintained under an atmosphere of nitrogen during the course of the reaction. The mixture was stirred at room temperature for 20 minutes then potassium carbonate (0.83 g, 5.9 mmol) dissolved in distilled water (8 mL) was added via funnel. The reaction mixture was stirred and heated at reflux in an oil bath for 20 h, then cooled to ambient temperature. Distilled water (20 mL) was added via a funnel, and the resulting mixture was filtered on a Büchner funnel. The filtrate was transferred to a separatory funnel and extracted with CH$_2$Cl$_2$ (3×30 mL). The combined organic phases were dried over Na$_2$SO$_4$, filtered on paper and concentrated to dryness by rotary evaporation (30° C., 25 mmHg). Then purified by column chromatography on silica gel (EtOAc/THF=10:1) to give compound 5 (0.596 g, 60%). $^1$H NMR (400 MHz, CDCl$_3$) δ 8.93 (m, 4H), 8.62 (m, 4H), 8.29 (m, 2H), 8.0-7.91 (m, 15H), 7.81-7.61 (m, 22H), 7.39 (m, 4H).

Example 11

Synthesis of Compound 29

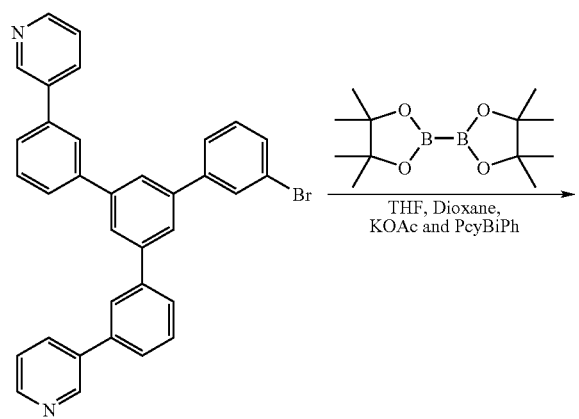

25

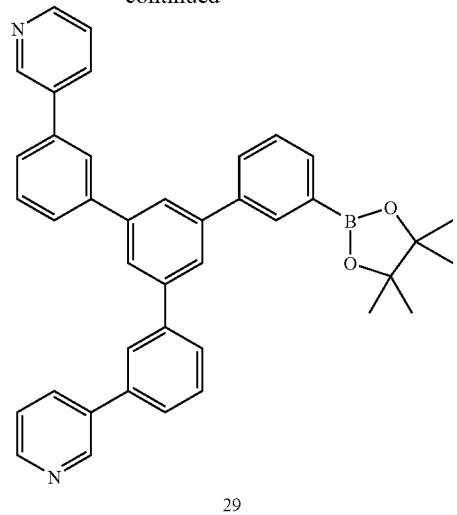

29

A 50 mL, two-necked, round-bottomed flask covered in tin foil and was equipped with a stirring bar, a reflux condenser fitted with a nitrogen inlet, and a stopper. The flask was charged compound 25 (2.175 g, 4.03 mmol), THF (20 mL), 1,4-dioxane (5 mL), pinacolate diborane (3.1 g, 12.2 mmol), Pd(OAc)$_2$ (23.0 mg, 0.100 mmol) dry KOAc (1.47 g, 15.0 mmol), and PcyBiPhen (ligand IV, 103 mg, 0.250 mmol). The apparatus was maintained under an atmosphere of nitrogen during the course of the reaction. The reaction mixture was stirred and heated at reflux in an oil bath for 15 h, then cooled to ambient temperature. Distilled water (30 mL) was added via a funnel, and the resulting mixture was filtered on a Büchner funnel. The filtrate was transferred to a separatory funnel and extracted with CH$_2$Cl$_2$ (3×30 mL). The combined organic phases were dried over Na$_2$SO$_4$, filtered on filter paper and concentrated to dryness by rotary evaporation (30° C., 25 mmHg). The resulting solid was purified by column chromatography affording as a white solid 2.296 g (97%). $^1$H NMR (400 MHz, CDCl$_3$) δ 8.95 (d, 2H), 8.64 (m, 2H), 8.15 (d, 1H), 7.98 (m, 2H), 7.90-7.77 (m, 9H), 7.64 (m, 4H), 7.53 (t, 1H), 7.42 (m, 2H), 1.38 (s, 12H).

Example 12

Synthesis of Compound 29 and 35

To a flame dried 3-neck round bottom flask fitted with a condenser, a nitrogen inlet, and a rubber septum was added compound 25 (2.70 g, 5.00 mmol), pinacolate diborane (3.81 g, 15.0 mmol), dry KOAc (1.47 g, 15.0 mmol), and the cyclohexyl phosphine ligand (103 mg, 0.250 mmol). The flask was placed then protected from the atmosphere and was charged with anhydrous THF (20 mL), Dioxane (5 mL), and the solution was degassed by purging N$_2$ through the stirred solution. After 15 minutes, the reaction mixture was charged with Pd(OAc)$_2$ (23.0 mg, 0.100 mmol) and the mixture was heated at reflux for 12 h. After this time had passed, the reaction mixture was cooled to room temperature (RT) and filtered through celite. The filter cake was washed with EtOAc and the filtrate was concentrated to dryness. The residue was chromatographed through SiO$_2$ with an EtOAc eluent. Yield 2.65 g, 90%. $^1$H NMR (400 MHz, CD$_2$Cl$_2$, 25° C.) δ 1.39 (s, 12H), 7.41 (m, 2H), 7.52 (t, 1H, 7.63 (m, 4H), 7.82 (m, 4H), 7.92 (s, 3H); 7.96 (m, 2H), 8.00 (m, 2H), 8.13 (s, 1H), 8.60 (m, 2H), 8.94 (d, 2H). The pinacol borate ester can be converted into the corresponding boronic acid by heating the ester in a mixture of dilute H$_2$SO$_4$ and MeOH. After the acid is neutralized with NaHCO$_3$ the solid that is obtained after concentrating to dryness is suspended in H$_2$O, filtered, washed with H$_2$O, and dried.

Example 13

Synthesis of Compound 30

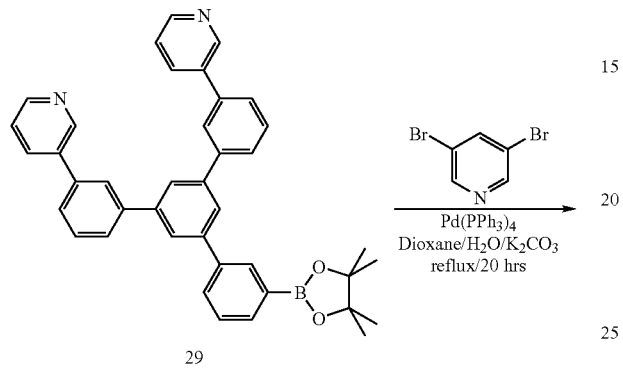

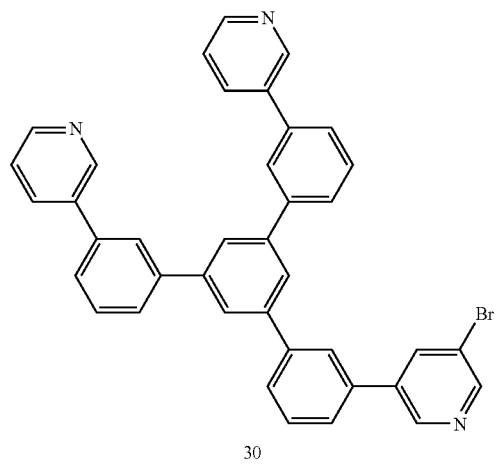

A 100 mL, two-necked, round-bottomed flask covered in tin foil and was equipped with a stirring bar, a reflux condenser fitted with a nitrogen inlet, and a stopper. The flask was charged compound 29 (2.296 g, 3.914 mmol), 3,5-dibromopyridine (1.391 g, 5.87 mmol), 1,4-dioxane (30 mL), and tetrakis (triphenylphosphine) palladium (86.9 mg, 0.073 mmol). The apparatus was maintained under an atmosphere of nitrogen during the course of the reaction. The mixture was stirred at room temperature for 20 minutes then potassium carbonate (0.83 g, 5.9 mmol) dissolved in distilled water (8 mL) was added via funnel. The reaction mixture was stirred and heated at reflux in an oil bath for 20 h, then cooled to ambient temperature. Distilled water (30 mL) was added via a funnel, and the resulting mixture was filtered on a Büchner funnel. The filtrate was transferred to a separatory funnel and extracted with CH$_2$Cl$_2$ (3×30 mL). The combined organic phases were dried over Na$_2$SO$_4$, filtered on filter paper and concentrated to dryness by rotary evaporation (30° C., 25 mmHg). The resulting yellow solid was purified by column chromatography affording as a white solid 1.45 g (60%). $^1$H NMR (400 MHz, CDCl$_3$) δ 8.95 (d, 2H), 8.85 (d, 1H), 8.52 (d, 1H), 8.71 (d, 1H), 8.65 (m, 2H), 8.12 (m, 1H), 7.98 (m, 2H), 7.91-7.87 (m, 6H), 7.82-7.77 (m, 3H), 7.65 (m, 6H), 7.42 (t, 2H).

Example 14

Synthesis of Compound 31

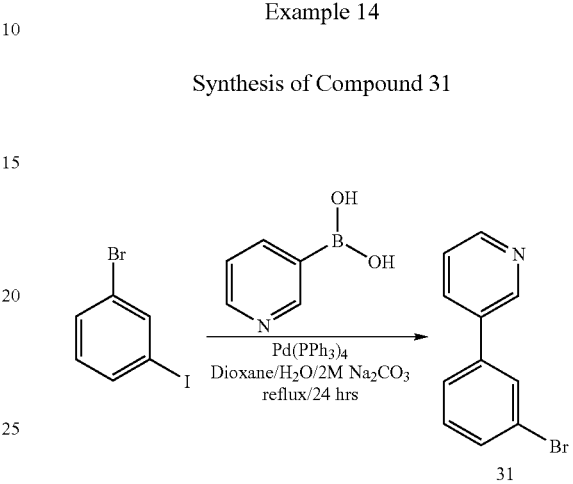

A 100 mL, round-bottomed Schlenk flask equipped with a magnetic stir bar was charged with 1-bromo-3-iodobenzene (5.754 g, 20.3 mmol), 3-pyridyl boronic acid (2.5 g, 20.3 mmol), 25 mL of a 2 M aqueous solution of Na$_2$CO$_3$, and 25 mL of 1,4-dioxane. Tetrakis (triphenylphosphine) palladium (0.54 g, 0.5 mmol) was added, the mixture was degassed using five vacuum/nitrogen back-fill cycles, and then was heated to 95° C. for 24 hours with vigorous stirring. The reaction mixture was allowed to cool to room temperature and diluted with CH$_2$Cl$_2$. The organic layer was washed with 1N HCl, H$_2$O, and brine, dried over Na$_2$SO$_4$, and concentrated to dryness by rotary evaporation. The resulting yellow solid was purified by column chromatography on silica gel. Eluent ethyl acetate/hexane (3/97) gave compound 31 as a pale yellow oil 3.6 g (77%). $^1$H NMR (400 MHz, CDCl$_3$) δ 8.82 (br s, 1H), 8.63 (m, 1H), 7.85 (m, 1H), 7.73 (m, 1H), 7.53 (m, 2H), 7.36 (m, 2H).

Example 15

Synthesis Compound 32

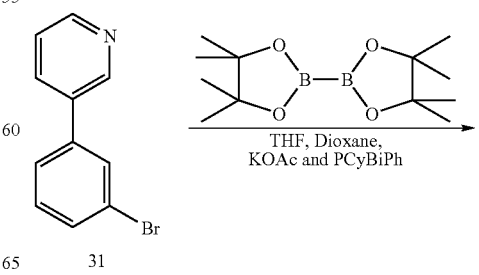

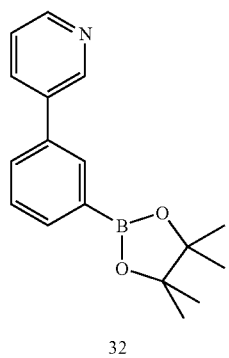

32

A 50 mL, two-necked, round-bottomed flask covered in tin foil and was equipped with a stirring bar, a reflux condenser fitted with a nitrogen inlet, and a stopper. The flask was charged 3-(3-bromophenyl) pyridine (2 g, 8.54 mmol), THF (20 mL), 1,4-dioxane (5 mL), pinacolate diborane (4.34 g, 17.09 mmol), dry KOAc (1.01 g, 10.4 mmol), Pd(OAc)2 (17 mg, 0.07 mmol) and PcyBiPhen (ligand IV, 71 mg, 0.172 mmol). The apparatus was maintained under an atmosphere of nitrogen during the course of the reaction. The reaction mixture was stirred and heated at reflux in an oil bath for 15 h, then cooled to ambient temperature. Distilled water (30 mL) was added via a funnel, and the resulting mixture was filtered on a Büchner funnel. The filtrate was transferred to a separatory funnel and extracted with $CH_2Cl_2$ (3×30 mL). The combined organic phases were dried over $Na_2SO_4$, filtered on filter paper and concentrated to dryness by rotary evaporation (30° C., 25 mmHg). The resulting solid was purified by column chromatography affording as a white solid 2.15 g (90%). $^1$H NMR (400 MHz, $CDCl_3$) δ 8.89 (br s, 1H), 8.60 (d, 1H), 8.05 (s, 1H), 7.92 (m, 1H), 7.87 (m, 1H), 7.7 (m, 1H), 7.51 (m, 1H), 7.37 (m, 1H), 1.39 (s, 12H).

Example 16

Synthesis of Compound 33

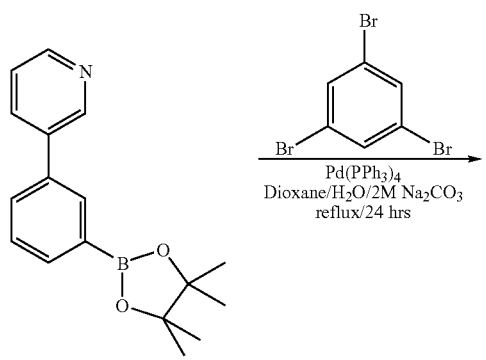

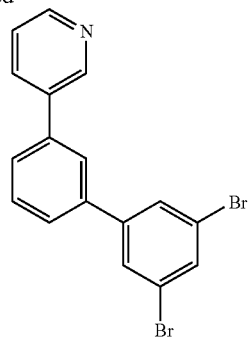

33

A 100 mL, round-bottomed Schlenk flask equipped with a magnetic stir bar was charged with compound 32 (2.15 g, 7.65 mmol), 1,3,5-tribromobenzene (3.61 g, 11.5 mmol), 25 mL of a 2M aqueous solution of $Na_2CO_3$, and 25 mL of 1,4-dioxane. Tetrakis (triphenylphosphine) palladium (0.54 g, 0.5 mmol) was added, the mixture was degassed using five vacuum/nitrogen back-fill cycles, and then was heated to 95° C. for 24 hours with vigorous stirring. The reaction mixture was allowed to cool to room temperature and diluted with $CH_2Cl_2$. The organic layer was washed with 1 N HCl, $H_2O$, and brine, dried over $Na_2SO_4$, and concentrated to dryness by rotary evaporation. The resulting yellow solid was purified by column chromatography on silica gel. Eluent ethyl acetate/hexane(3/97) gave compound 33 as a white solid 1.84 g (62%). $^1$H NMR (400 MHz, $CDCl_3$) δ 8.91 (br s, 1H), 8.66 (m, 1H), 7.94 (m, 1H), 7.72-7.69 (m, 4H), 7.63-7.58 (m, 3H), 7.42 (m, 1H).

Example 17

Synthesis of Compound 34

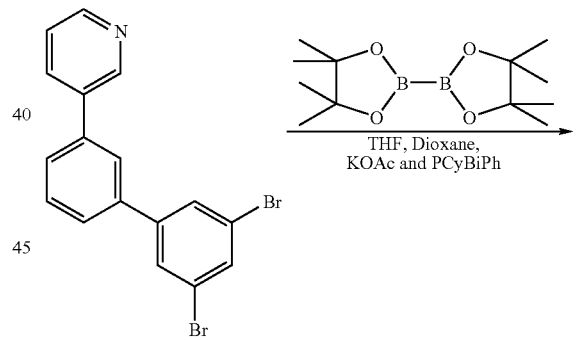

33

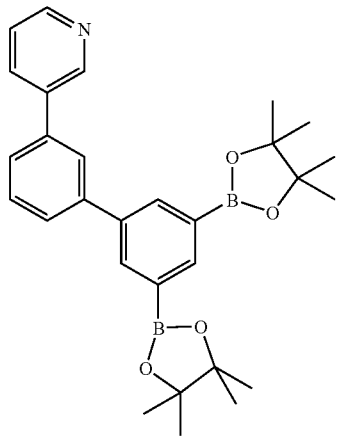

34

A 50 mL, two-necked, round-bottomed flask covered in tin foil and was equipped with a stirring bar, a reflux condenser fitted with a nitrogen inlet, and a stopper. The flask was charged compound 33 (1.84 g, 4.72 mmol), THF (20 mL), 1,4-dioxane (5 mL), pinacolate diborane (6.0 g, 23.63 mmol), dry KOAc (2.3 g, 23.92 mmol), Pd(OAc)$_2$ (36 mg, 0.15 mmol) and PCyBiPhen (162 mg, 0.39 mmol). The apparatus was maintained under an atmosphere of nitrogen during the course of the reaction. The reaction mixture was stirred and heated at reflux in an oil bath for 15 h, then cooled to ambient temperature. Distilled water (30 mL) was added via a funnel, and the resulting mixture was filtered on a Büchner funnel. The filtrate was transferred to a separatory funnel and extracted with CH$_2$Cl$_2$ (3×30 mL). The combined organic phases were dried over Na$_2$SO$_4$, filtered on filter paper and concentrated to dryness by rotary evaporation (30° C., 25 mmHg). The resulting solid was purified by column chromatography affording as a white solid 1.12 g (49%). $^1$H NMR (400 MHz, CDCl$_3$) δ 8.93 (m, 1H), 8.64 (m, 1H), 8.32 (m, 1H), 8.19 (d, 2H), 7.98 (m, 1H), 7.86 (m, 1H), 7.73 (m, 1H), 7.56 (m, 2H), 7.42 (m, 1H), 1.38 (s, 24H).

Example 18

Synthesis of Compound 6

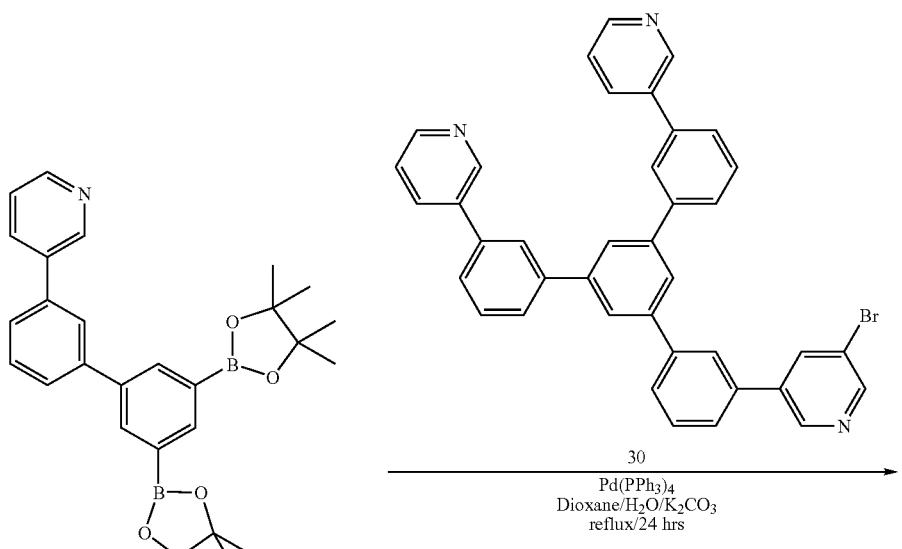

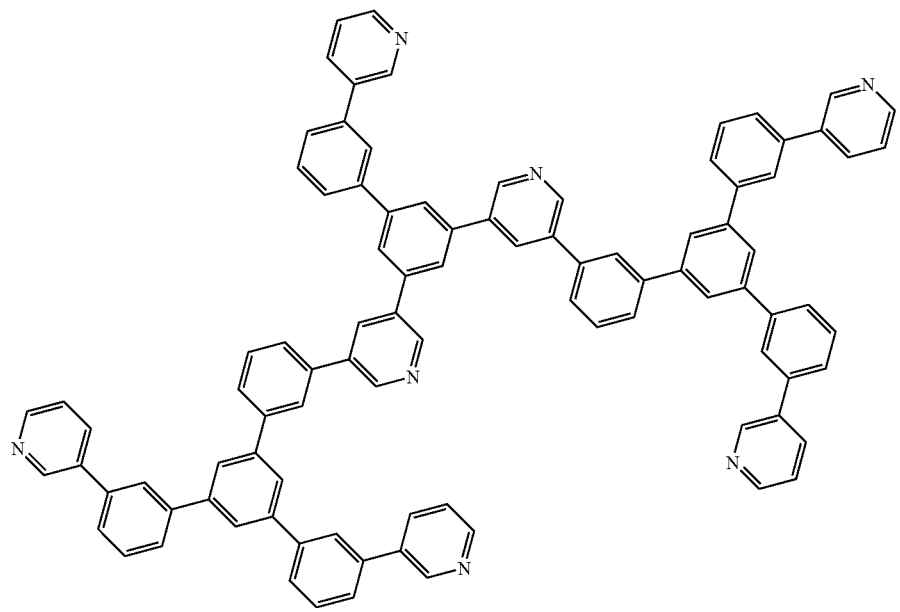

A 100 mL, two-necked, round-bottomed flask covered in tin foil and was equipped with a stirring bar, a reflux condenser fitted with a nitrogen inlet, and a stopper. The flask was charged compound 30 (0.96 g, 1.56 mmol), compound 34 (0.335 g, 0.7 mmol), 1,4-dioxane (30 mL), and tetrakis (triphenylphosphine) palladium (86.9 mg, 0.073 mmol). The apparatus was maintained under an atmosphere of nitrogen during the course of the reaction. The mixture was stirred at room temperature for 20 minutes then potassium carbonate (0.83 g, 5.9 mmol) dissolved in distilled water (8 mL) was added via funnel. The reaction mixture was stirred and heated at reflux in an oil bath for 20 h, then cooled to ambient temperature. Distilled water (30 mL) was added via a funnel, and the resulting mixture was filtered on a Büchner funnel. The filtrate was transferred to a separatory funnel and extracted with $CH_2Cl_2$ (3×30 mL). The combined organic phases were dried over $Na_2SO_4$, filtered on filter paper and concentrated to dryness by rotary evaporation (30° C., 25 mmHg). The resulting yellow solid was purified by column chromatography affording as a white solid 0.63 g (66%). $^1$H NMR (400 MHz, $CDCl_3$) δ 8.95 (m, 9H), 8.63 (m, 5H), 8.22 (m, 2H), 7.97-7.89 (m, 21H), 7.80-7.61 (m, 21H), 7.39 (m, 5H).

Example 19

Synthesis of Compound 36

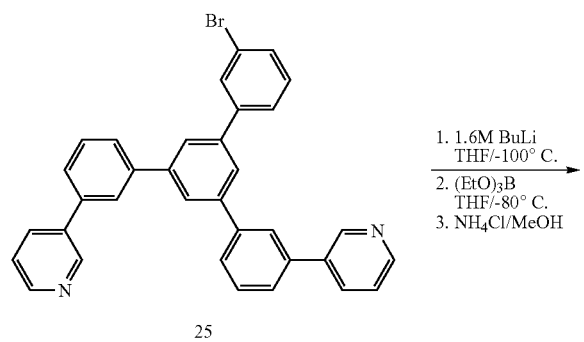

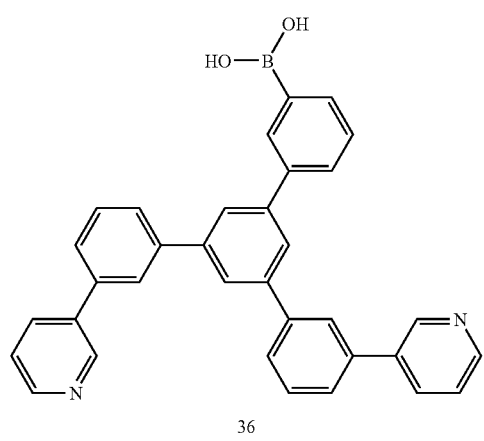

To a flame dried 3-neck round bottom flask fitted with a nitrogen inlet and rubber septa was added compound 25 (2.0 g, 3.7 mmol). The flask was placed under an inert atmosphere and was charged with anhydrous THF (50 mL). The reaction was cooled to −100° C. and 1.6 M BuLi (2.6 mL, 4.1 mmol) was added dropwise and stirred for 10 min. Triethylborate was added to the reaction dropwise at −80° C. and stirred at this temperature for 1 h. The reaction mixture was allowed to warm to RT, and, after stirring for 30 minutes at RT, the mixture was treated with a solution of saturated $NH_4Cl$ (0.5 mL) and concentrated to dryness. The residue was washed with $H_2O$ (3×100 mL) and stirred at RT in a mixture of MeOH (50 mL) and 5% HCl (5 mL) overnight. The solution was neutralized with $NaHCO_3$ and the solvents were removed to dryness. The residue was suspended in acetone (200 mL) and the precipitate was collected by filtration (0.46 g). The mother liquor was concentrated to dryness and the residue was sonicated with EtOAc and the white solid was collected by filtration and washed with EtOAc. Yield 0.65 g, 35%. $^1$H NMR (400 MHz, [$D_6$]-DMSO, 25° C.) δ 7.51 (m, 3H), 7.64 (m, 2H), 7.80 (m, 3H), 7.96 (m, 3H), 8.05 (s, 2H), 8.12 (s, 1H), 8.21 (m, 5H), 8.30 (s, 1H), 8.60 (m, 2H), 9.05 (s, 2H).

Example 20

Synthesis of Compounds 25 & 35

To a purged mixture of $H_2O$ (50 mL) and Dioxane (50 mL) in a 3-neck round bottom flask fitted with a condenser, stopper, and a nitrogen inlet was added $Na_2CO_3$ (10.6 g, 100 mmol), 1,3,5-(3-bromophenyl)-benzene (10.9 g, 20.0 mmol), 3-pyridylboronic acid (5.41 g, 44.0 mmol). After being purged for 15 minutes with $N_2$ Pd(PPh$_3$)$_4$ (0.924 g, 0.800 mmol) was added and the mixture was heated at a gentle reflux for 24 h. The reaction mixture was cooled to room temperature (RT), diluted with $CH_2Cl_2$ (100 mL) and transferred to a separatory funnel containing Satd. $NaHCO_3$ and the reaction flask was rinsed with $CH_2Cl_2$ and $H_2O$. The organic layer was removed and the water layer was extracted with $CH_2Cl_2$ (100 mL), dried over $Na_2SO_4$, and concentrated to dryness to give a foam. The crude product was purified by chromatography through $SiO_2$ eluting with EtOAc. Two products were collected after separation on $SiO_2$. Yield: compound 25 (4.55 g, 42%) and 35 (2.41 g, 22%). $^1$H NMR compound 25 (400 MHz, $CD_2Cl_2$, 25° C.) δ 7.40 (m, 3H), 7.55 (m, 1H), 7.65 (m, 5H), 7.78 (m, 2H), 7.88 (d, 2H), 7.94 (m, 4H), 7.98 (m, 2H), 8.60 (dd, 2H), 8.93 (d, 2H); $^1$H NMR compound 35 (400 MHz, $CD_2Cl_2$, 25° C.) δ 7.40 (m, 3H), 7.55 (m, 2H), 7.65 (m, 4H), 7.77 (m, 2H), 7.89 (m, 5H), 7.99 (m, 1H), 8.61 (dd, 1H), 8.93 (d, 1H).

Example 21

Synthesis of Compound 7

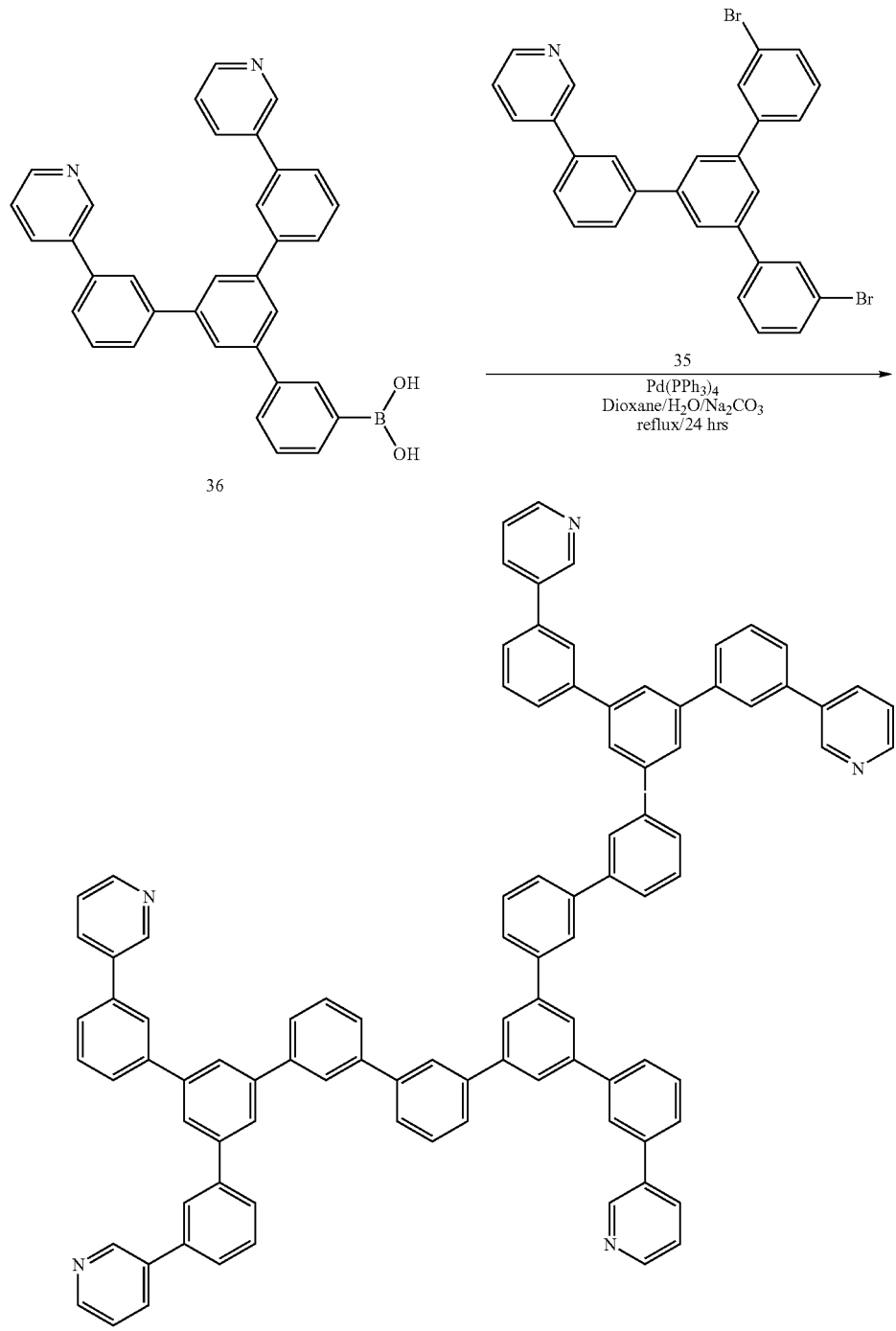

A solution of Dioxane (10 mL)/H$_2$O (10 mL) containing Na$_2$CO$_3$ (579 mg) was purged with nitrogen. To this solution was added the boronic acid compound 36 (682 mg, 1.37 mmol), the dibromo compound 35 (295 mg, 0.546 mmol) followed by Pd(PPh$_3$)$_4$ (60 mg, 0.0500 mmol). The reaction was placed under an inert atmosphere of nitrogen and heat at a gentle reflux for 24 h. The mixture was cooled to RT, diluted with CH$_2$Cl$_2$ (50 mL) and washed with H$_2$O (50 mL). The water layer extracted with CH$_2$Cl$_2$ (2×50 mL) and the combined organic layers were dried over MgSO$_4$. The crude product was chromatographed through SiO$_2$ and eluted with 3% MeOH/CH$_2$Cl$_2$ to afford the product as a white foam. Yield 602 mg, 85%. $^1$H NMR (400 MHz, CD$_2$Cl$_2$, 25° C.) δ 7.36 (m, 5H), 7.62 (m, 14H), 7.77 (m, 13H), 7.97 (m, 19H), 8.04 (m, 4H), 8.57 (s, 5H), 8.91 (m, 5H).

Example 22

Synthesis of Compound 8

A solution of THF (20 mL)/H₂O (20 mL) containing Na₂CO₃ (4.24 g) was purged with nitrogen. To this solution was added the boronic ester compound 29 (2.60 g, 4.43 mmol), 3,5-dibromopyridine (473 mg, 2.00 mmol) followed by Pd(PPh₃)₄ (204 mg, 0.177 mmol). The reaction was placed under an inert atmosphere of nitrogen and heat at reflux for 12 h. The mixture was cooled to RT and the layers were separated. The organic layer washed with NaHCO₃ (1×100 mL), dried over Na₂SO₄, and concentrated to dryness. The filter cake was washed with 5% MeOH/CH₂Cl₂ and the filtrate was concentrated to dryness to give a foam. The crude material was chromatographed through SiO₂ and eluted with 5% MeOH/CH₂Cl₂ to afford the product as a white foam. Yield 1.56 g, 78%. $^1$H NMR (400 MHz, CD₂Cl₂, 25° C.) δ 7.39 (m, 4H), 7.64 (m, 10H), 7.76 (m, 8H), 7.98 (m, 14H), 8.04 (t, 2H), 8.25 (t, 1H), 8.58 (m, 4H), 8.93 (m, 6H).

Example 23

Synthesis of Compound 14

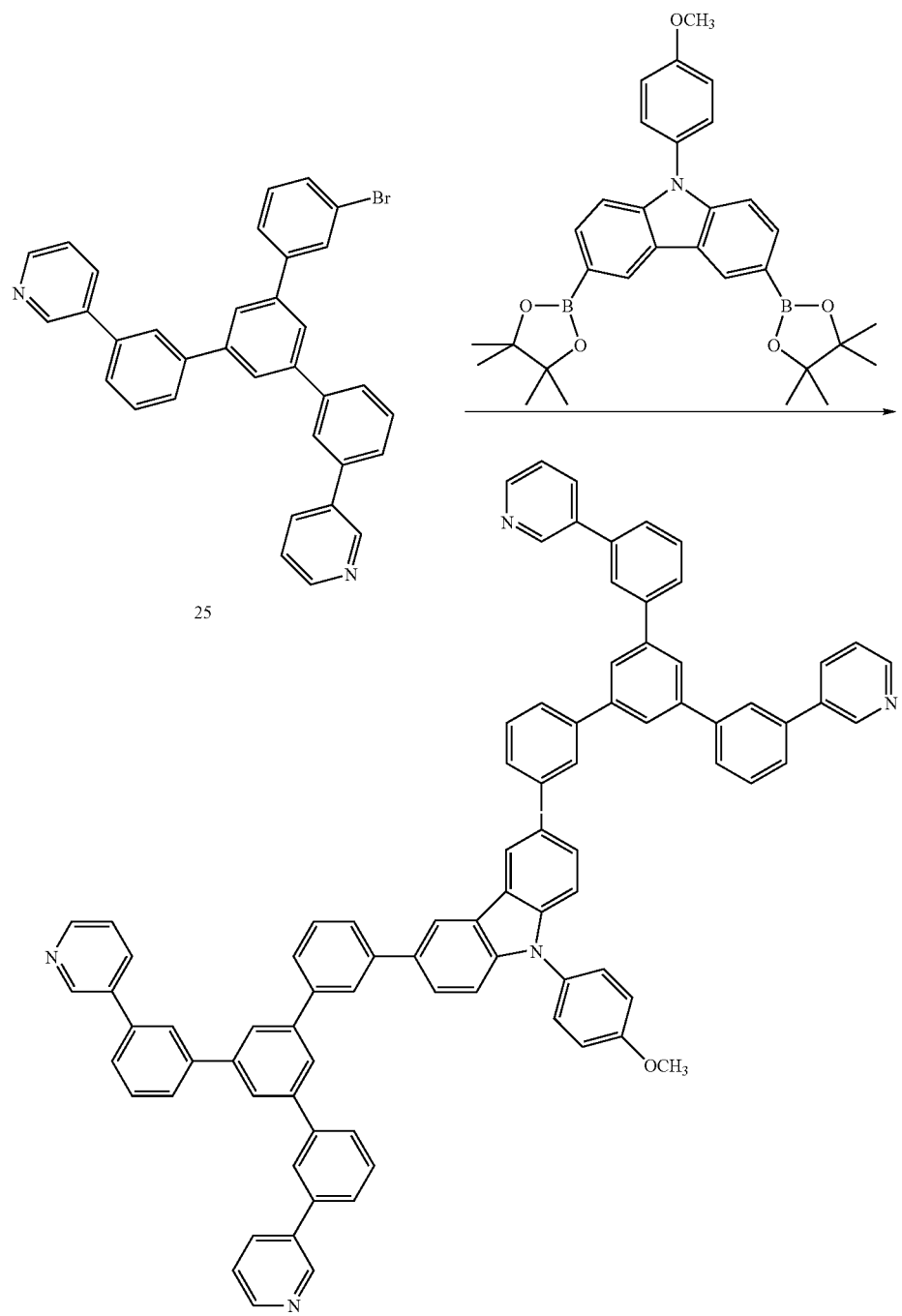

A 100 mL, two-necked, round-bottomed flask covered in tin foil and was equipped with a stirring bar, a reflux condenser fitted with a nitrogen inlet, and a stopper. The flask was charged compound 25 (0.675 g, 1.25 mmol), 9-(4-methoxyphenyl)-3,6-bis(4,4,5,5-tetramethyl-1,3,2-dioxaborolan-2-yl)-9H-carbazole (0.263 g, 0.5 mmol), 1,4-dioxane (20 mL), and tetrakis (triphenylphosphine) palladium (30 mg, 0.025 mmol). The apparatus was maintained under an atmosphere of nitrogen during the course of the reaction. The mixture was stirred at room temperature for 20 minutes then potassium carbonate (0.4 g, 2.84 mmol) dissolved in distilled water (4 mL) was added via funnel. The reaction mixture was stirred and heated at reflux in an oil bath for 20 h, then cooled to ambient temperature. Distilled water (30 mL) was added via a funnel, and the resulting mixture was filtered on a Büchner funnel. The filtrate was transferred to a separatory funnel and extracted with $CH_2Cl_2$ (3×30 mL). The combined organic phases were dried over $Na_2SO_4$, filtered on paper and concentrated to dryness by rotary evaporation (30° C., 25 mmHg). Then purified by column chromatography on silica gel (EtOAc/THF=6:1) to give compound 14 (0.24 g, 40%). 1H NMR (400 MHz, CDCl3) δ 8.93 (br s, 4H), 8.62 (br s, 4H), 8.49 (m, 2H), 8.05 (m, 2H), 7.96-7.90 (m, 14H), 7.77-7.39 (m, 28H), 7.17 (m, 2H), 3.96 (s, 3H).

Example 24

Synthesis Compound 16

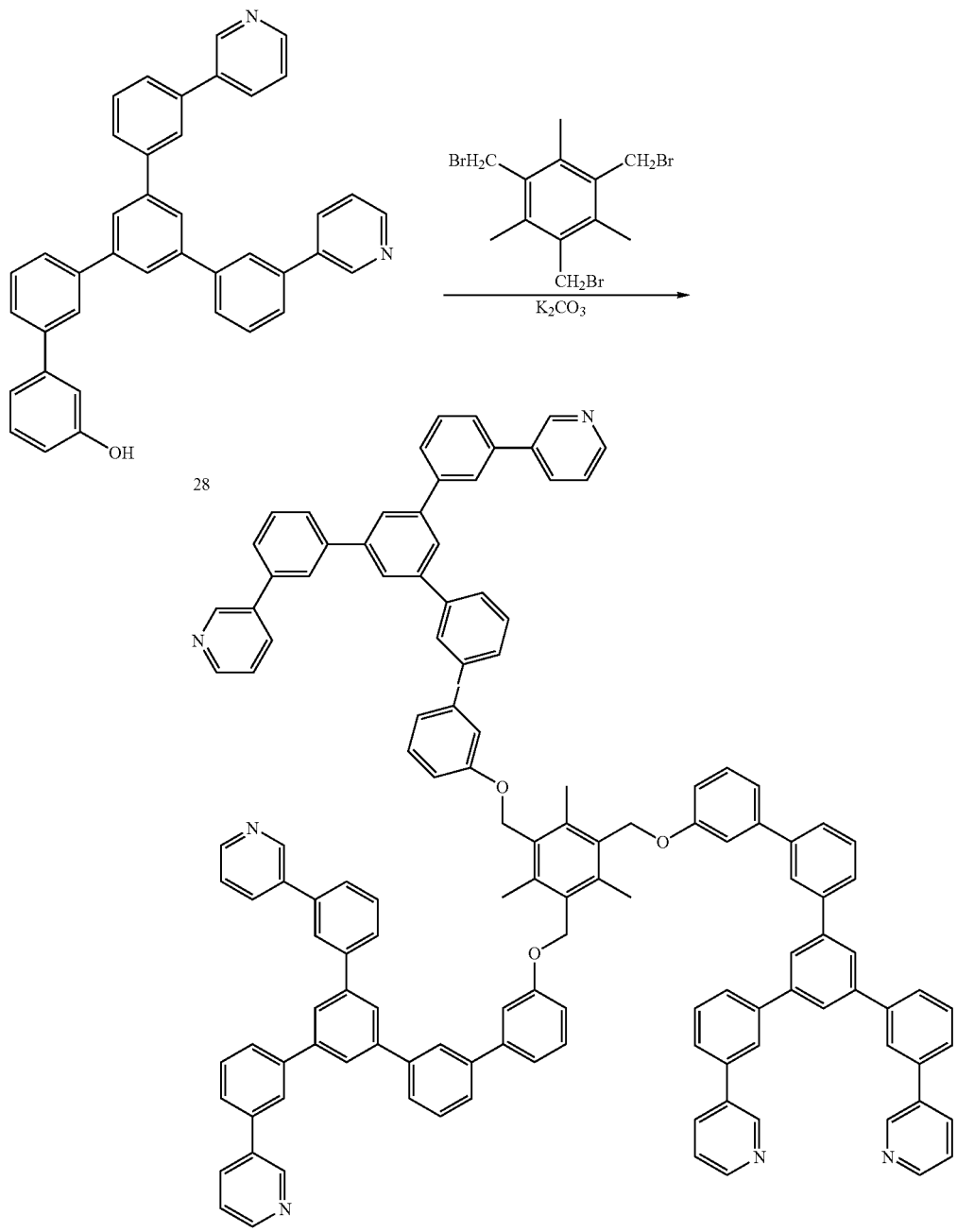

A 25 mL round bottom flask equipped with a magnetic stir bar was charged with 1,4-dioxane (10 mL). A mixture of Compound 28 (0.365 g, 0.66 mmol), 1,3,5-tris(bromomethyl)-2,4,6-trimethylbenzene (0.075 g, 0.189 mmol) and potassium carbonate (0.182 g, 1.34 mmol) was dissolved in the solvent. The reaction was refluxed over night under nitrogen. The reaction mixture was allowed to cool to room temperature and diluted with $CH_2Cl_2$. The combined organic phases were dried over $Na_2SO_4$, filtered on filter paper and concentrated to dryness by rotary evaporation (30° C., 25 mmHg). The resulting yellow solid was purified by column chromatography ($SiO_2$; Ethyl acetate/THF(V/V:4/1) as eluant) to give compound 16 as a white solid (0.29, 85%). $^1H$ NMR (400 MHz, $CDCl_3$) δ 8.97 (s, 6H), 8.65 (s, 6H), 7.99 (d, 6H), 7.90 (m, 18H), 7.77 (m, 6H), 7.70 (d, 6H), 7.63 (m, 15H), 7.55 (t, 3H), 7.43 (t, 6H), 7.34 (t, 3H), 7.21 (m, 6H), 6.91 (d, 3H), 5.32 (S, 6H), 1.9 (s, 9H).

Example 25

Synthesis of Compound 38

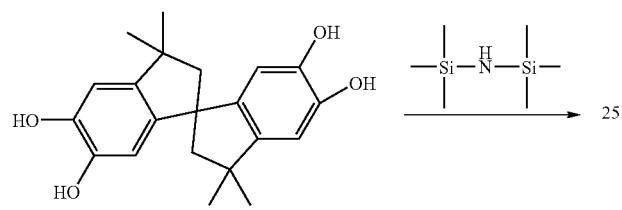

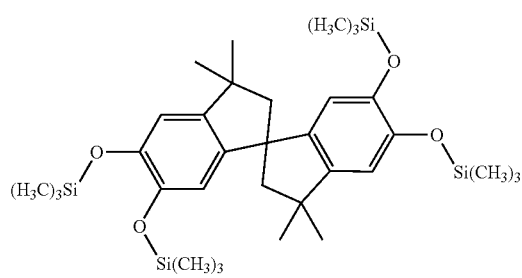

38

Spirobisindane tetraphenol (3.4 g, 10 mmol) was added into 4 g (24.8 mmol) of hexamethyldisilazane, and refluxed overnight at 120-125° C. It started out as a suspension and it turned into a clear solution after about 1 hour. Excess amount of the hexamethyldisilazane was removed by distillation. $^1H$ NMR ($CDCl_3$): 6.6 (s, 2H), 6.2 (s, 2H), 2.2 (dd, 4H), 1.34 (s, 6H), 1.30 (s, 6H), 0.24 (s, 18H), 0.18 (s, 18H).

Example 26

Synthesis of Compound 17

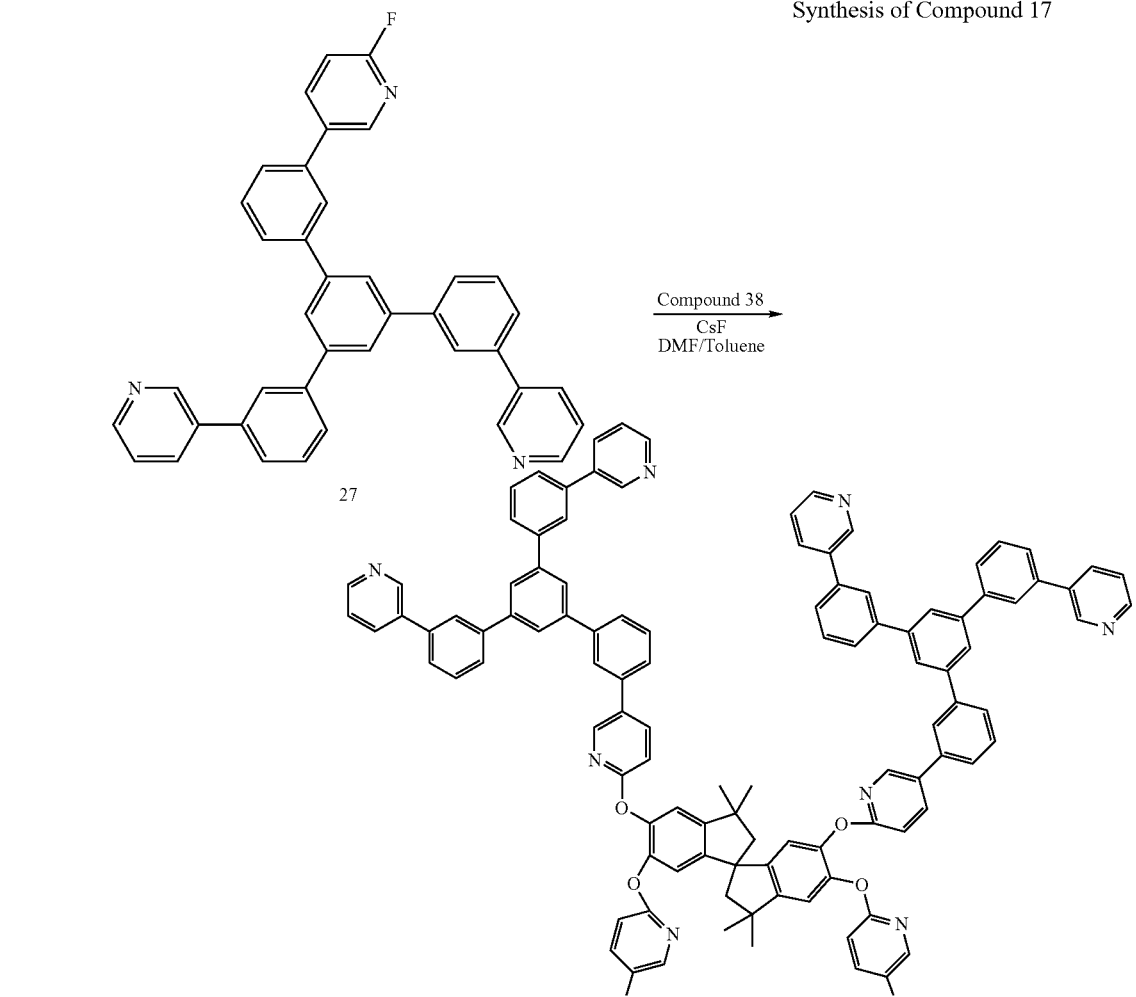

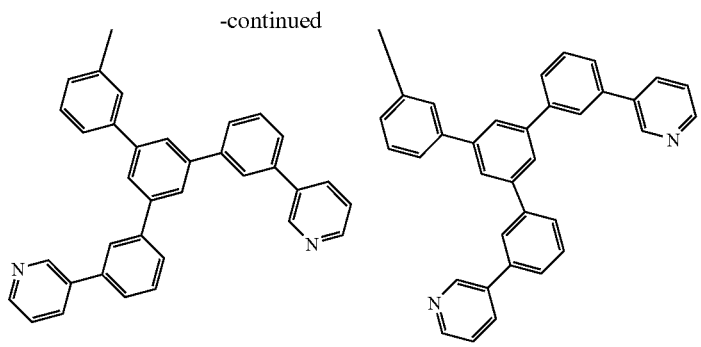

17

Compound 27 (0.19 g, 0.3419 mmol) and 0.047 g (0.0747 mmol) of silylate tetraphenol (compound 38) was combined in a three neck round bottom flask at room temperature. To this flask, 3 mL of anhydrous DMF and 3 mL of anhydrous toluene was added. The flask was heated to 130° C. under a stream of argon. After toluene removal, then very small amount of anhydrous CsF(about 5 mg) was added. The temperature was raised to 140° C. The reaction was monitored by silica gel TLC. 0.075 g of the o-fluoro-STPPB and 2 mL of toluene was added after 4 days. And the reaction was stopped after another two days. After the reaction mixture was cooled to room temperature, it was dumped into 10 mL of water. Methylene choride (5 mL) was used to extract the solid. The organic layer was washed water 5 mL (×2), brine (×1), and dried over MgSO$_4$. Solvent was removed on roto-evaporator. The crude product was separated by silica gel column using THF/Hex (1/1-8/1) as elute. Obtained about ~100 mg of yellowish solid. And solid was dissolved in CH$_2$Cl$_2$, and hexane was added till white solid came out. 0.048 g of very fine white solid was collected by suction filtration through fine frit. Then the white solid was attempted to be re-dissolved in ethanol, a little CH$_2$Cl$_2$ was added to help the solubility. Some powders came out after overnight but all stuck on the wall of the flask. 8 mg of products were collected from the supernatant. $^1$H NMR (CDCl$_3$): 8.90 (d, 8H), 8.61 (t, 8H), 8.37 (d, 4H), 7.99-7.26 (m, 68H), 6.94 (s, 2H), 7.12 (s, 2H), 6.8 (dd, 4H), 2.48 (dd, 4H), 1.45 (s, 6H), 1.43 (s, 6H). Maldi (M+=2482.2286).

Example 27

Synthesis of Compound of Formula 39

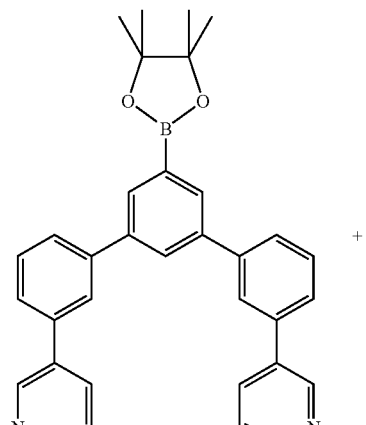

40

+

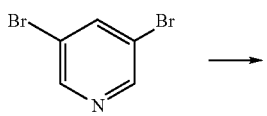

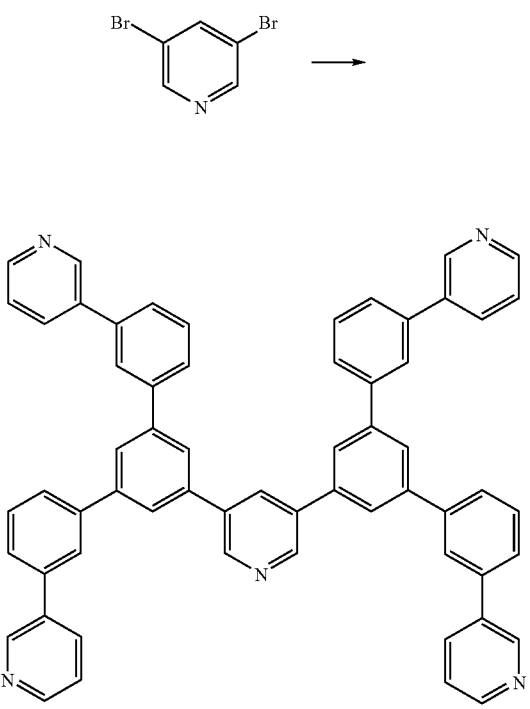

39

Compound 40 (0.34 g, 0.67 mmol) and 3,5-dibromopyridine (0.063 g, 0.26 mmol) was added to a 50 mL schlenk flask. To this flask, anhydrous THF (5 mL) and (0.347 g, 1.065 mmol) were added. The mixture was stirred and degassed with a steam of argon for 15 min. Then under argon atmosphere Pd(PPh$_3$)$_4$ was added. The mixture was brought to 60° C. and stirred for 2 days. After cooling to room temperature, the solution was filtered. And solvent was removed by roto-evaporation and residue was purified by column chromatography on silica gel, using 5% MeOH in CH$_2$Cl$_2$ as eluting solvent. Yield is 0.25 g, 50%. $^1$H NMR (o, CDCl$_3$) 9.02 (d, 2H), 8.91 (d, 4H), 9.61 (dd, 4H), 8.30 (t, 1H), 7.92 (tm, 14H), 7.76 (m, 4H), 7.62-7.61 (m, 8H), 7.37 (dd, 4H). MALDI (M+H$^+$) 844.3884

Example 28

Synthesis of Compound 40

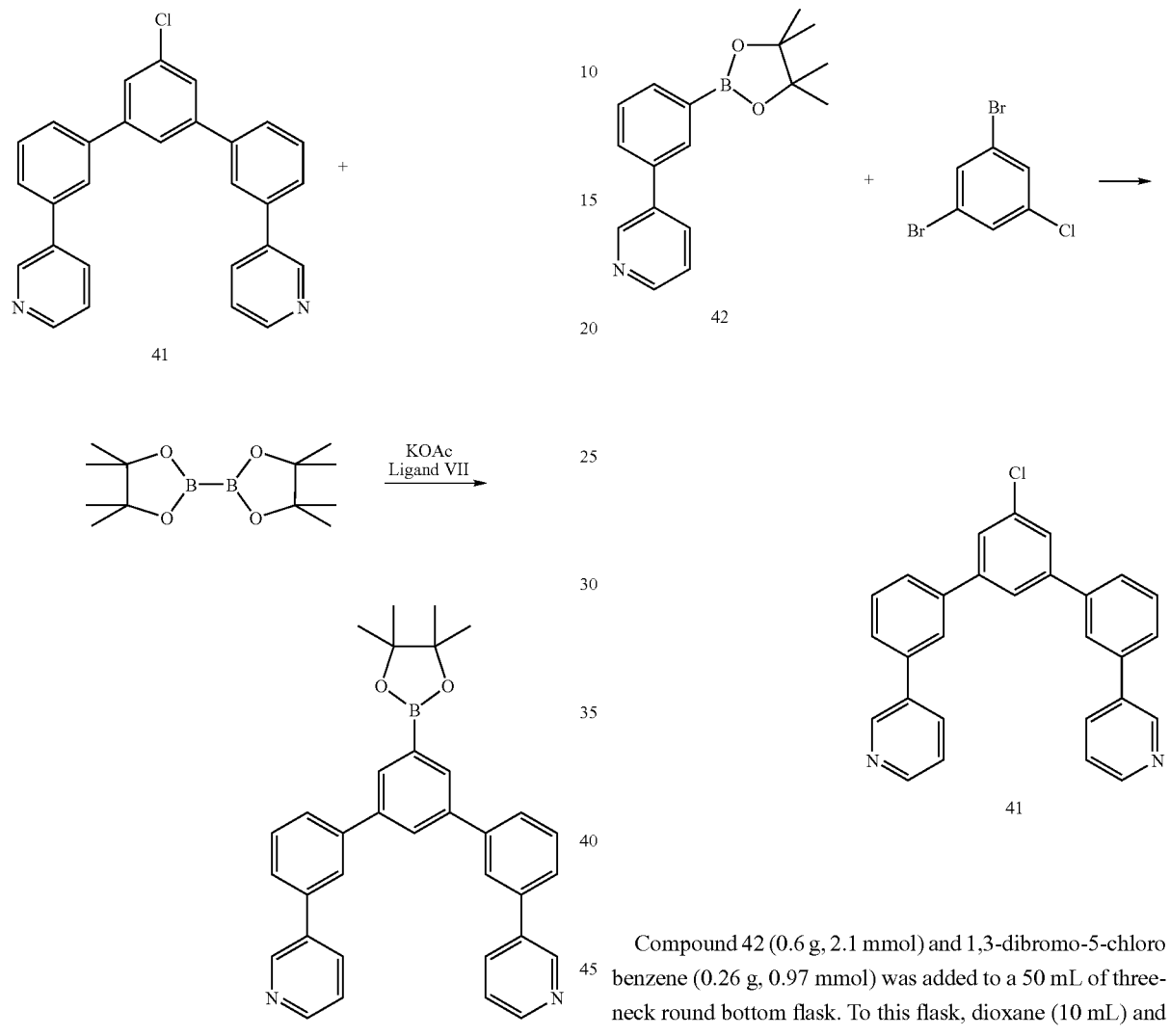

Example 29

Synthesis of Compound 41

To a schlenk tube was charged compound 41 (0.419 g, 1 mmol), pinacolate diborane (0.762 g, 3 mmol), dry KOAc (0.294 g, 3 mmol), ligand VII (0.016 mg, 0.04 mmol) and Pd(OAc)$_2$ (13.46 mg, 0.02 mmol). The schlenk tube was evacuated and filled with argon three times. The schlenk was placed in a nitrogen box. Anhydrous THF (5 mL) from the solvent distill was added. The flask was then sealed tightly and placed in an oil bath and heated at 60° C. for 4 days. After the reaction mixture was cooled to RT and filtered through a filter paper. The filter cake was washed with EtOAc and the filtrate was concentrated to dryness. The residue was chromatographed through SiO$_2$ with EtOAc eluent. Yield was 65%. $^1$H NMR (δ, CDCl$_3$) 8.82 (s, 2H), 8.51 (s, 2H), 8.00 (d, 2H), 7.89 (m, 2H), 7.86 (t, 1H), 7.78 (s, 2H), 7.64 (m, 2H), 7.49 (m, 4H), 7.31 (dd, 2H), 1.29 (s, 12H).

Compound 42 (0.6 g, 2.1 mmol) and 1,3-dibromo-5-chloro benzene (0.26 g, 0.97 mmol) was added to a 50 mL of three-neck round bottom flask. To this flask, dioxane (10 mL) and aqueous K$_2$CO$_3$ (2 N, 5 mL) was added. The mixture was stirred and degassed with a steam of argon for 15 minutes. Then under argon atmosphere 0.03 g of Pd(PPh$_3$)$_4$ was added. The mixture was brought to 80° C. and stirred overnight. The next day, solvent was removed by roto-evaporation and residue was suspended into an equal amount of water (10 mL) and CH$_2$Cl$_2$ (10 mL). The organic layer was separated from aqueous layer and washed with water (5 mL) and brine solution (5 mL). After dried over Na$_2$SO$_4$, and followed by removal of drying agent and organic solvent was removed by roto-evaporation. The residue was purified by column chromatography on silica gel, using EtOAc as eluting solvent. Yield is 0.25 g, 90%. $^1$H NMR (δ, CDCl$_3$) 8.92 (s, 2H), 8.64 (s, 2H), 7.94 (d, 2H), 7.80 (s, 2H), 7.75 (s, 1H), 7.63 (dd, t, 8H), 7.39 (dd, 2H).

Example 30

Synthesis of Compound 42

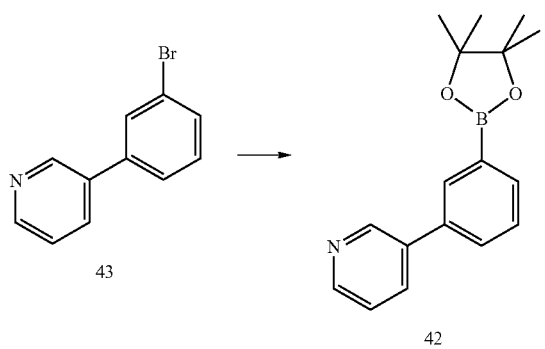

To a 3-neck round bottom flask fitted with a condenser, an argon inlet, and a rubber septum was added compound 43 (1.8 g, 7.7 mmol), pinacolate diborane (5.86 g, 23.1 mmol), dry KOAc (2.26 g, 23.1 mmol), and the cyclohexyl phosphine ligand (158.6 mg, 0.385 mmol). The flask was placed then protected from the atmosphere and was charged with anhydrous THF (30 mL), Dioxane (7.5 mL), and the solution was degassed by purging argon through the stirred solution. After 15 minutes, the reaction mixture was charged with Pd(OAc)$_2$ (35.4 mg, 0.150 mmol) and the mixture was heated at 60° C. for 12 hours. After this time had passed, the reaction mixture was cooled to room temperature and filtered through a filter paper. The filter cake was washed with EtOAc and the filtrate was concentrated to dryness. The residue was chromatographed through SiO$_2$ with a Hexane/EtOAc eluent. Yield was 90%. $^1$H NMR ($\delta$, CDCl$_3$) 8.89 (d, 1H), 8.61 (dd, 1H), 8.05 (s, 1H), 7.94 (dt, 1H), 7.88 (d, 1H), 7.71 (d, 1H), 7.51 (t, 1H), 7.38 (dd, 1H), 1.39 (s, 12H).

Example 31

Synthesis of Compound 43

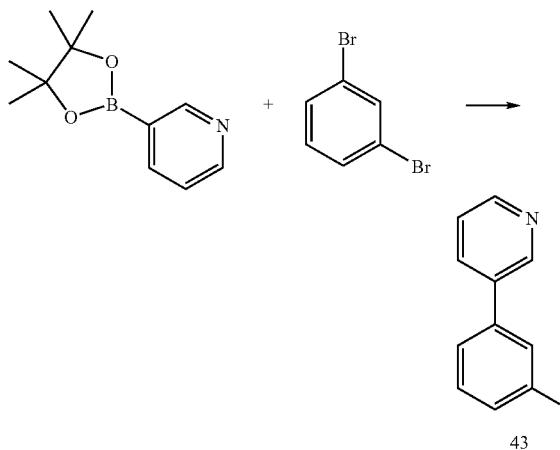

3-Pyridineboronic acid pinacol ester (8.7 g, 42.4 mmol) and 1,3-dibromo benzene (50.04 g, 212 mmol) were added to a 500 mL of three-neck round bottom flask. To this flask, dioxane (250 mL) and aqueous K$_2$CO$_3$ (2 N, 125 mL) was added. The mixture was stirred and degassed with a steam of argon for 30 minutes. Then under argon atmosphere 1 g of Pd(PPh$_3$)$_4$ was added. The mixture was brought to 80° C. and stirred overnight. The next day, solvent was removed by rotoevaporation and residue was suspended into an equal amount of water (200 mL) and CH$_2$Cl$_2$ (200 mL). The organic layer was separated from aqueous layer and washed with water (100 mL) and brine solution (100 mL). After dried over Na$_2$SO$_4$, and removal of drying agent, some silica gel was added to flask and the mixture was evaporated down to dryness. This silica gel absorbed with mixture of starting material and product was transferred to a medium frit preload with a bed of fresh silica gel. Hexane (1 L) was used to rinsed the bed afford un-reacted starting material. Ethyl acetated (1 L) was rinsed to the silica gel bed, afford ~9 g of product. $^1$H NMR (CDCl$_3$) $\delta$ 8.83 (dd, 1H), 8.64 (dd, 1H), 7.86 (dt, 1H), 7.74 (t, 1H), 7.55 (dt, 1H), 7.52 (dt, 1H), 7.39 (dd, 1H), 7.37 (t, 1H).

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A compound of formula VIII

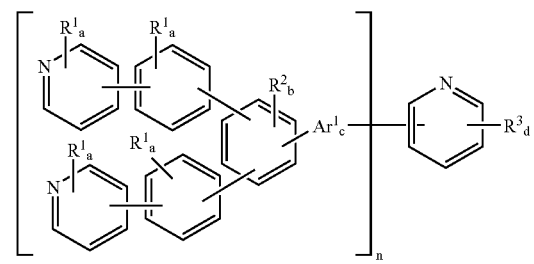

wherein
R$^1$, R$^2$ and R$^3$ are, independently at each occurrence, a C$_1$-C$_{20}$ aliphatic radical, a C$_3$-C$_{20}$ aromatic radical, or a C$_3$-C$_{20}$ cycloaliphatic radical;
a and d are, independently at each occurrence, an integer ranging from 0-4;
b is, independently at each occurrence, an integer ranging from 0-3;
Ar$^1$ is a direct bond or heteroaryl, aryl, or alkyl or cycloalkyl;
c is 0, 1 or 2; and
n is an integer ranging from 2-4.

2. The compound according to claim 1, being of formula

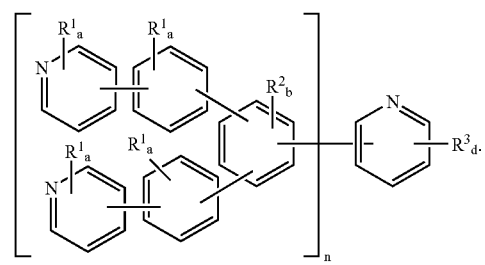

3. The compound according to claim 1, being of formula

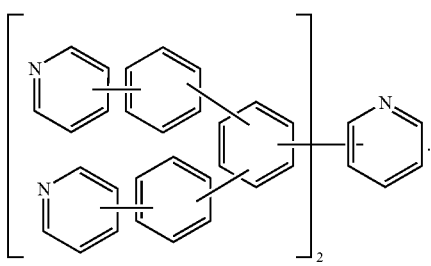

4. The compound according to claim 1, wherein $Ar^1$ is a direct bond.

5. The compound according to claim 1, wherein $Ar^1$ is independently chosen from

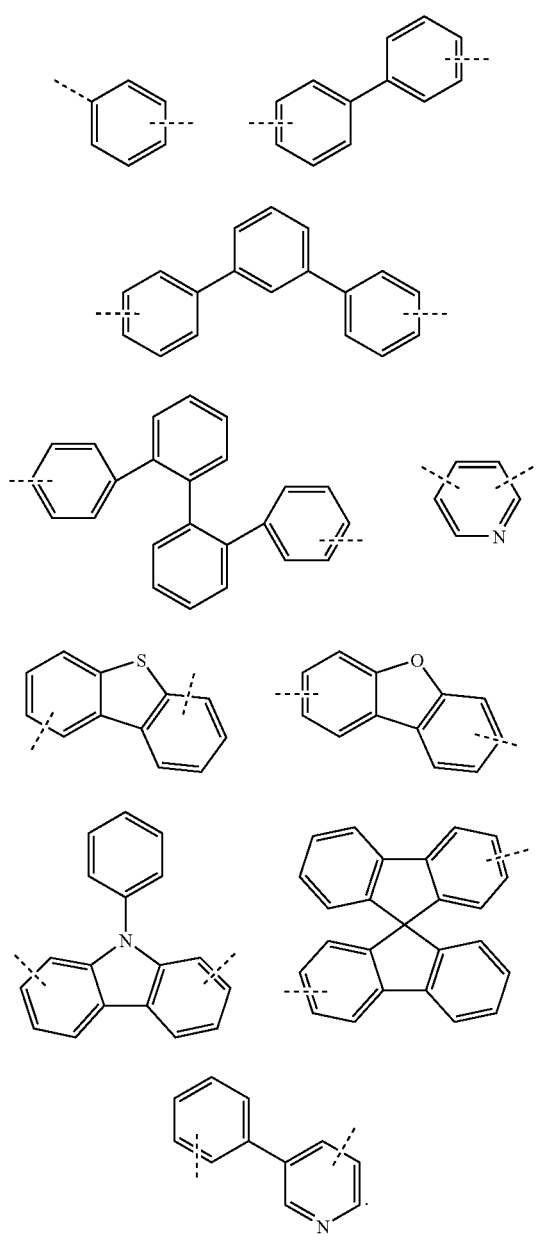

6. The compound according to claim 1, being of formula

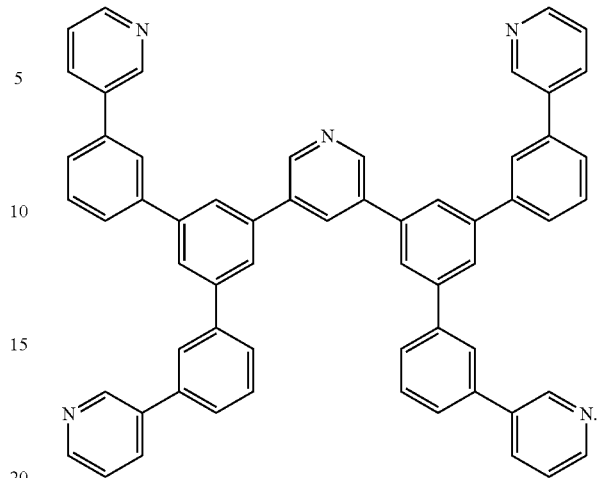

7. An optoelectronic device comprising at least one compound of formula VIII

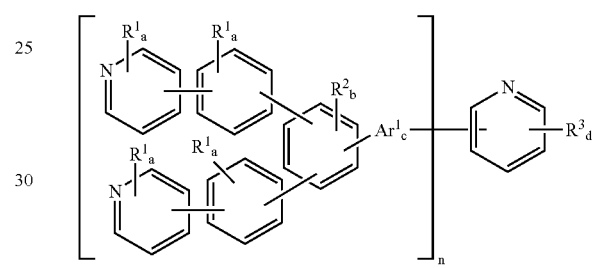

wherein
$R^1$, $R^2$ and $R^3$ are, independently at each occurrence, a $C_1$-$C_{20}$ aliphatic radical, a $C_3$-$C_{20}$ aromatic radical, or a $C_3$-$C_{20}$ cycloaliphatic radical;
a and d are, independently at each occurrence, an integer ranging from 0-4;
b is, independently at each occurrence, an integer ranging from 0-3;
$Ar^1$ is a direct bond or heteroaryl, aryl, or alkyl or cycloalkyl;
c is 0, 1 or 2; and
n is an integer ranging from 2-4.

8. The optoelectronic device according to claim 7, wherein the at least one compound is of formula

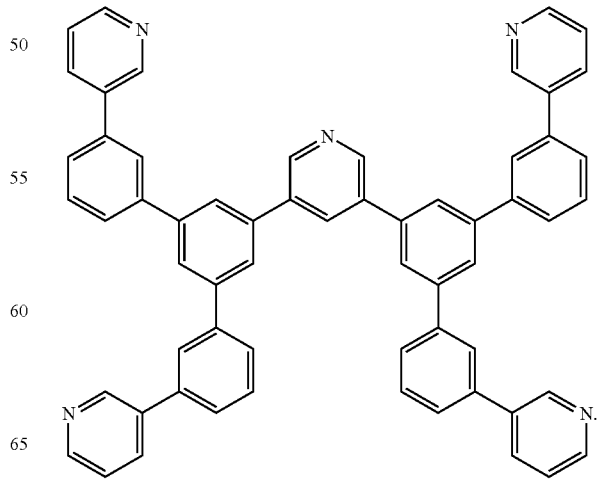

9. The optoelectronic device according to claim 7, being an organic light emitting device.

10. The optoelectronic device according to claim 9, comprising an electron transporting layer comprising the at least one compound of formula VIII.

11. The optoelectronic device according to claim 7, additionally comprising at least one blue, yellow, orange, or red phosphorescent dye, or a combination thereof.

* * * * *